US011717602B2

(12) United States Patent
Friedman et al.

(10) Patent No.: US 11,717,602 B2
(45) Date of Patent: Aug. 8, 2023

(54) SYSTEMS AND METHODS FOR MEDICAL DEVICE CONTROL

(71) Applicant: LifeCell Corporation, Madison, NJ (US)

(72) Inventors: Evan J. Friedman, West Orange, NJ (US); Israel James Jessop, Garden Ridge, TX (US); Kai-Roy Wang, Jersey City, NJ (US); Aaron Barere, Hoboken, NJ (US); Brendan P. Collins, Manchester, NH (US); Derek Hugger, Goffstown, NH (US); Christopher Labak, Brookline, NH (US); Scott Woodruff, Chicago, IL (US)

(73) Assignee: LifeCell Corporation, North Chicago, IL (US)

( * ) Notice: Subject to any disclaimer, the term of this patent is extended or adjusted under 35 U.S.C. 154(b) by 0 days.

(21) Appl. No.: 17/402,791

(22) Filed: Aug. 16, 2021

(65) Prior Publication Data

US 2022/0106555 A1 Apr. 7, 2022

Related U.S. Application Data

(63) Continuation of application No. 16/585,965, filed on Sep. 27, 2019, now Pat. No. 11,091,733, which is a
(Continued)

(51) Int. Cl.
*A61M 1/00* (2006.01)
*B01F 27/84* (2022.01)
(Continued)

(52) U.S. Cl.
CPC .......... *A61M 1/60* (2021.05); *B01F 27/1124* (2022.01); *B01F 27/2124* (2022.01);
(Continued)

(58) Field of Classification Search
None
See application file for complete search history.

(56) References Cited

U.S. PATENT DOCUMENTS 3,749,088 A 7/1973 Kohlmann
3,791,524 A 2/1974 Cho
(Continued)

FOREIGN PATENT DOCUMENTS

CA 2469370 A1 7/2003
CA 2750498 A1 6/2012
(Continued)

OTHER PUBLICATIONS

U.S. Appl. No. 13/894,912, filed May 15, 2013, U.S. Pat. No. 9,278,165, Issued.
(Continued)

*Primary Examiner* — Jyoti Nagpaul
(74) *Attorney, Agent, or Firm* — McCarter & English, LLP

(57) ABSTRACT

Systems, devices, and methods of the present disclosure assist with management of tubes and hoses during surgical procedures. The systems, devices, and methods provide for the proper opening and closing of tubes to facilitate performance of steps in a surgical procedure. Systems, devices, and methods of the present disclosure control fluid delivery to and from a medical device, including devices for tissue processing and cleaning.

20 Claims, 66 Drawing Sheets

Related U.S. Application Data continuation of application No. 15/688,387, filed on Aug. 28, 2017, now Pat. No. 10,472,603.

(60) Provisional application No. 62/381,118, filed on Aug. 30, 2016.

(51) Int. Cl.
  *B01F 27/90* (2022.01)
  *B01F 27/1124* (2022.01)
  *B01F 27/2124* (2022.01)
  *C12M 1/00* (2006.01)
  *B01F 101/00* (2022.01)

(52) U.S. Cl.
  CPC .............. *B01F 27/84* (2022.01); *B01F 27/90* (2022.01); *C12M 29/04* (2013.01); *C12M 47/12* (2013.01); *A61M 1/892* (2021.05); *A61M 2202/005* (2013.01); *A61M 2202/0021* (2013.01); *A61M 2202/0028* (2013.01); *A61M 2202/0071* (2013.01); *A61M 2202/0085* (2013.01); *A61M 2202/08* (2013.01); *A61M 2205/75* (2013.01); *B01F 2101/2202* (2022.01)

(56) References Cited

U.S. PATENT DOCUMENTS

| | | |
|---|---|---|
| 3,854,704 A | 12/1974 | Balas |
| 3,855,997 A | 12/1974 | Sauer |
| 3,987,819 A | 10/1976 | Scheuermann |
| 3,993,067 A | 11/1976 | Schachet et al. |
| 4,438,032 A | 3/1984 | Golde et al. |
| 4,457,339 A | 7/1984 | Juan et al. |
| 4,539,106 A | 9/1985 | Schwartz |
| 4,681,571 A | 7/1987 | Nehring |
| 4,753,634 A | 6/1988 | Johnson |
| 4,820,626 A | 4/1989 | Williams et al. |
| 4,821,996 A | 4/1989 | Bellotti et al. |
| 4,846,800 A | 7/1989 | Ouriel et al. |
| 4,870,975 A | 10/1989 | Cronk et al. |
| 4,898,572 A | 2/1990 | Surugue nee Lasnier et al. |
| 4,957,492 A | 9/1990 | McVay |
| 4,988,623 A | 1/1991 | Schwarz et al. |
| 5,035,708 A | 7/1991 | Alchas et al. |
| 5,049,273 A | 9/1991 | Knox |
| 5,055,198 A | 10/1991 | Shettigar |
| 5,226,914 A | 7/1993 | Caplan et al. |
| 5,301,685 A | 4/1994 | Guirguis |
| 5,318,510 A | 6/1994 | Cathcart |
| 5,330,914 A | 7/1994 | Uhlen et al. |
| 5,336,616 A | 8/1994 | Livesey et al. |
| 5,372,945 A | 12/1994 | Alchas et al. |
| 5,409,833 A | 4/1995 | Hu et al. |
| D360,698 S | 7/1995 | Stevens et al. |
| 5,486,359 A | 1/1996 | Caplan et al. |
| 5,586,732 A | 12/1996 | Yamauchi et al. |
| 5,591,625 A | 1/1997 | Gerson et al. |
| 5,601,707 A | 2/1997 | Clay et al. |
| 5,610,074 A | 3/1997 | Beritashvili et al. |
| 5,624,418 A | 4/1997 | Shepard |
| 5,624,840 A | 4/1997 | Naughton et al. |
| 5,645,540 A | 7/1997 | Henniges et al. |
| 5,688,531 A | 11/1997 | Benayahu et al. |
| 5,713,879 A | 2/1998 | Schneider |
| 5,728,739 A | 3/1998 | Ailhaud et al. |
| 5,736,396 A | 4/1998 | Bruder et al. |
| 5,785,640 A | 7/1998 | Kresch et al. |
| 5,786,207 A | 7/1998 | Katz et al. |
| 5,811,094 A | 9/1998 | Caplan et al. |
| 5,817,032 A | 10/1998 | Williamson, IV et al. |
| 5,817,050 A | 10/1998 | Klein |
| 5,823,986 A | 10/1998 | Peterson |
| 5,827,735 A | 10/1998 | Young et al. |
| 5,827,740 A | 10/1998 | Pittenger |
| 5,827,897 A | 10/1998 | Ailhaud et al. |
| D401,336 S | 11/1998 | Muller et al. |
| 5,853,398 A | 12/1998 | Lal et al. |
| 5,854,292 A | 12/1998 | Ailhaud et al. |
| 5,901,717 A | 5/1999 | Dunn et al. |
| 5,906,934 A | 5/1999 | Grande et al. |
| 5,908,784 A | 6/1999 | Johnstone et al. |
| 5,937,863 A | 8/1999 | Knowlton |
| 5,968,356 A | 10/1999 | Morsiani et al. |
| 6,017,493 A | 1/2000 | Cambron et al. |
| D424,194 S | 5/2000 | Holdaway et al. |
| D426,744 S | 6/2000 | Wong |
| 6,200,606 B1 | 3/2001 | Peterson et al. |
| 6,258,054 B1 | 7/2001 | Mozsary et al. |
| 6,261,549 B1 | 7/2001 | Fernandez et al. |
| 6,316,247 B1 | 11/2001 | Katz et al. |
| 6,325,788 B1 | 12/2001 | McKay |
| 6,391,297 B1 | 5/2002 | Halvorsen |
| 6,429,013 B1 | 8/2002 | Halvorsen et al. |
| 6,478,966 B2 | 11/2002 | Zhou et al. |
| 6,544,788 B2 | 4/2003 | Singh |
| 6,555,374 B1 | 4/2003 | Gimble et al. |
| 6,623,733 B1 | 9/2003 | Hossainy et al. |
| 6,733,537 B1 | 5/2004 | Fields et al. |
| D492,995 S | 7/2004 | Rue et al. |
| 6,777,231 B1 | 8/2004 | Katz et al. |
| 6,841,150 B2 | 1/2005 | Halvorsen et al. |
| 6,852,533 B1 | 2/2005 | Rafii et al. |
| 7,001,746 B1 | 2/2006 | Halvorsen et al. |
| 7,033,587 B2 | 4/2006 | Halvorsen et al. |
| 7,078,230 B2 | 7/2006 | Wilkison et al. |
| 7,078,232 B2 | 7/2006 | Konkle et al. |
| 7,147,826 B2 | 12/2006 | Haywood et al. |
| 7,172,572 B2 | 2/2007 | Diamond et al. |
| 7,179,649 B2 | 2/2007 | Halvorsen |
| 7,266,457 B1 | 9/2007 | Hickman |
| 7,294,334 B1 | 11/2007 | Michal et al. |
| 7,361,368 B2 | 4/2008 | Claude et al. |
| 7,390,484 B2 | 6/2008 | Fraser et al. |
| D575,393 S | 8/2008 | Stephens |
| 7,429,488 B2 | 9/2008 | Fraser et al. |
| 7,470,537 B2 | 12/2008 | Hedrick et al. |
| 7,473,420 B2 | 1/2009 | Fraser et al. |
| 7,501,115 B2 | 3/2009 | Fraser et al. |
| 7,514,075 B2 | 4/2009 | Hedrick et al. |
| 7,531,355 B2 | 5/2009 | Rodriguez et al. |
| 7,572,236 B2 | 8/2009 | Quick et al. |
| 7,582,292 B2 | 9/2009 | Wilkison et al. |
| 7,585,670 B2 | 9/2009 | Hedrick et al. |
| 7,588,732 B2 | 9/2009 | Buss |
| 7,595,043 B2 | 9/2009 | Hedrick et al. |
| 7,622,108 B2 | 11/2009 | Collins et al. |
| 7,641,643 B2 | 1/2010 | Michal et al. |
| 7,651,684 B2 | 1/2010 | Hedrick et al. |
| 7,659,118 B2 | 2/2010 | Furcht et al. |
| 7,670,596 B2 | 3/2010 | Collins et al. |
| 7,687,059 B2 | 3/2010 | Fraser et al. |
| 7,708,152 B2 | 5/2010 | Dorian et al. |
| D618,819 S | 6/2010 | Wilkinson et al. |
| 7,727,763 B2 | 6/2010 | McKenna, Jr. et al. |
| 7,732,190 B2 | 6/2010 | Michal et al. |
| 7,744,820 B2 | 6/2010 | Togawa et al. |
| 7,744,869 B2 | 6/2010 | Simon |
| 7,749,741 B2 | 7/2010 | Bullen et al. |
| 7,771,716 B2 | 8/2010 | Hedrick et al. |
| 7,780,649 B2 | 8/2010 | Shippert |
| 7,780,860 B2 | 8/2010 | Higgins et al. |
| 7,789,872 B2 | 9/2010 | Shippert |
| 7,794,449 B2 | 9/2010 | Shippert |
| 7,887,795 B2 | 2/2011 | Fraser et al. |
| 7,901,672 B2 | 3/2011 | Fraser et al. |
| 8,062,286 B2 | 11/2011 | Shippert |
| 8,100,874 B1 | 1/2012 | Jordan et al. |
| D660,453 S | 5/2012 | Jani et al. |
| 8,172,818 B2 | 5/2012 | Locke et al. |
| 8,292,839 B2 | 10/2012 | O'Neill |
| 8,293,532 B2 | 10/2012 | Moynahan |
| 8,333,740 B2 | 12/2012 | Shippert |
| 8,337,711 B2 | 12/2012 | Dorian et al. |

(56) References Cited

U.S. PATENT DOCUMENTS

| | | |
|---|---|---|
| 8,366,694 B1 | 2/2013 | Jordan |
| D679,011 S | 3/2013 | Kitayama et al. |
| 8,409,860 B2 | 4/2013 | Moynahan |
| D683,851 S | 6/2013 | Greenhalgh |
| D687,549 S | 8/2013 | Johnson et al. |
| D692,559 S | 10/2013 | Scheibel et al. |
| 8,622,997 B2 | 1/2014 | Shippert |
| 8,632,498 B2 | 1/2014 | Rimsa et al. |
| 8,840,614 B2 | 9/2014 | Mikhail et al. |
| 8,858,518 B2 | 10/2014 | Schafer et al. |
| 8,887,770 B1 | 11/2014 | Shippert |
| 9,206,387 B2 | 12/2015 | Llull et al. |
| 9,260,697 B2 | 2/2016 | Cimino et al. |
| 9,278,165 B2 | 3/2016 | Park et al. |
| 9,296,984 B2 | 3/2016 | Cimino et al. |
| 9,581,942 B1 | 2/2017 | Shippert |
| D799,262 S | 10/2017 | Feng |
| 9,907,883 B2 | 3/2018 | Llull et al. |
| 9,909,094 B2 | 3/2018 | Cimino et al. |
| 9,909,095 B2 | 3/2018 | Cimino et al. |
| 10,138,457 B2 | 11/2018 | Cimino et al. |
| 10,286,122 B2 | 5/2019 | Locke et al. |
| 10,300,183 B2 | 5/2019 | Park et al. |
| D851,777 S | 6/2019 | Barere et al. |
| 10,314,955 B2 | 6/2019 | Friedman et al. |
| 10,472,603 B2 | 11/2019 | Friedman et al. |
| 10,549,018 B2 | 2/2020 | Park et al. |
| D889,680 S | 7/2020 | Barere et al. |
| 10,772,997 B2 | 9/2020 | Shippert |
| D921,216 S | 6/2021 | Barere et al. |
| 11,091,733 B2 | 8/2021 | Friedman et al. |
| 11,261,418 B2 | 3/2022 | Cimino et al. |
| 2001/0030152 A1 | 10/2001 | Wright et al. |
| 2001/0033834 A1 | 10/2001 | Wilkison et al. |
| 2002/0076400 A1 | 6/2002 | Katz et al. |
| 2002/0188280 A1 | 12/2002 | Nguyen et al. |
| 2003/0082152 A1 | 5/2003 | Hedrick et al. |
| 2003/0161816 A1 | 8/2003 | Fraser et al. |
| 2003/0161817 A1 | 8/2003 | Young et al. |
| 2003/0211602 A1 | 11/2003 | Atala |
| 2004/0005246 A1 | 1/2004 | Efthimiadis et al. |
| 2004/0067218 A1 | 4/2004 | Casteilla et al. |
| 2004/0097867 A1 | 5/2004 | Fraser et al. |
| 2004/0171146 A1 | 9/2004 | Katz et al. |
| 2005/0048034 A1 | 3/2005 | Fraser et al. |
| 2005/0076396 A1 | 4/2005 | Katz et al. |
| 2005/0084961 A1 | 4/2005 | Hedrick et al. |
| 2005/0131335 A1 | 6/2005 | Drott et al. |
| 2005/0153442 A1 | 7/2005 | Katz et al. |
| 2005/0282275 A1 | 12/2005 | Katz et al. |
| 2006/0051865 A1 | 3/2006 | Higgins et al. |
| 2006/0184119 A1 | 8/2006 | Remde et al. |
| 2006/0224144 A1 | 10/2006 | Lee |
| 2006/0240546 A1 | 10/2006 | Goodwin et al. |
| 2007/0089103 A1 | 4/2007 | Iborra et al. |
| 2007/0106208 A1 | 5/2007 | Uber et al. |
| 2007/0225665 A1 | 9/2007 | Perez-Cruet et al. |
| 2007/0248575 A1 | 10/2007 | Connor et al. |
| 2008/0014181 A1 | 1/2008 | Ariff et al. |
| 2008/0050275 A1 | 2/2008 | Bischof et al. |
| 2008/0319417 A1 | 12/2008 | Quijano et al. |
| 2009/0042267 A1 | 2/2009 | Park |
| 2009/0181104 A1 | 7/2009 | Rigotti et al. |
| 2009/0287190 A1 | 11/2009 | Shippert |
| 2009/0299328 A1 | 12/2009 | Mudd et al. |
| 2010/0055087 A1 | 3/2010 | Higgins et al. |
| 2010/0174162 A1 | 7/2010 | Gough et al. |
| 2010/0268189 A1 | 10/2010 | Byrnes et al. |
| 2010/0279405 A1 | 11/2010 | Peterson et al. |
| 2010/0285521 A1 | 11/2010 | Vossman et al. |
| 2010/0285588 A1 | 11/2010 | Stubbers et al. |
| 2011/0009822 A1 | 1/2011 | Nielsen |
| 2011/0117650 A1 | 5/2011 | Riordan |
| 2011/0145653 A1 | 6/2011 | Broadfoot et al. |
| 2011/0198353 A1 | 8/2011 | Tsao |
| 2012/0003733 A1 | 1/2012 | Gueneron |
| 2012/0214659 A1 | 8/2012 | Do et al. |
| 2013/0131635 A1 | 5/2013 | Rimsa et al. |
| 2013/0150825 A1 | 6/2013 | Rimsa et al. |
| 2013/0158515 A1 | 6/2013 | Austen, Jr. |
| 2013/0324966 A1* | 12/2013 | Park .................... A61M 1/895 210/450 |
| 2014/0363891 A1 | 12/2014 | Llull et al. |
| 2015/0118752 A1 | 4/2015 | Cimino et al. |
| 2015/0276070 A1 | 10/2015 | Yokoe et al. |
| 2016/0030486 A1 | 2/2016 | Cimino et al. |
| 2016/0208211 A1* | 7/2016 | Cimino .................. C12M 47/04 |
| 2017/0304823 A1 | 10/2017 | Sparks et al. |
| 2017/0363216 A1 | 12/2017 | Schmitt et al. |
| 2019/0224386 A1 | 7/2019 | Locke et al. |
| 2019/0247557 A1 | 8/2019 | Friedman et al. |
| 2020/0129681 A1 | 4/2020 | Park et al. |
| 2020/0182757 A1 | 6/2020 | Hamstrom et al. |

FOREIGN PATENT DOCUMENTS

| | | |
|---|---|---|
| EP | 0512769 A2 | 11/1992 |
| EP | 1106191 A1 | 6/2001 |
| EP | 1310267 A2 | 5/2003 |
| JP | 59-26642 U | 2/1984 |
| JP | 5-7622 A | 1/1993 |
| JP | 8-98882 A | 4/1996 |
| JP | 10-108829 A | 4/1998 |
| JP | 2001-252353 A | 9/2001 |
| JP | 2009-189282 A | 8/2009 |
| JP | 2011-12581 A | 1/2011 |
| JP | 2011-125813 A | 6/2011 |
| JP | 2011-524191 A | 9/2011 |
| JP | 3172209 U | 12/2011 |
| JP | 2013-507983 A | 3/2013 |
| JP | 2013-526990 A | 6/2013 |
| WO | 1995/09051 A1 | 4/1995 |
| WO | 2003/053346 A2 | 7/2003 |
| WO | 2008/137234 A1 | 11/2008 |
| WO | 2009/055610 A1 | 4/2009 |
| WO | 2009/149250 A1 | 12/2009 |
| WO | 2011/052946 A2 | 5/2011 |
| WO | 2012/006587 A2 | 1/2012 |
| WO | 2012/019103 A2 | 2/2012 |
| WO | 2012/083412 A1 | 6/2012 |
| WO | 2012/109603 A1 | 8/2012 |
| WO | 2012/116100 A1 | 8/2012 |
| WO | 2012/139593 A2 | 10/2012 |
| WO | 2013/090579 A1 | 6/2013 |
| WO | 2013/106655 A1 | 7/2013 |
| WO | 2014/039697 A1 | 3/2014 |
| WO | 2014/110448 A1 | 7/2014 |
| WO | 2015/035221 A1 | 3/2015 |
| WO | 2018/044791 A1 | 3/2018 |

OTHER PUBLICATIONS

U.S. Appl. No. 15/013,111, filed Feb. 2, 2016, U.S. Pat. No. 10,300,183, Issued.

U.S. Appl. No. 16/379,021, filed Apr. 9, 2019, U.S. Pat. No. 10,549,018, Issued.

U.S. Appl. No. 16/732,538, filed Jan. 2, 2020, 2020-0129681, Published.

U.S. Appl. No. 15/688,387, filed Aug. 28, 2017, U.S. Pat. No. 10,472,603, Issued.

U.S. Appl. No. 16/585,965, filed Sep. 27, 2019, U.S. Pat. No. 11,091,733, Issued.

U.S. Appl. No. 15/331,117, filed Oct. 21, 2016, U.S. Pat. No. 10,314,955, Issued.

U.S. Appl. No. 16/393,421, filed Apr. 24, 2019, 2019-0247557, Abandoned.

U.S. Appl. No. 29/592,336, filed Jan. 30, 2017, D851777, Issued.

U.S. Appl. No. 29/688,879, filed Apr. 25, 2019, D889680, Issued.

U.S. Appl. No. 29/734,645, filed May 14, 2020, D921216, Issued.

U.S. Appl. No. 16/710,671, filed Dec. 11, 2019, 2020-0182757, Published.

(56) References Cited

OTHER PUBLICATIONS

U.S. Appl. No. 16/193,004, filed Nov. 16, 2018, U.S. Pat. No. 11,261,418, Issued.
U.S. Appl. No. 17/580,865, filed Jan. 21, 2022, Pending.
Coleman et al., Fat grafting to the breast revisited: safety and efficacy. Plast Reconstr Surg. Mar. 2007;119(3):775-85.
Delay et al., Fat injection to the breast: technique, results, and indications based on 880 procedures over 10 years. Aesthet Surg J. Sep.-Oct. 2009;29(5):360-76.
LifeCell Corporation, USA Revolve™ System—Materials. Instructions for use. 2 pages (2014).
Pakhomov et al., Hydraulically coupled microejection technique for precise local solution delivery in tissues. J Neurosci Methods. Sep. 15, 2006;155(2):231-40.
Smith et al., Autologous human fat grafting: effect of harvesting and preparation techniques on adipocyte graft survival. Plast Reconstr Surg. May 2006;117(6):1836-44.
Yoshimura et al., Cell-assisted lipotransfer for cosmetic breast augmentation: supportive use of adipose-derived stem/stromal cells. Aesthetic Plast Surg. Jan. 2008;32(1):48-55.
International Preliminary Report on Patentability for Application No. PCT/US2013/041111, dated Dec. 11, 2014.
International Search Report and Written Opinion for Application No. PCT/US2016/058171, dated Apr. 25, 2017. 14 pages.
International Search Report and Written Opinion for Application No. PCT/US2017/048898, dated Dec. 6, 2017. 13 pages.

\* cited by examiner

| INPUTS | LIPOSUCTION | HOLD AND MIX | IRRIGATION | VACUUM / CLEAR |
|---|---|---|---|---|
| LIPOSUCTION CANNULA | OPEN | CLOSED | CLOSED | CLOSED |
| IRRIGATION TUBE | CLOSED | CLOSED | OPEN | CLOSED |
| VACUUM TUBE | OPEN | CLOSED | CLOSED | OPEN |
| VENT | CLOSED | CLOSED | OPEN | OPEN |

*FIG. 4*

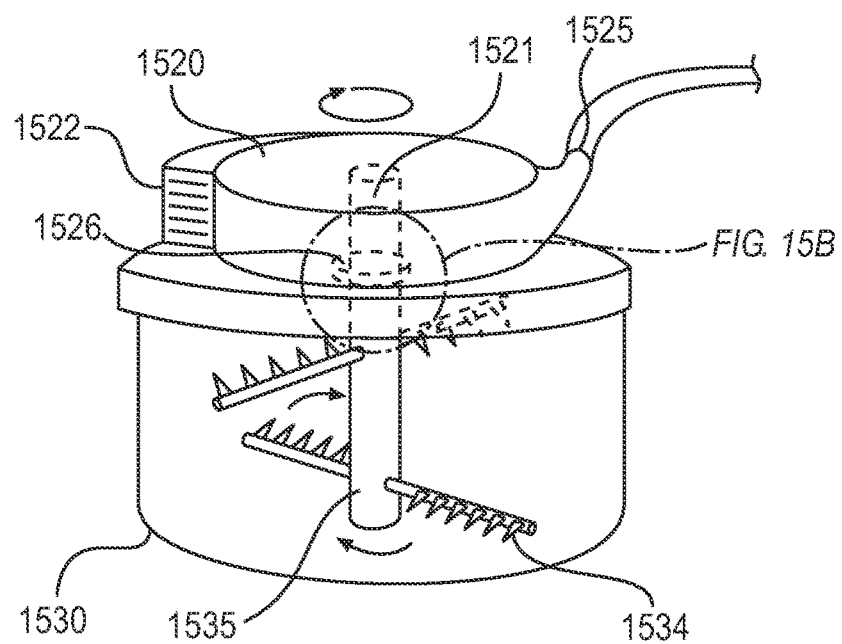
FIG. 15A
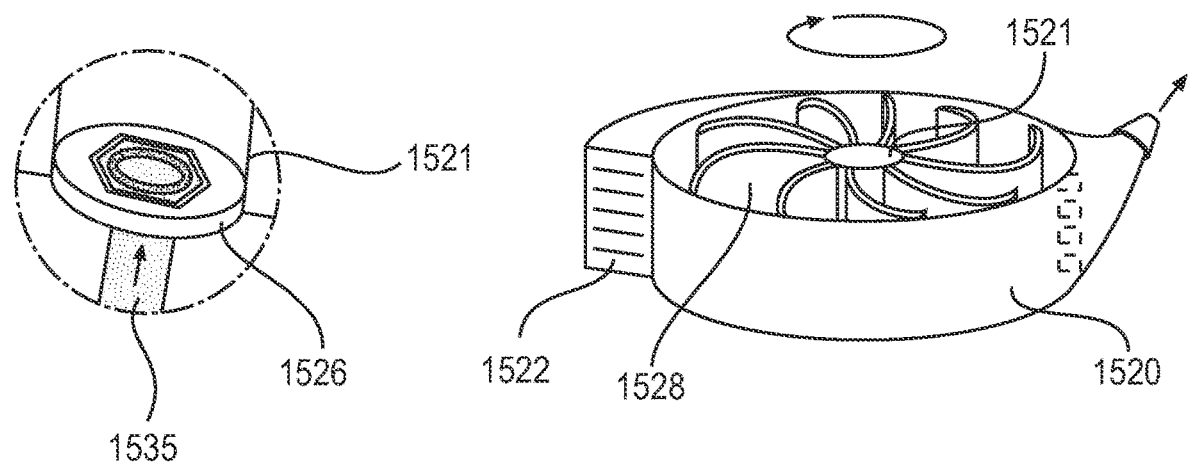
FIG. 15B  FIG. 15C

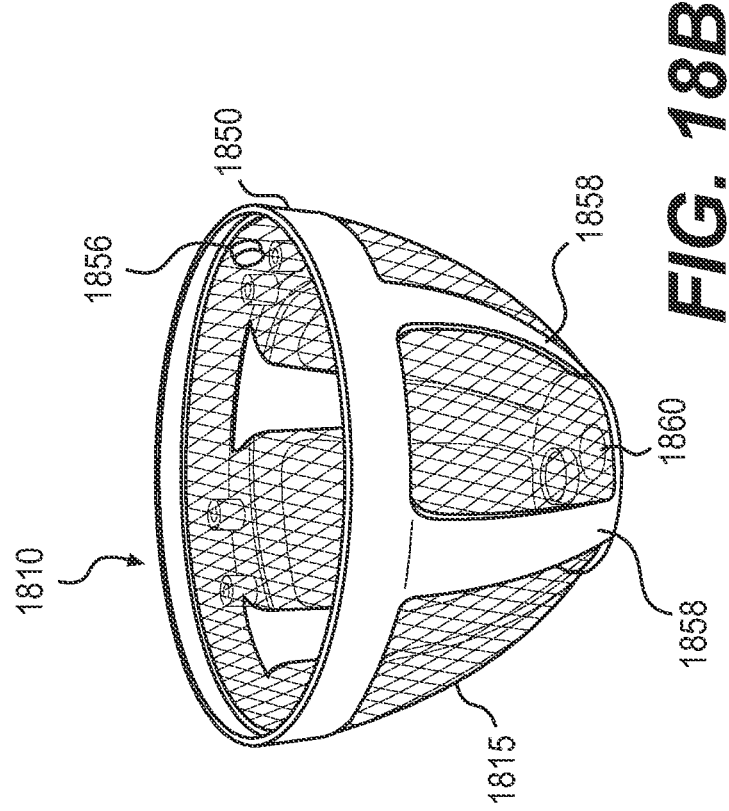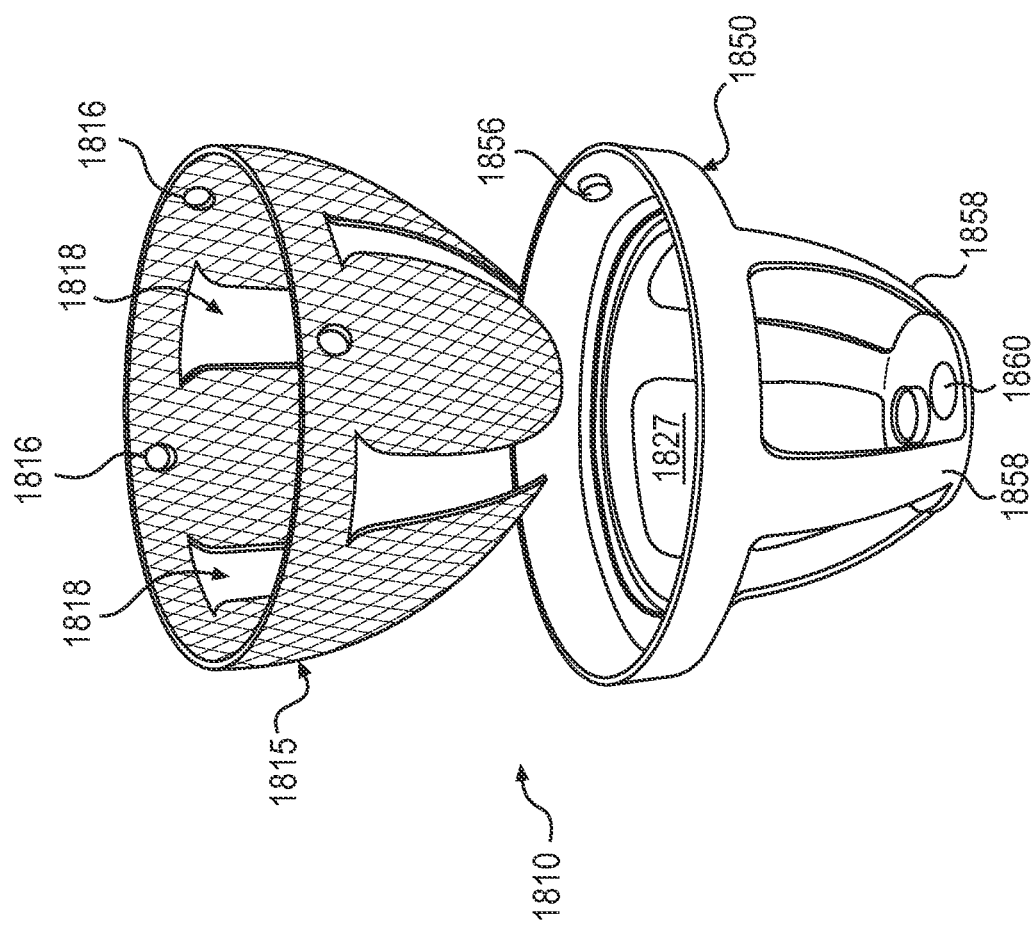

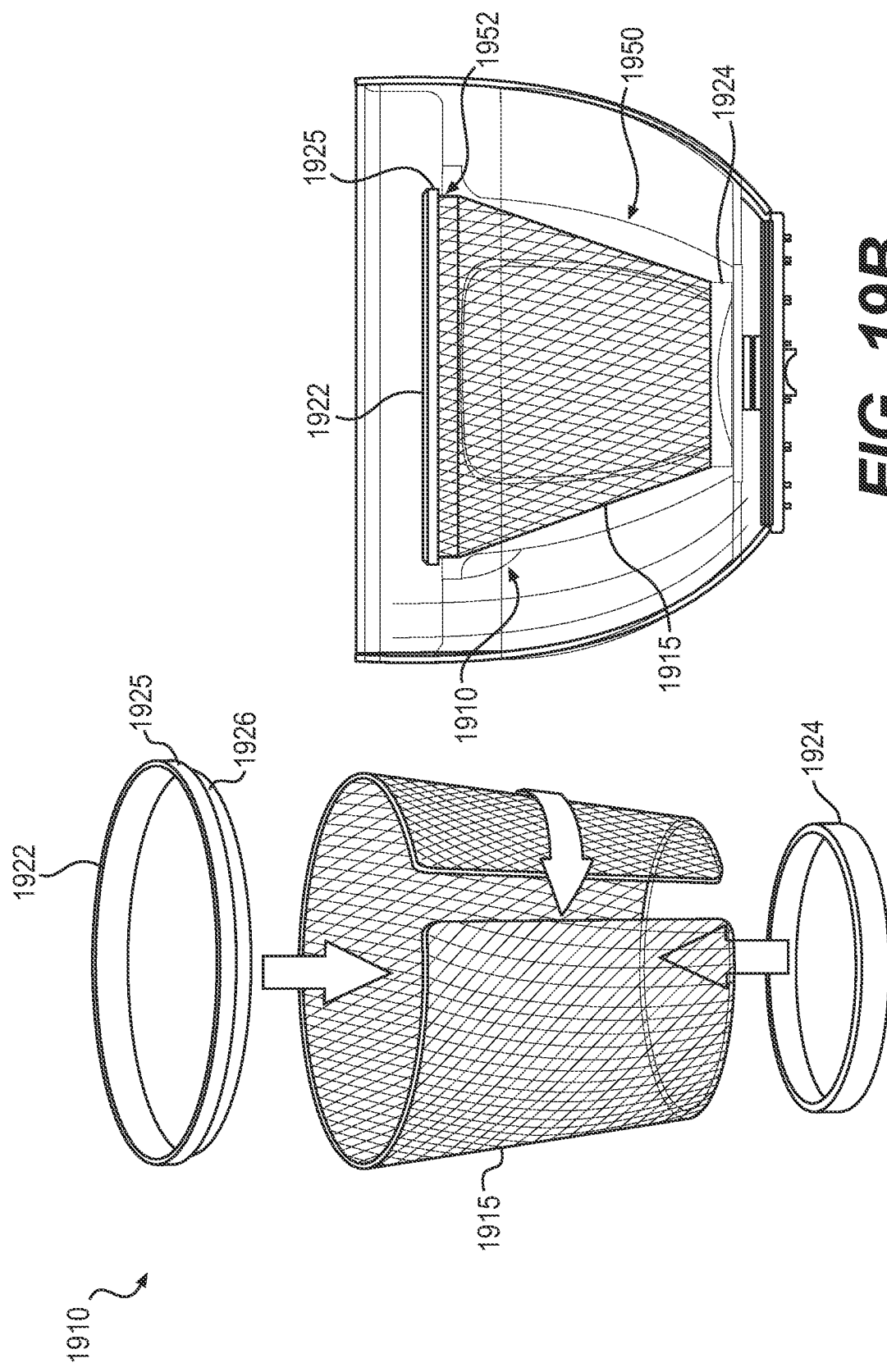

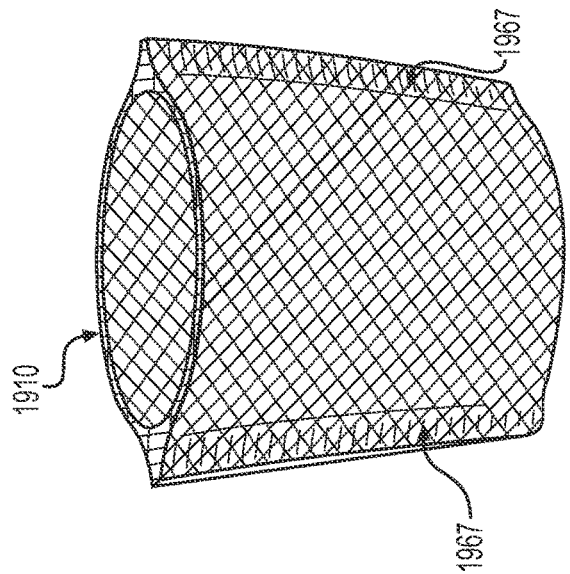
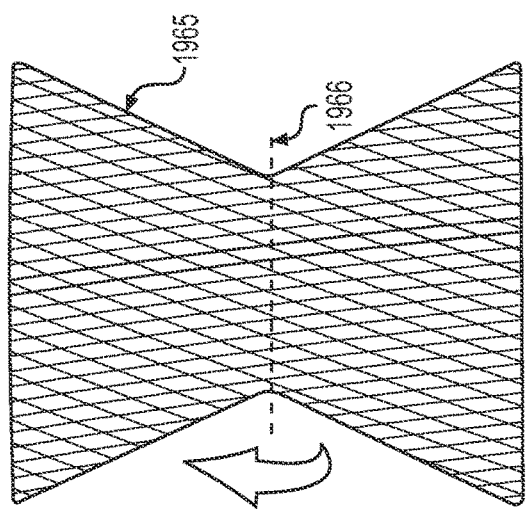
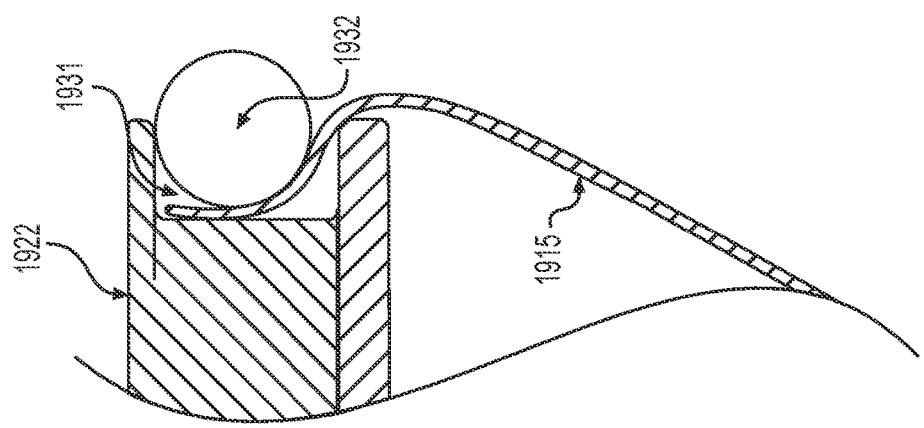
FIG. 19E
FIG. 19D
FIG. 19C

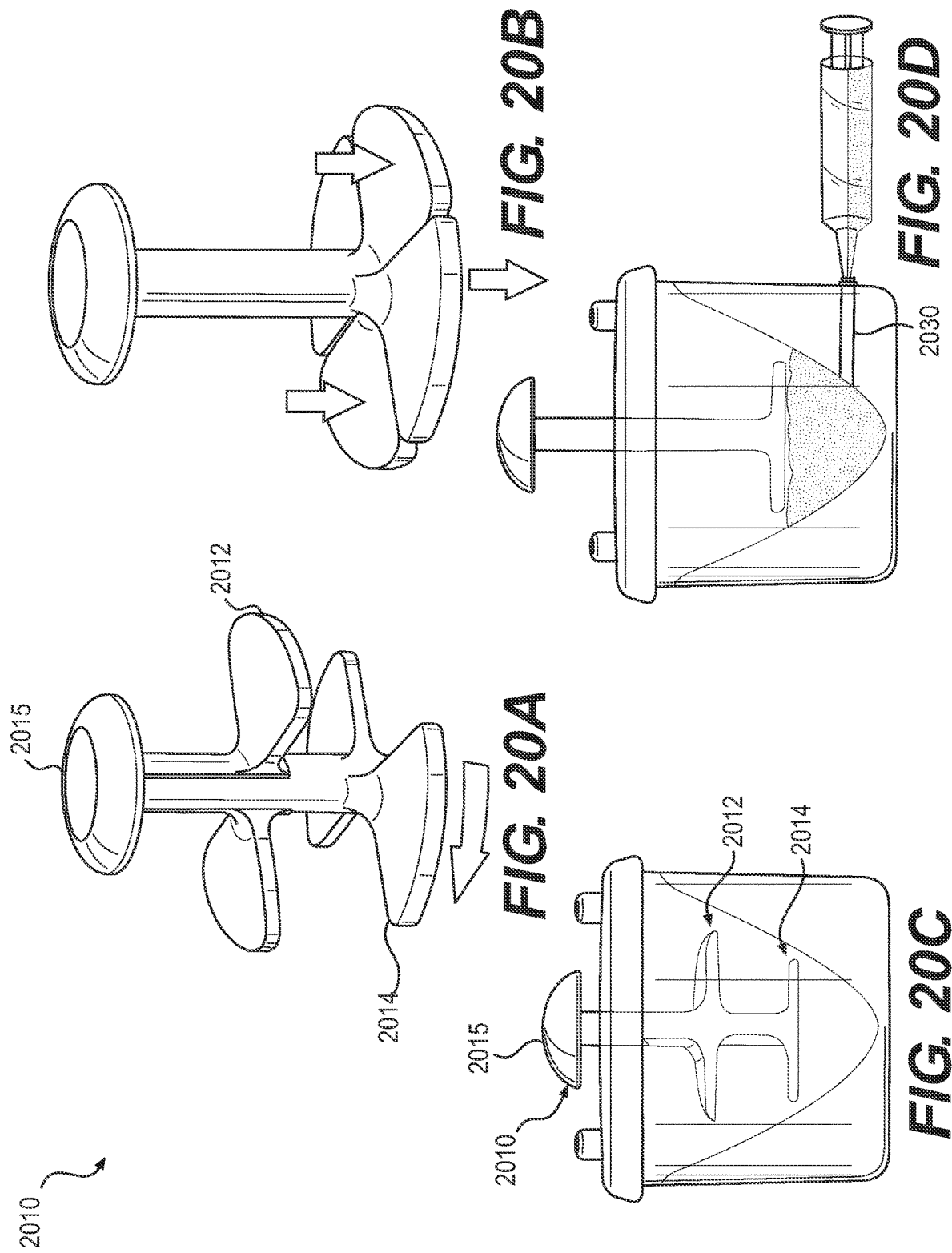

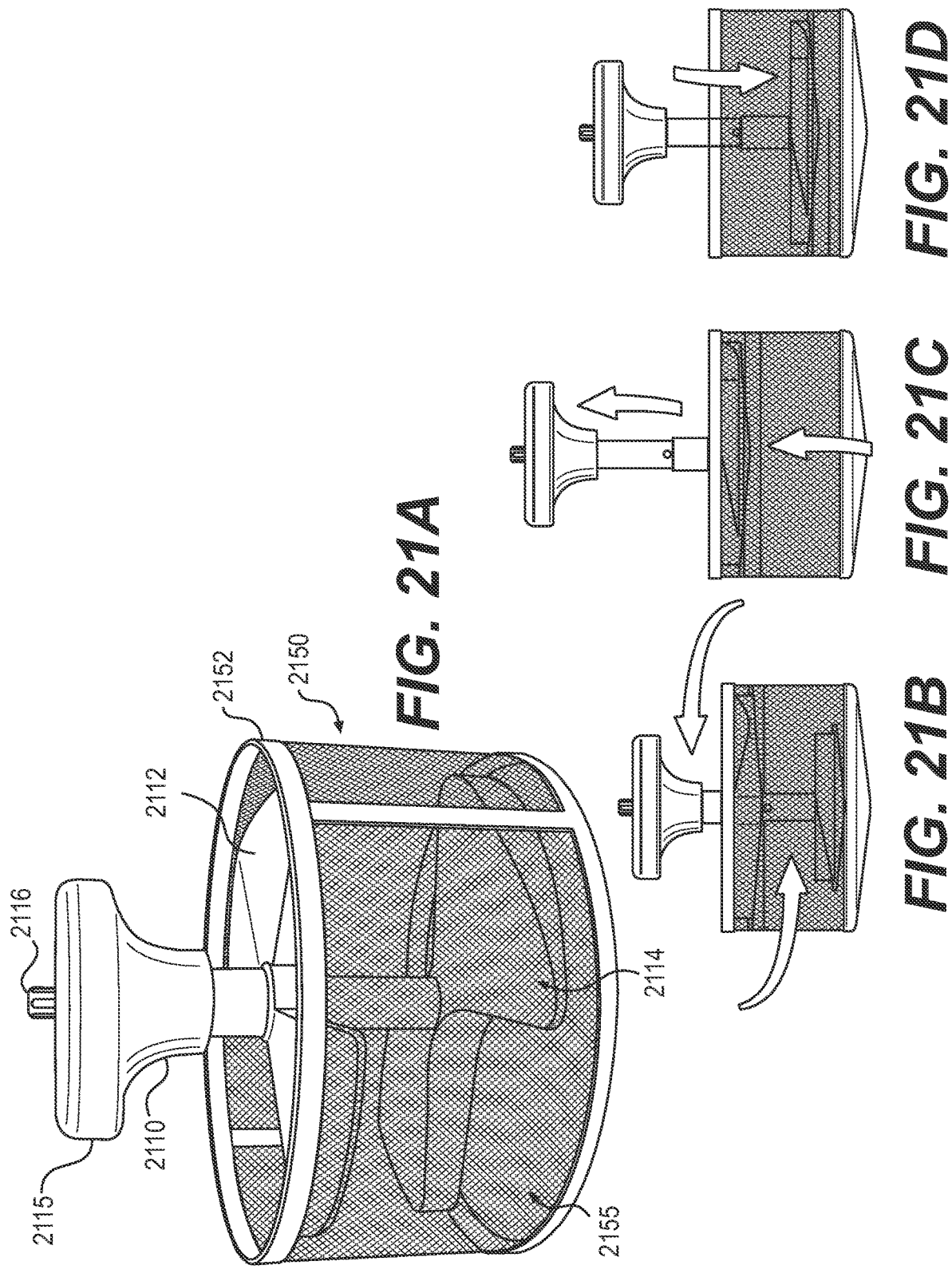

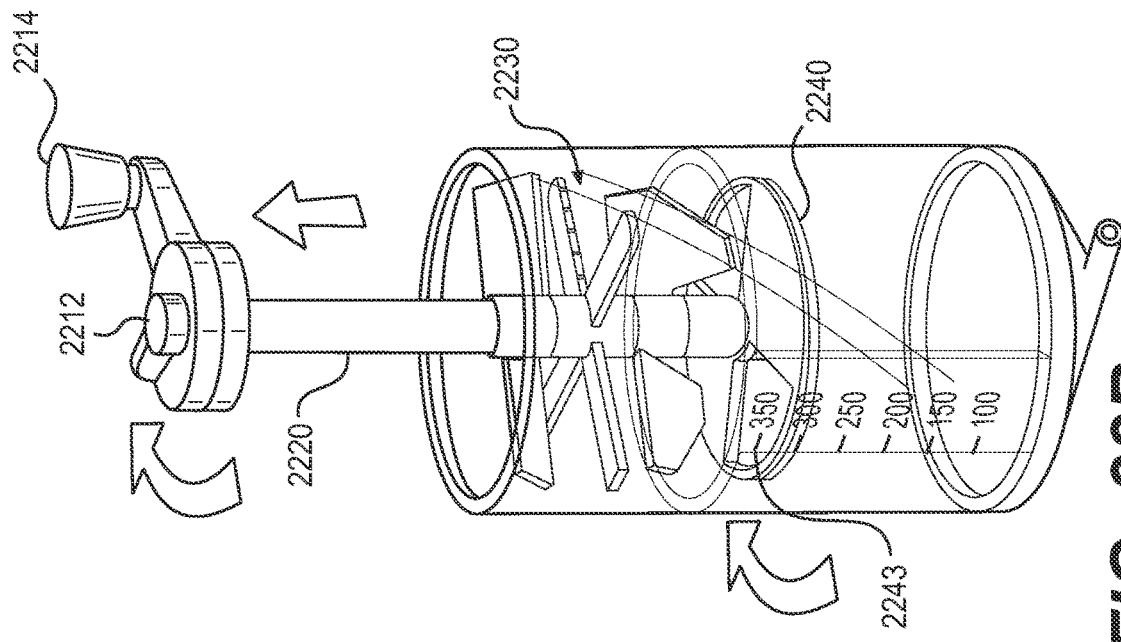
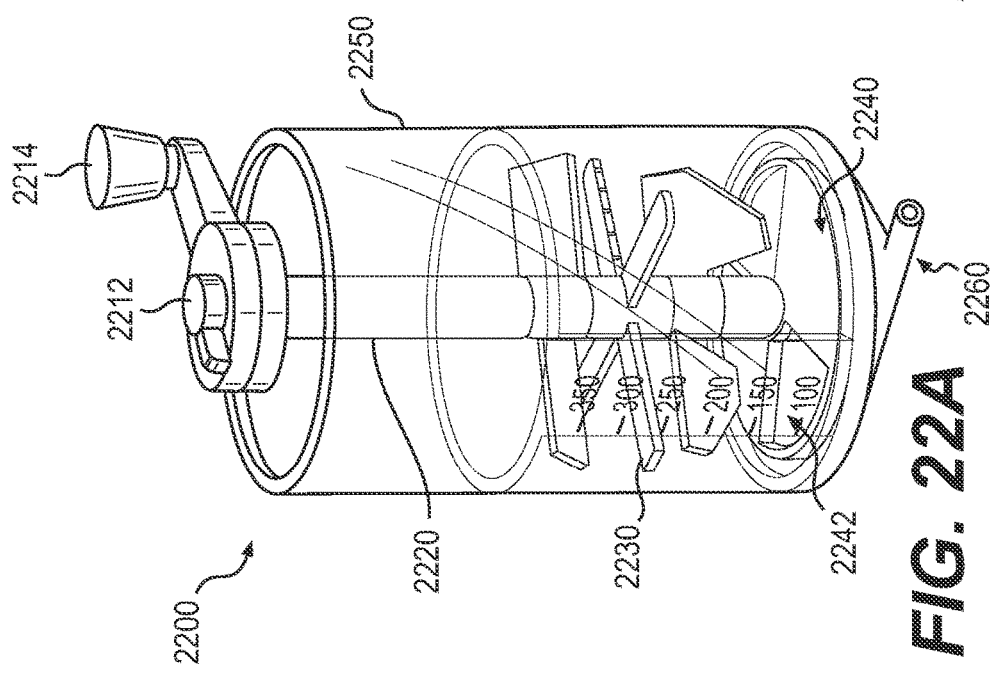

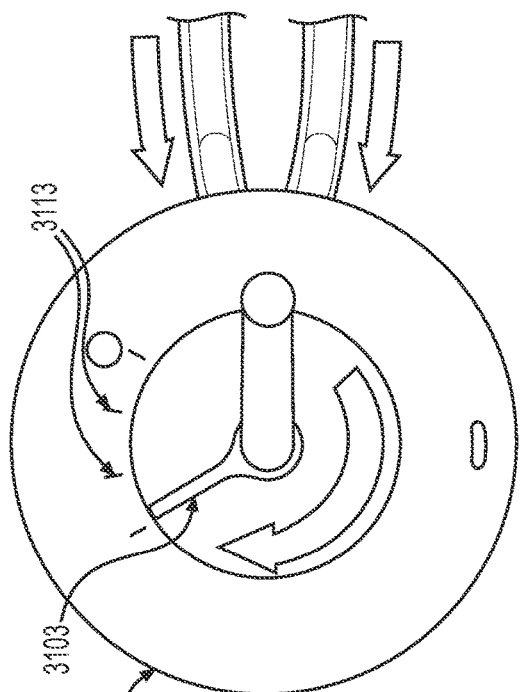
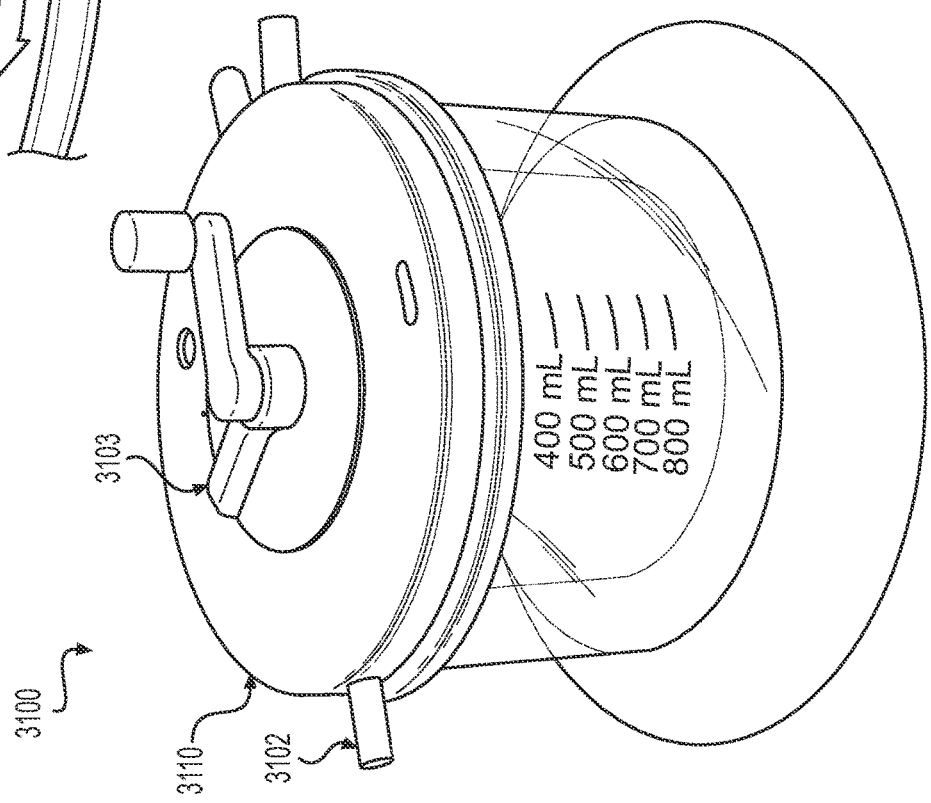
FIG. 31B
FIG. 31A

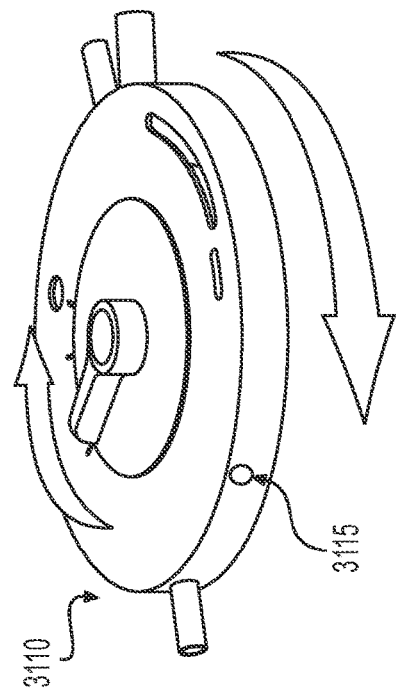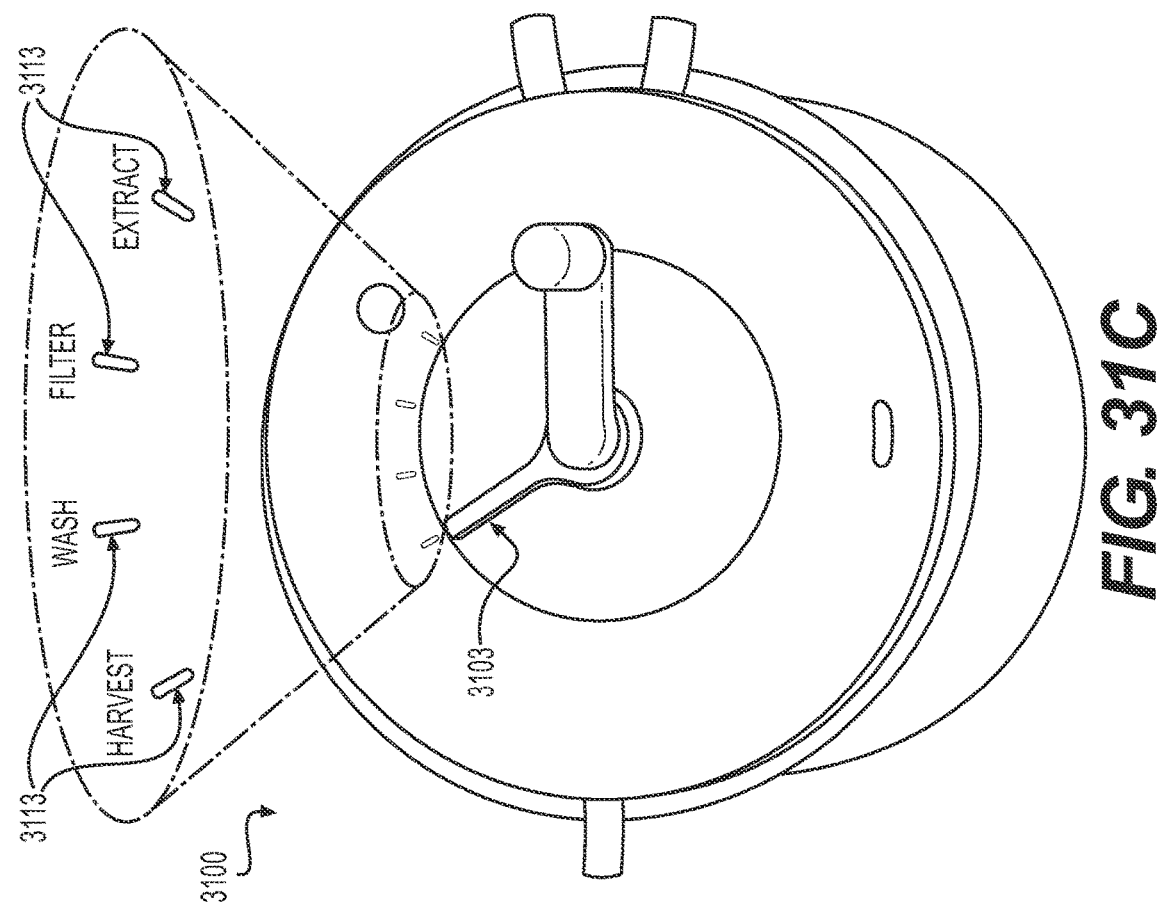

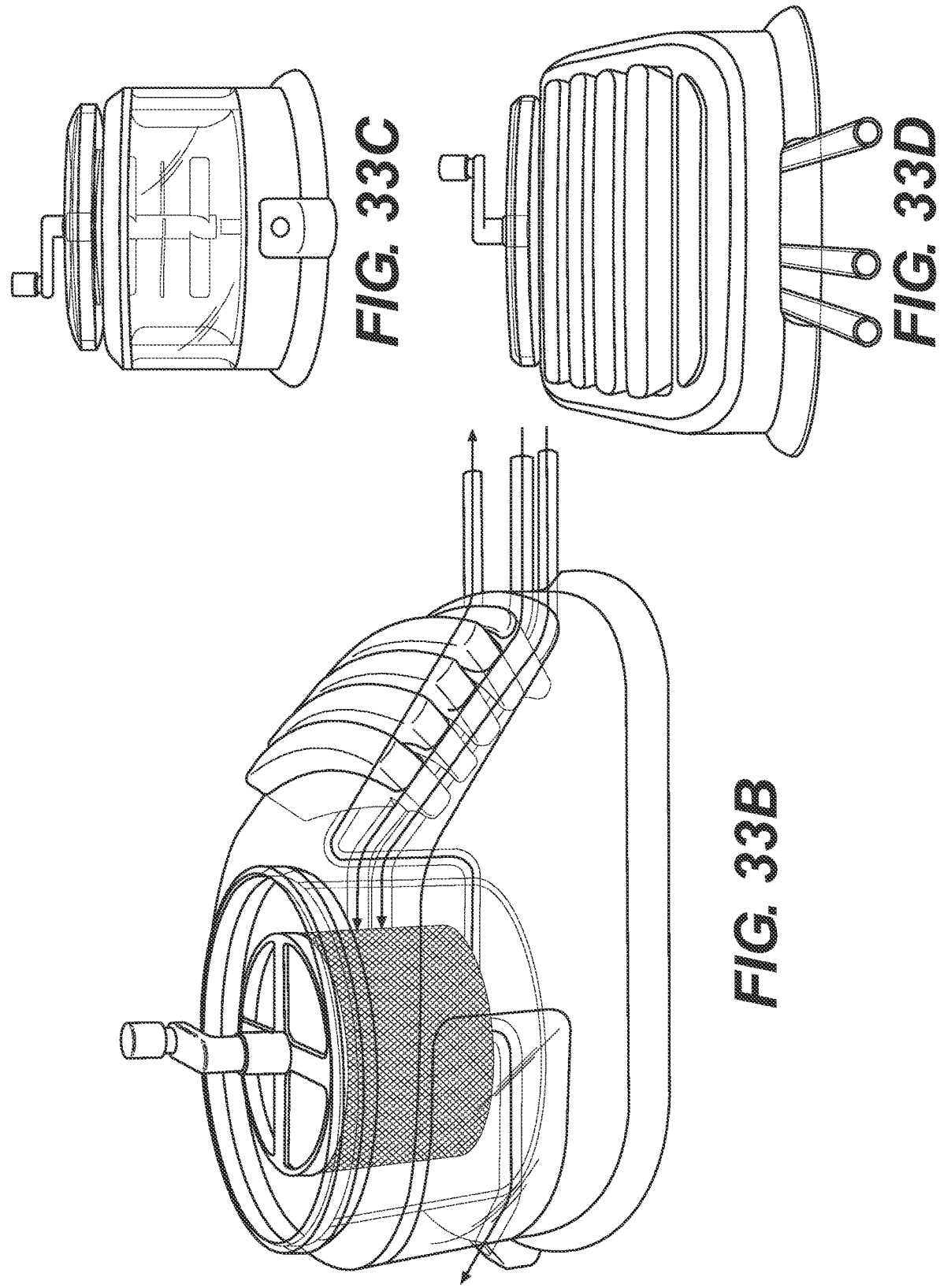

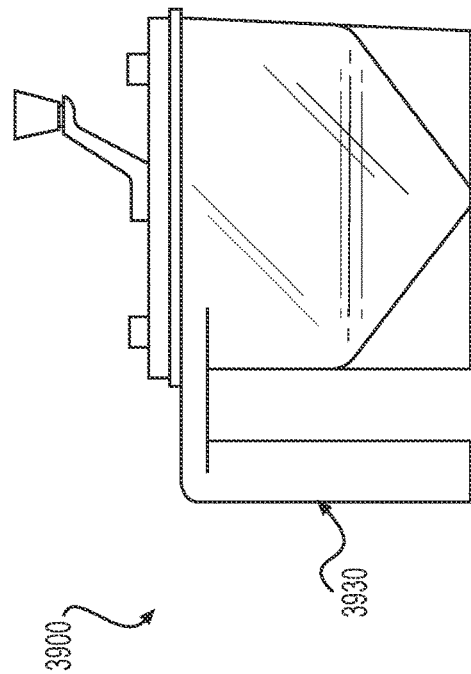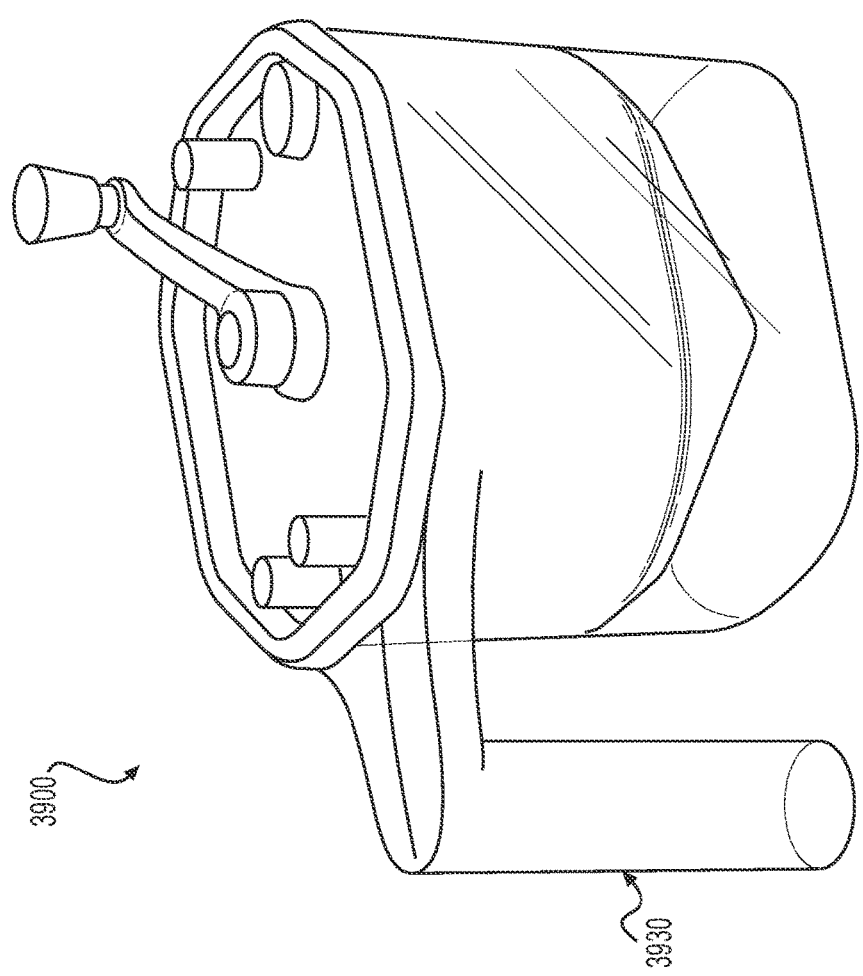

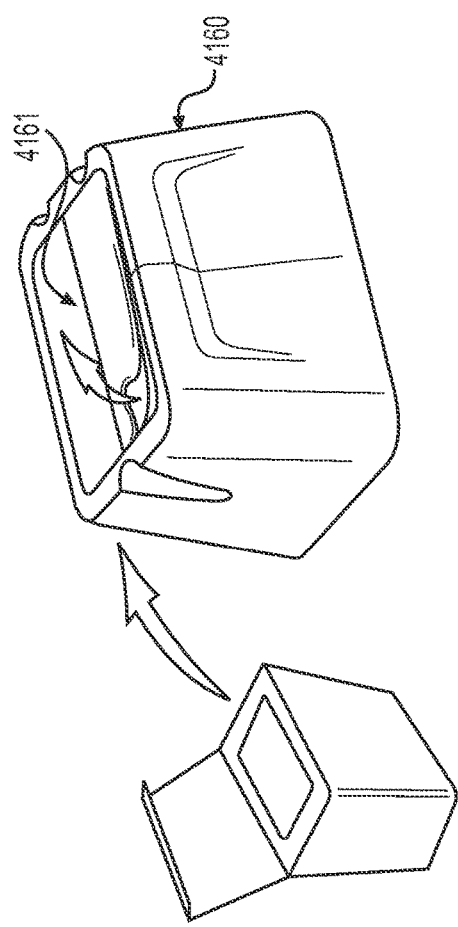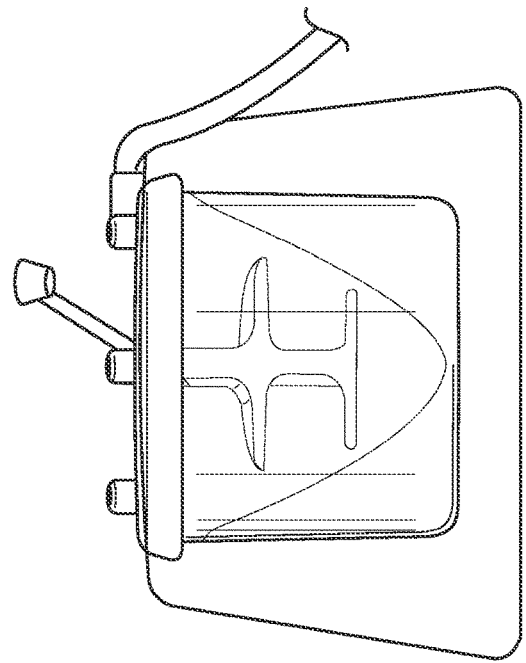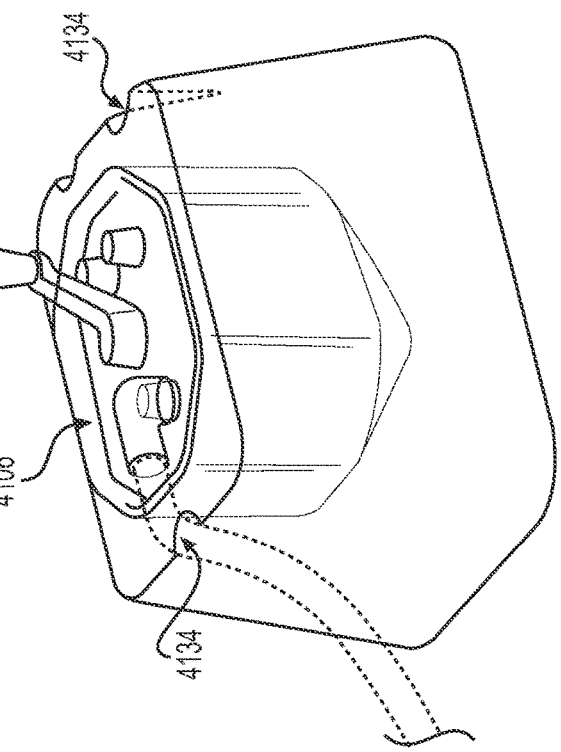
FIG. 41A
FIG. 41B
FIG. 41C

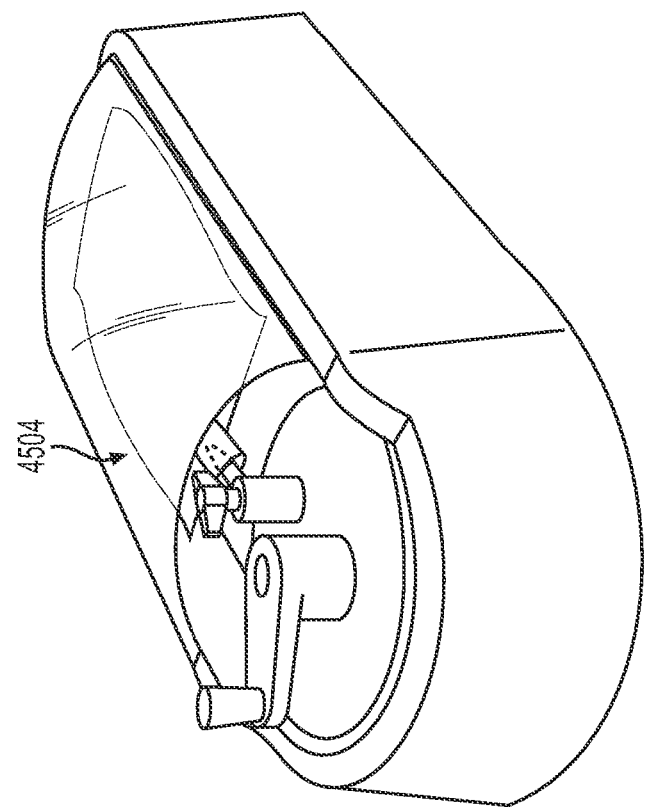
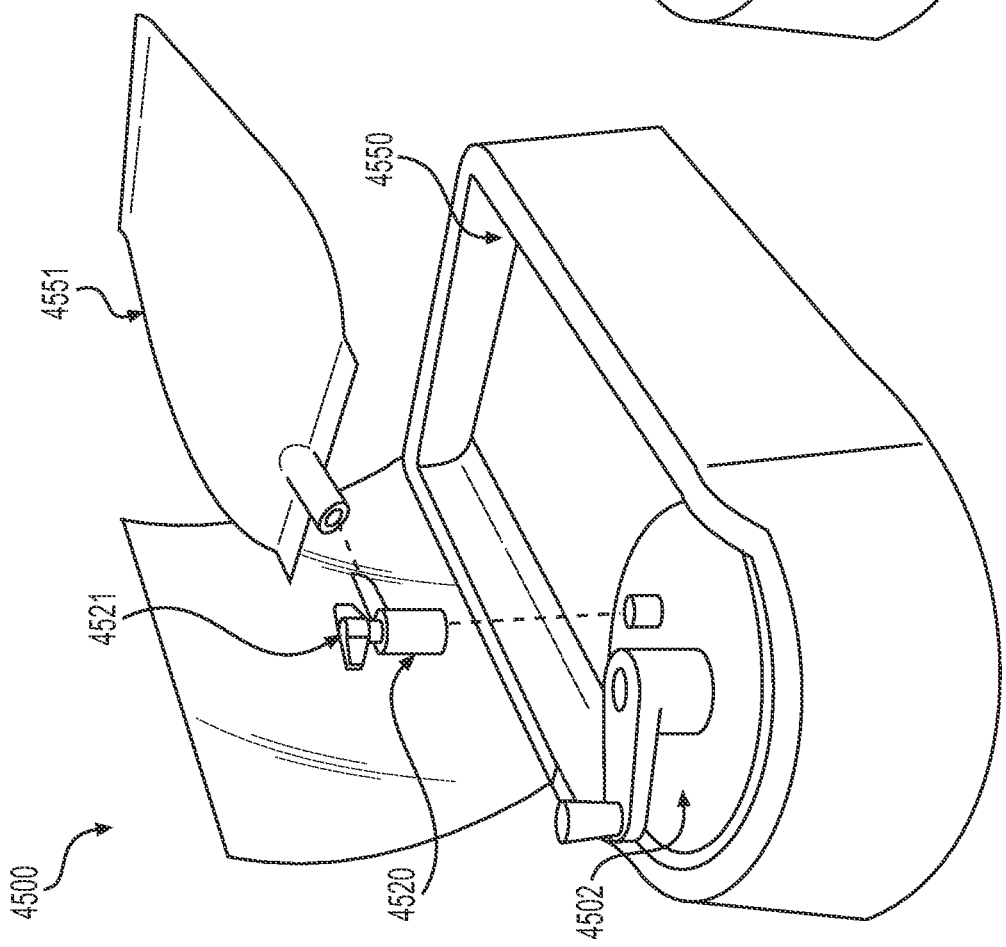

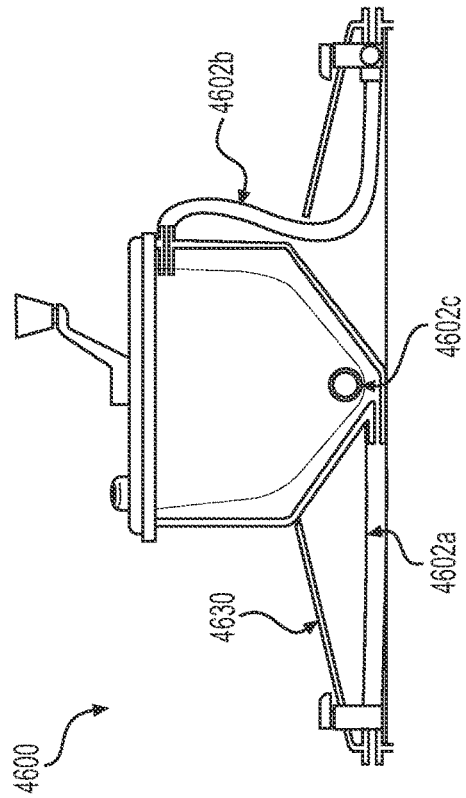
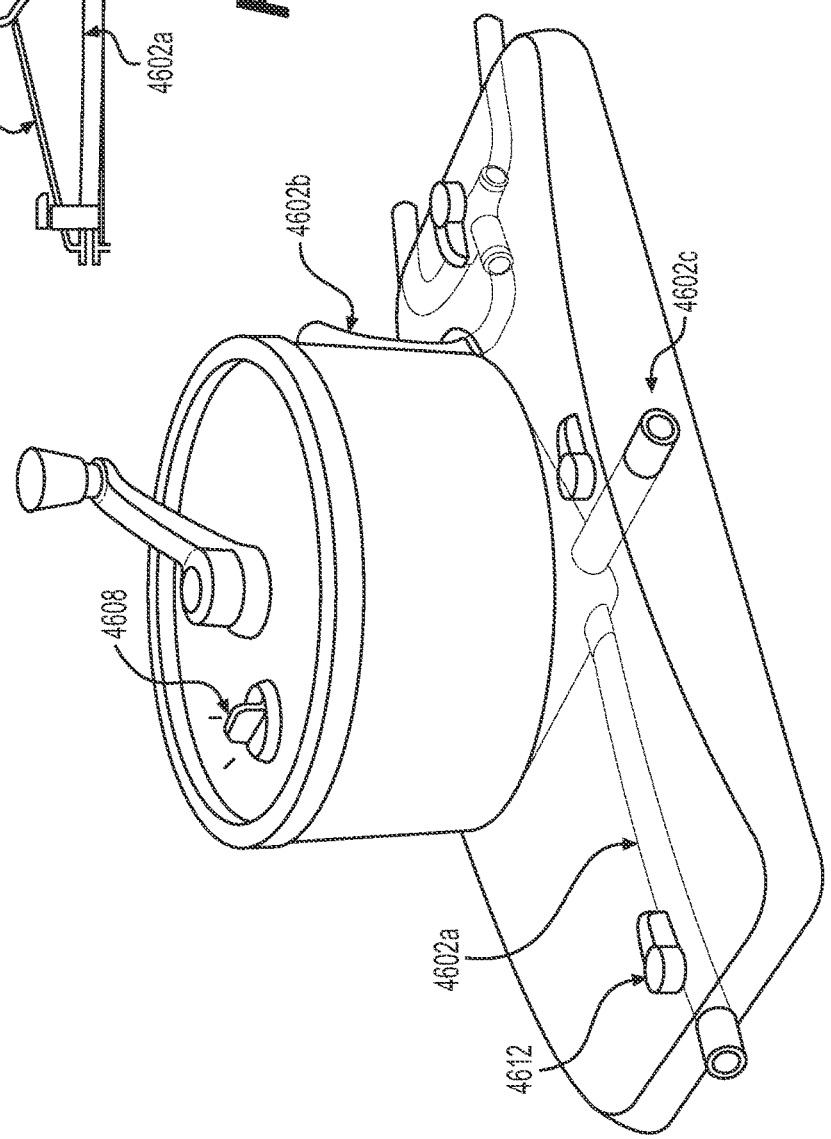

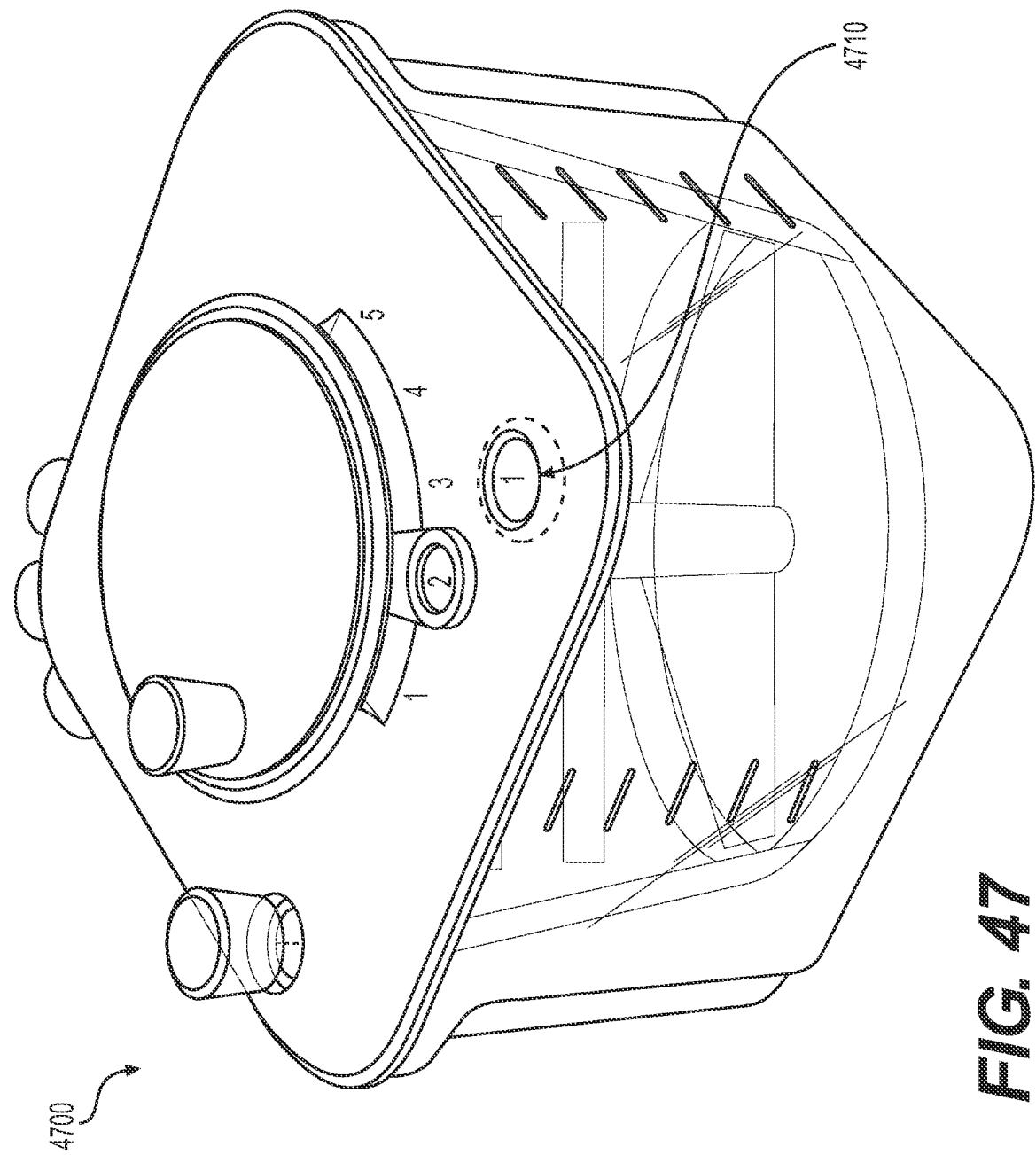

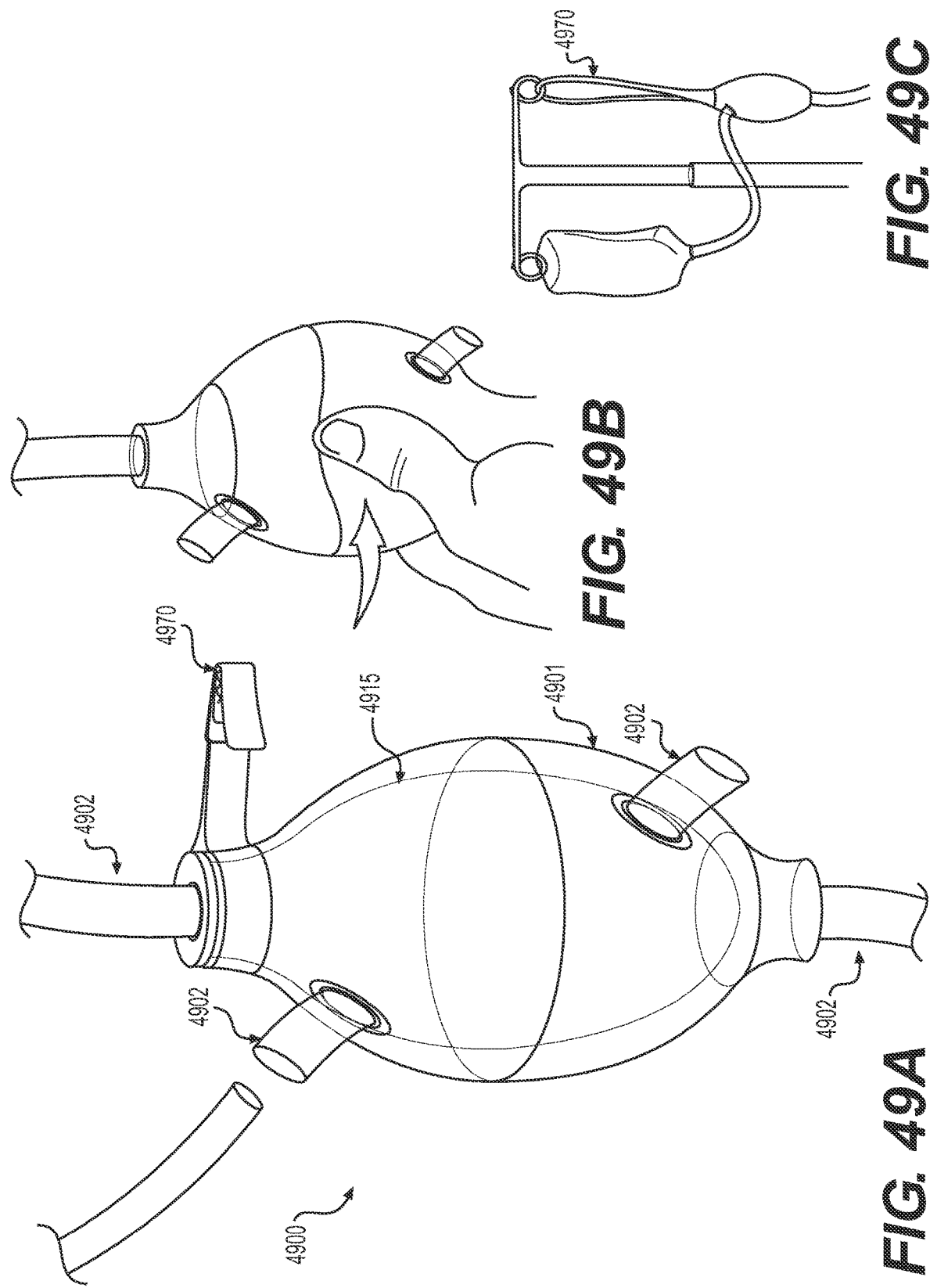

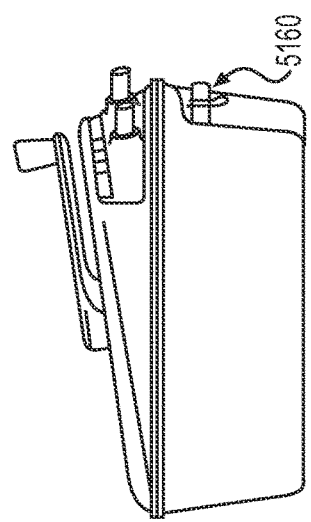
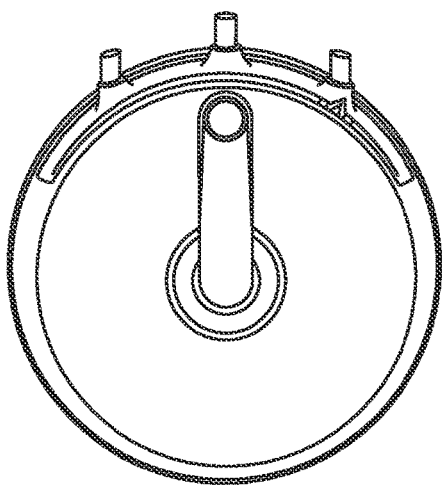
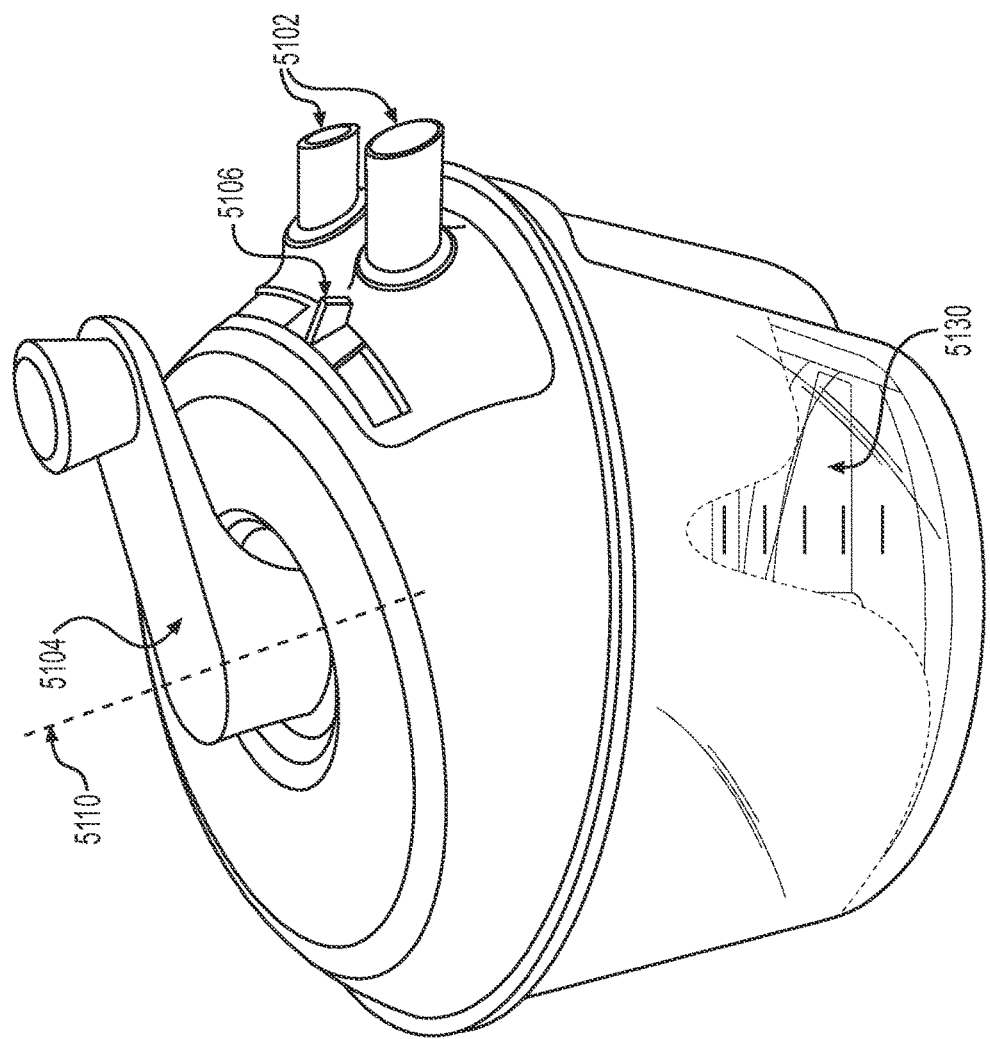

SYSTEMS AND METHODS FOR MEDICAL DEVICE CONTROL

This application is a continuation of U.S. patent application Ser. No. 16/585,965, filed Sep. 27, 2019, which is a continuation of U.S. patent application Ser. No. 15/688,387, filed Aug. 28, 2017 and now U.S. Pat. No. 10,472,603, which claims priority to U.S. Provisional Patent Application 62/381,118, filed Aug. 30, 2016, each of the above applications being incorporated herein by reference in its entirety.

The present application relates to systems and methods for control of fluid delivery to and from a medical device, including devices for tissue processing and cleaning.

Some surgical procedures require use of tubes, hoses, or other conduits to transfer fluids, gases, and/or tissue products between a patient and a treatment system or device, or among systems and devices. Some surgical procedures are multi-step processes requiring connection and disconnection of hoses from input and output ports. For example, using some adipose tissue transfer systems, surgical personnel may need to perform over one hundred combined user actions and decisions. Some of these user actions involve enabling and disabling a vacuum source or adding or removing tissue or washing solutions to a tissue storage and treatment container.

Keeping track of the state of tube connections in some surgical procedures creates a burden on the practitioner. The user effort needed to manage the tube connections is not negligible and can increase the total time to perform procedures. Although organizational technologies such as color-coding exist, they cannot eliminate the burden of needing to assess the state of each individual tube at multiple points throughout a procedure.

In an embodiment of the present invention, a tissue treatment system includes a container and a flow management device. The container includes an exterior wall surrounding an interior volume for holding tissue. The container also includes a filter structure for processing tissue. The flow management device includes a first plate having a plurality of first openings passing therethrough. The flow management device also includes a second plate having a plurality of second openings passing therethrough. The flow management device also includes a third plate having one or more third openings passing therethrough. The first plate, second plate, and third plate are operably connected. Setting the third plate in a first position places a first subset of the plurality of first openings in fluid communication with a first subset of the plurality of second openings. Setting the third plate in a second position places a second subset of the plurality of first openings in fluid communication with a second subset of the plurality of second openings. Setting the third plate to a third position places a third subset of the plurality of first openings in fluid communication with a third subset of the plurality of second openings.

In an embodiment of the present invention, a flow management device includes a first plate having a plurality of first openings passing therethrough. The flow management device also includes a second plate having a plurality of second openings passing therethrough. The flow management device also includes a third plate having one or more third openings passing therethrough. The first plate, second plate, and third plate are operably connected. Setting the third plate in a first position places a first subset of the plurality of first openings in fluid communication with a first subset of the plurality of second openings. Setting the third plate in a second position places a second subset of the plurality of first openings in fluid communication with a second subset of the plurality of second openings. Setting the third plate to a third position places a third subset of the plurality of first openings in fluid communication with a third subset of the plurality of second openings.

In an embodiment of the present invention, a tissue treatment system includes a container and a tube management device. The container includes an exterior wall surrounding an interior volume for holding tissue and a filter structure for processing tissue. The tube management device includes a tube restrictor plate having a plurality of tube through-holes and a tube stabilizer plate having a plurality of tube through-holes. A plurality of flow-restricting devices is disposed on the tube restrictor plate adjacent to the plurality of tube through-holes. The tube management device further includes a multi-position switch. A plurality of tubes passes through the tube through-holes. Moreover, setting the multi-position switch to a first position causes the plurality of flow-restricting devices to restrict the flow in a first subset of the plurality of tubes to transfer tissue from a patient to the interior volume, setting the multi-position switch to a second position causes the plurality of flow-restricting devices to restrict the flow in a second subset of the plurality of tubes to allow processing of the tissue in the interior volume, and setting the multi-position switch to a third position causes the plurality of flow-restricting devices to restrict the flow in a third subset of the plurality of tubes to allow transfer of the tissue out of the interior volume.

In an embodiment of the present invention, a method of managing surgical conduits is described. The method includes providing a plurality of tubes and a plurality of flow-restricting devices within a device body, each of the flow-restricting devices proximal to at least one of the plurality of tubes. The method also includes providing a multi-position switch wherein flow in a first subset of the plurality of tubes is restricted by the plurality of flow-restricting devices when the multi-position switch is in a first position and flow in a second subset of the plurality of tubes different than the first subset is restricted by the plurality of flow-restricting devices when the multi-position switch is in a second position. The method also includes switching from the first position of the multi-position switch to the second position of the multi-position switch.

In an embodiment of the present invention, a tube management device includes a tube restrictor plate having a plurality of tube through-holes and a tube stabilizer plate having a plurality of tube through-holes. A plurality of flow-restricting devices is disposed on the tube restrictor plate adjacent to the plurality of tube through-holes. The tube management device also includes a multi-position switch and a plurality of tubes that pass through the plurality of tube through-holes. Setting the multi-position switch of the tube management device to a first position causes the plurality of flow-restricting devices to restrict the flow in a first subset of the plurality of tubes, setting the multi-position switch to a second position causes the plurality of flow-restricting devices to restrict the flow in a second subset of the plurality of tubes, and setting the multi-position switch to a third position causes the plurality of flow-restricting devices to restrict the flow in a third subset of the plurality of tubes.

In an embodiment of the present invention, a tissue treatment system includes a container and a flow management device. The container includes an exterior wall surrounding an interior volume for holding tissue. The container also includes a filter structure for processing tissue. The flow management device includes a first plate having a plurality of first openings passing therethrough. The flow management device also includes a second plate having a plurality of second openings passing therethrough. The first plate and the second plate are operably connected. Setting the first plate in a first position places a first subset of the plurality of first openings in fluid communication with a first subset of the plurality of second openings. Setting the first plate in a second position places a second subset of the plurality of first openings in fluid communication with a second subset of the plurality of second openings. Setting the first plate to a third position places a third subset of the plurality of first openings in fluid communication with a third subset of the plurality of second openings.

In an embodiment of the present invention, a flow management device includes a first plate having a plurality of first openings passing therethrough. The flow management device also includes a second plate having a plurality of second openings passing therethrough. The first plate and the second plate are operably connected. Setting the first plate in a first position places a first subset of the plurality of first openings in fluid communication with a first subset of the plurality of second openings. Setting the first plate in a second position places a second subset of the plurality of first openings in fluid communication with a second subset of the plurality of second openings. Setting the first plate to a third position places a third subset of the plurality of first openings in fluid communication with a third subset of the plurality of second openings.

In an embodiment of the present invention, a flow management device includes a body including a plurality of first openings and a plurality of second openings. The flow management device also includes a multi-position switch. The flow management device also includes a spindle within the body and coupled to the multi-position switch, the spindle including a plurality of third openings. Setting the multi-position switch to a first position places a first subset of the plurality of first openings in fluid communication with a first subset of the plurality of second openings via a first subset of the plurality of third openings. Setting the multi-position switch to a second position places a second subset of the plurality of first openings in fluid communication with a second subset of the plurality of second openings via a second subset of the plurality of third openings. Setting the multi-position switch to a third position places a third subset of the plurality of first openings in fluid communication with a third subset of the plurality of second openings via a third subset of the plurality of third openings.

In an embodiment of the present invention, a flow management device includes a plurality of diaphragm units. Each diaphragm unit includes a flexible diaphragm, a first opening, and a second opening. The diaphragm units have an open position wherein the first opening and second opening are in fluid communication and a closed position wherein the first opening and the second opening are not in fluid communication. The flow management device also includes a rotating plate including one or more protrusions. Each protrusion is capable of pressing against the flexible diaphragm of a diaphragm unit to place the diaphragm unit in the closed position. Rotating the rotating plate to a first position places a first subset of the diaphragm units into the closed position. Rotating the rotating plate to a second position places a second subset of the diaphragm units into the closed position. Rotating the rotating plate to a third position places a third subset of the diaphragm units into the closed position.

In an embodiment of the present invention, a tissue treatment device includes a container. The container includes an exterior wall surrounding an interior volume for holding tissue and a filter structure for processing tissue.

In an embodiment of the present invention, a tissue treatment system includes a container and a flow management device. The container includes an exterior wall surrounding an interior volume for holding tissue and a filter structure for processing tissue. The flow management device includes a first barrier wall having a plurality of first openings passing therethrough. The flow management device includes a second barrier wall having a plurality of second openings passing therethrough. The flow management device includes a third barrier wall having one or more third openings passing therethrough. The first barrier wall, second barrier wall, and third barrier wall are operably connected. Setting the third barrier wall in a first position places a first subset of the plurality of first openings in fluid communication with a first subset of the plurality of second openings. Setting the third barrier wall in a second position places a second subset of the plurality of first openings in fluid communication with a second subset of the plurality of second openings. Setting the third barrier wall in a third position places a third subset of the plurality of first openings in fluid communication with a third subset of the plurality of second openings.

BRIEF DESCRIPTION OF THE DRAWINGS

FIG. 4 illustrates a decision matrix for determining the status of assorted system inputs in an exemplary tissue transfer system, as described in various embodiments;

FIG. 15A illustrates a tissue treatment system including a turbine in accordance with various embodiments of the present disclosure.

FIG. 15B illustrates a magnified view of a portion of the system of FIG. 15A showing the connection between the turbine and a mount for mixing blades in accordance with various embodiments of the present disclosure.

FIG. 15C illustrates a cutaway view of the turbine incorporated into the system of FIG. 15A in accordance with various embodiments of the present disclosure.

FIGS. 18A and 18B illustrate a disassembled and assembled filtering structure, respectively, according to various embodiments of the present disclosure.

FIG. 19A illustrates an exploded view of a conical mesh filter for use in tissue treatment systems according to various embodiments of the present disclosure.

FIG. 19B illustrates placement of the filter of FIG. 19A in a tissue treatment system according to various embodiments of the present disclosure.

FIG. 19C illustrates a cross-sectional view of a filtering structure according to various embodiments of the present disclosure.

FIG. 19D illustrates a pre-form for a filtering structure according to various embodiments of the present disclosure.

FIG. 19E illustrates a filtering structure, according to various embodiments of the present disclosure.

FIGS. 20A and 20B illustrate two configurations of telescoping mixing paddles for use in tissue treatment systems according to various embodiments of the present disclosure.

FIGS. 20C and 20D illustrate tissue treatment systems with telescoping mixing paddles in accordance with various embodiments.

FIGS. 21A-21D illustrate telescoping mixing paddles for use in tissue treatment systems according to various embodiments of the present disclosure.

FIGS. 22A and 22B illustrate a tissue treatment system including a mixing device with a disc portion that can be opened or closed for use as an ejection piston in accordance with various embodiments of the present disclosure.

FIGS. 31A-31D illustrate views of a tissue treatment system and a corresponding tube management device in accordance with various embodiments of the present disclosure.

FIGS. 33A-33D illustrate views of a tissue treatment system including a tube management device in accordance with various embodiments of the present disclosure.

FIG. 39A illustrates a perspective view of a tissue treatment system including a molded handle in accordance with various embodiments of the present disclosure.

FIG. 39B illustrates a side view of a tissue treatment system including a molded handle in accordance with various embodiments of the present disclosure.

FIGS. 41A-41C illustrate a tissue treatment system and associated packaging in accordance with various embodiments of the present disclosure.

FIGS. 45A and 45B illustrate a tissue treatment system including a storage system for fluid(s) in accordance with various embodiments of the present disclosure.

FIGS. 46A and 46B illustrate perspective and side views, respectively, of a tissue treatment system including a tube management device in accordance with various embodiments of the present disclosure.

FIG. 47 illustrates a tissue treatment system with a wash cycle counter in accordance with various embodiments of the present disclosure.

FIGS. 49A-49C illustrate a tissue treatment system in accordance with various embodiments of the present disclosure.

FIGS. 51A-51C illustrate views of a tissue treatment system in accordance with various embodiments of the present disclosure.

DESCRIPTION OF EXEMPLARY EMBODIMENTS

Figure 1:
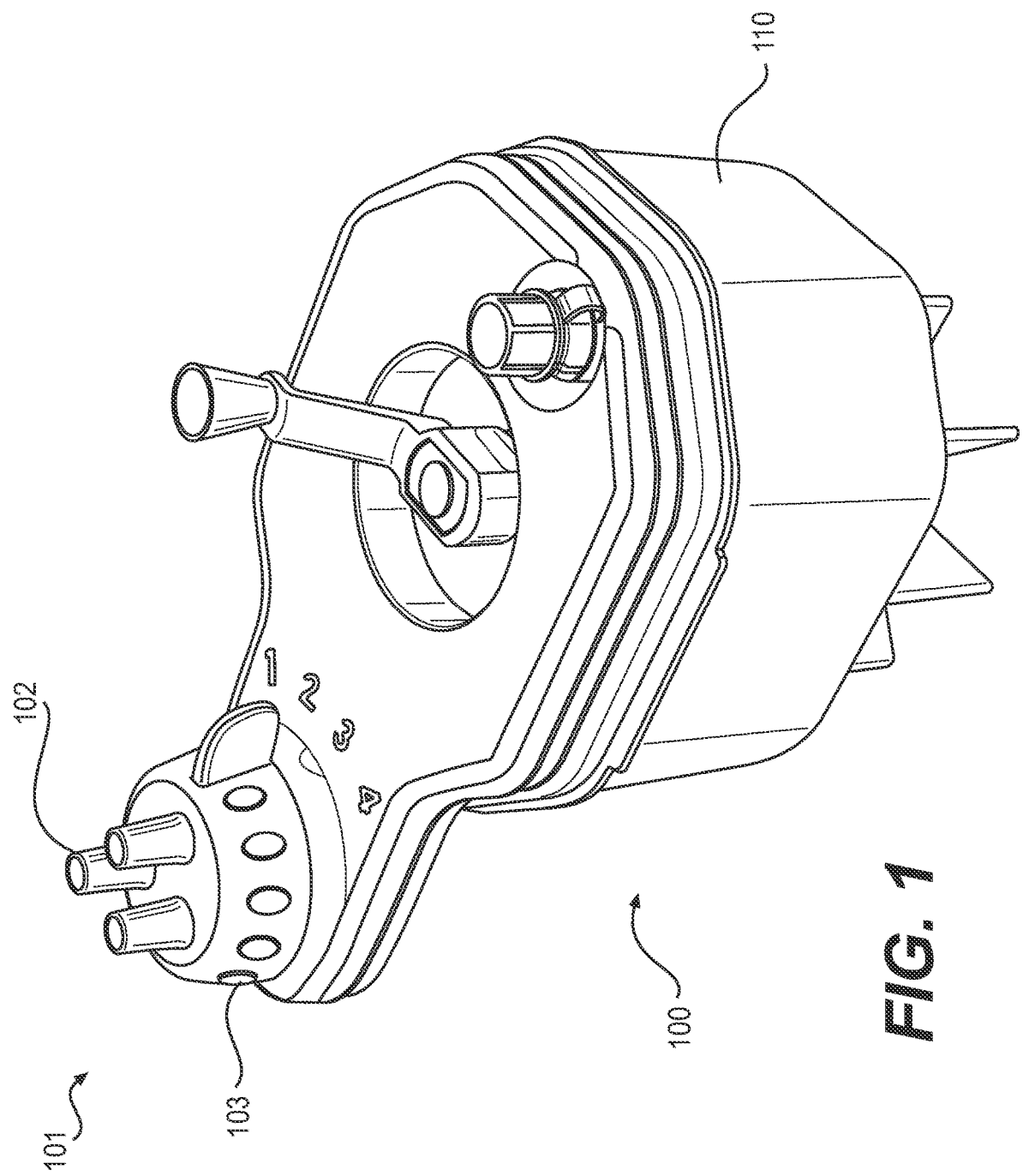
FIG. 1 illustrates a tissue treatment system according to various embodiments.

Reference will now be made in detail to certain exemplary embodiments according to the present disclosure, certain examples of which are illustrated in the accompanying drawings. Wherever possible, the same reference numbers will be used throughout the drawings to refer to the same or like parts.

In this application, the use of the singular includes the plural unless specifically stated otherwise. In this application, the use of "or" means "and/or" unless stated otherwise. Furthermore, the use of the term "including," as well as other forms such as "included" and "includes," is not limiting. The section headings used herein are for organizational purposes only and are not to be construed as limiting the subject matter described. All documents, or portions of documents, cited in this application including but not limited to patents, patent applications, articles, books, and treatises are hereby expressly incorporated by reference in their entirety for any purpose.

As used herein, "adipose tissue" refers to adipose tissue obtained by any means including, for example, liposuction and/or tumescent liposuction. In addition, the adipose tissue may be substantially intact or may be altered by, for example, washing with saline, antimicrobials, detergents, or other agents; the addition of therapeutic agents such an analgesics, antimicrobials, and anti-inflammatories; the removal of some cells or acellular components; or disruption or alteration by the collection process itself including, for example, during liposuction or tumescent liposuction. The adipose tissue can be autologous tissue, allogeneic tissue, or xenogenic tissue (e.g., porcine tissue).

As described above, some surgical procedures require use of tubes, hoses, or other conduits to transfer fluids, gases, and/or tissue products between a patient and a treatment system or device, or among systems and devices. Multi-step procedures are not uncommon and may require connection and disconnection of hoses from input and output ports. For example, a system for adipose tissue transfer and processing (e.g., adipose washing) can require over one hundred combined user actions and decisions, including enabling and disabling vacuum sources or adding or removing tissue or washing solutions to a tissue storage and treatment container. The maintenance and verification of tube connections during a surgical or medical procedure can be non-trivial, especially when the procedure has a time-sensitive component.

Various human and animal tissues can be used to produce products for treating patients. For example, various tissue products have been produced for regeneration, repair, augmentation, reinforcement, and/or treatment of human tissues that have been damaged or lost due to various diseases and/or structural damage (e.g., from trauma, surgery, atrophy, and/or long-term wear and degeneration). Fat grafting, including autologous fat grafting, can be useful for a variety of clinical applications including facial fillers, breast augmentation, buttock augmentation/sculpting, augmentation of other tissue sites, correction of lumpectomy defects, cranial-facial defect correction, and correction of lipoplasty defects (e.g., divots).

To prepare tissue for autologous fat grafting, tissue cleaning and processing must be performed. The process of grafting typically involves steps such as removal of tissue from a patient with a syringe or cannula. The removed tissue is pulled into a tissue processing container where unwanted components of the tissue (or additives to the tissue) can be separated and/or the tissue can be cleaned using various solutions. A typical system might include meshes for filtration and separation, cranks connected to mixing blades, and several input and output ports (e.g., to add or remove processing fluids and to transfer tissue). Once the tissue is sufficiently prepared, it must be removed from the container and injected or grafted back into the patient. During transfer steps, vacuum devices help move the tissue from location to location. However, it is desirable to disconnect the vacuum pressure during processing steps. In addition, the tubes that are not in use during any given step should be blocked to maintain the sterility of the system or allow application of suction or movement through appropriate tubes.

Turning to FIG. 1, an illustrative embodiment of a tissue treatment system 100 is shown. As shown, the tissue treatment system 100 can include a container having an exterior wall 110 surrounding an interior volume. The interior of the container can also contain filters, mixing blades, hoses, and other components to enable washing and conditioning of tissue. The system 100 can include a tube management device 101 to facilitate operation of the system 100. Tubes can pass from the exterior of the system 100 to the interior through ports 102 of the tube management device 101, and tube restrictor devices (discussed below) within the tube management device 101 can control which tubes are open and which are blocked for a given system configuration. The system configuration is determined by the setting of a multi-position switch 103. In some embodiments, the system 100 can be provided with a carry handle for convenient handling by a user. In some embodiments, the tube management device 101 can hold a blocked tube against at least 1 atmosphere (i.e., about 75 cmHg) of vacuum without leaking.

As used herein, the terms "tube," "hose," "conduit," or similar language will be used interchangeably and will be understood to refer to any passageway having a lumen configured to allow passage or fluids, gases, and/or tissue products therethrough.

Figure 2:
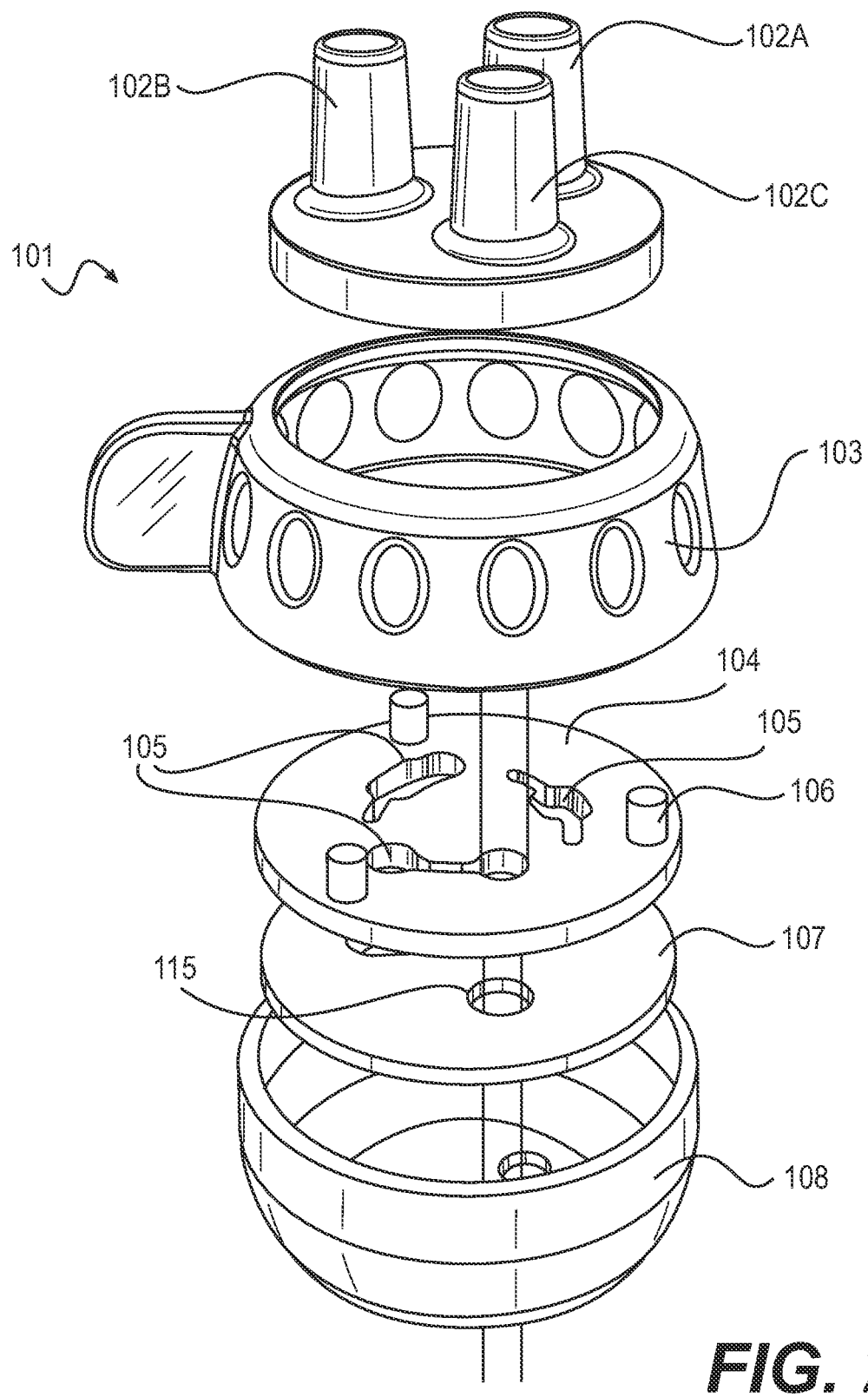
FIG. 2 is an exploded view of a tube management device according to various embodiments.

An exploded view of one embodiment of a tube management device 101 is shown in FIG. 2. The tube management device 101 may include ports 102a, 102b, 102c and a multi-position switch 103. Tubes can pass through the ports 102a, 102b, 102c and then through a tube restrictor plate 104 and a tube stabilizer plate 107 before passing out of the device 101. Based on the position of the multi-position switch 103, restrictor elements 105 on the tube restrictor plate 104 can allow or obstruct flow through each of the tubes. In some embodiments, the contents of the tube management device 101 can be contained within an exterior wall 108 that forms a body. In alternate embodiments, the components of the tube management device 101 can be attached directly to the structure of the container 110.

The ports 102a, 102b, 102c can have a variety of configurations. In accordance with various embodiments, the ports 102a, 102b, 102c may be straight-walled or barbed; threaded or unthreaded; and have no fittings, luer fittings, swaged fittings, or any other type of connector suitable for a specific application. Although the ports 102a, 102b, 102c are depicted as extending out from the body of the tube management device 101, the ports may also be threaded or unthreaded holes or recesses or may extend inward from the surface into the body of the device 101. Although only three ports are depicted in FIG. 2, any number of ports can be chosen to match the number of tubes needed in a particular application. Substances including, but not limited to, gases, liquids, chemical solutions, and biological tissues can flow into or out from the ports 102a, 102b, 102c depending upon the position of the multi-position switch and the requirements of any particular step of the medical procedure.

The position of the multi-position switch 103 can be used to switch among different device configurations. In some embodiments, the multi-position switch 103 is a rotating body or knob, and the rotational angle of the body determines the switch state. In accordance with various embodiments, the multi-position switch 103 may be any mechanical or electronic switch (including rotational or linear throw switches) that, through appropriate linkages, can alter the state of openness of tubes passing through the device. In some embodiments, the multi-position switch 103 can include non-slip grips or similar features to facilitate easier operation by a user, in particular by a user wearing surgical gloves. The positions of the multi-position switch 103 may correspond to steps in a procedure. For example, the steps in a procedure might include liposuction/tissue extraction, hold and mix, irrigation, and vacuum/clear steps.

Figure 3:
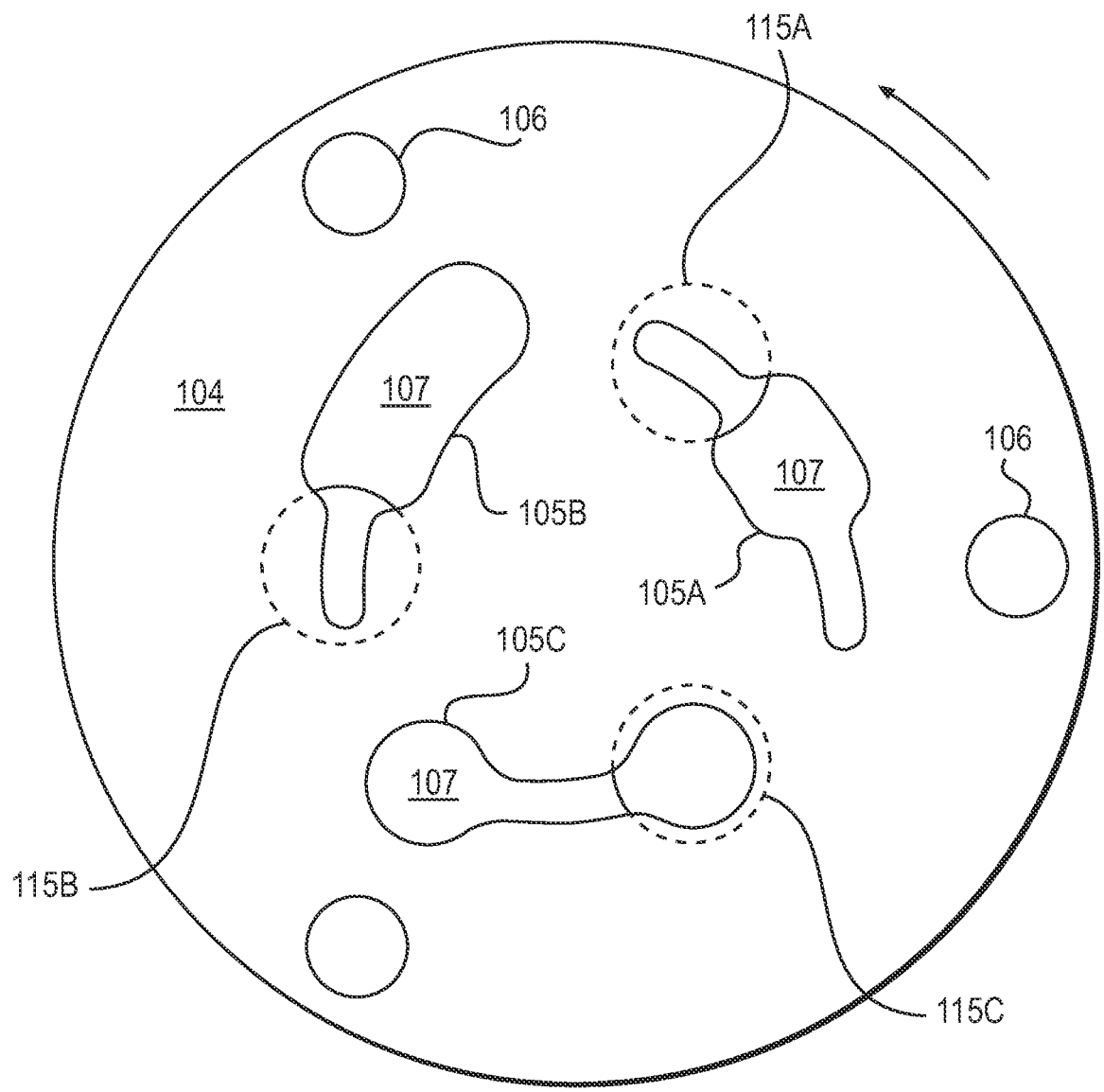
FIG. 3 is a top view of one embodiment of a tube restrictor plate and a tube stabilizer plate, which are components of a tube management system according to the present invention.

The tube restrictor plate 104 can block or allow flow through tubes that pass through the tube through-holes of the plate 104 through the use of flow-restricting devices. In accordance with various embodiments, and as depicted in FIGS. 2 and 3, the tube restrictor plate 104 may be provided with flow-restricting devices 105 in the form of contoured radial slots. The slots 105 can have a slot width that varies according to the desired action of the slot upon a tube for each angular position of the tube restrictor plate 104. For example, each slot 105 may include two slot widths that correspond to either unrestricted flow in a tube or complete blockage of flow in a tube. Alternatively, each slot may have a range of widths corresponding to different levels of flow restriction. In some embodiments, the tube restrictor plate 104 can comprise an acrylic material.

In FIG. 3, a tube restrictor plate 104 is shown overlaid upon a tube stabilizer plate 107 with slots 105a, 105b, 105c indicated. The example embodiment of a tube restrictor plate 104 shown in FIG. 3 illustrates tube through-holes in the form of contoured radial slots 105a, 105b, 105c suitable for a tube management device 101 having a multi-position switch 103 with three positions. The contoured radial slots 105a, 105b, 105c of the tube restrictor plate 104 are overlaid in this top view on the tube through-holes 115a, 115b, 115c of the tube stabilizer plate 107. In this figure, the position of tube restrictor plate 104 with respect to tube stabilizer plate 107 places slots 105a, 105b, 105c in the first position over tube through-holes 115a, 115b, 115c. Activation of the multi-position switch 103 can cause the tube restrictor plate 104 to rotate in the direction shown by the arrow while the tube stabilizer plate 107 stays in place. As a result, the radial slots can advance to the second or third position as needed. In one embodiment, activation of the multi-position switch 103 can cause the tube stabilizer plate 107 to rotate while the tube restrictor plate 104 stays in place. In accordance with various embodiments, the system 100 can be provided with a plurality of tube restrictor plates 104 having different arrangements of slots 105a, 105b, 105c intended for different procedures having different steps. In these embodiments, the user may choose one of the plurality of tube restrictor plates 104 to place within the body 108 of the device 101 depending upon the application.

The tube restrictor plate 104 may have locating features 106 that can interlock with the multi-position switch 103. The locating features 106 can help the user align the tube restrictor plate with the multi-position switch 103 and within the tube management device 101 so that the contoured radial slots 105a, 105b, 105c are properly in-line with their respective ports 102a, 102b, 102c. In addition, the locating features 106 can match with complementary features on the multi-position switch so that the switch's position reflects the proper tubing state within the tube management device 101. In some embodiments, the locating features 106 can fix the multi-position switch 103 to the tube restrictor plate 104 such that they move in concert when the switch is rotated.

The tube management device 101 can have a tube stabilizer plate 107. The tube stabilizer plate 107 may have tube through-holes 115 to allow tubes to pass therethrough. In some embodiments, the diameter of each of the tube through-holes 115 in the tube stabilizer plate 107 may be equal or approximately equal to the outer diameter of the corresponding tube that passes through the hole 115 to provide a secure fit around the outside of each tube without compression. The tube stabilizer plate 107 can hold the tube in position so that activation or movement of the tube restrictor plate 104 cannot twist, reorient, or move the tubes.

As discussed above, the system 100 can be used to operate surgical systems, such as adipose tissue transfer systems. Accordingly, an exemplary decision matrix 400 for an adipose tissue transfer process is shown in FIG. 4. The decision matrix may be used to determine the open/closed status of any tubes in the system during any steps of an adipose transfer procedure. In some embodiments, a tissue treatment system 100 similar to that shown in FIG. 1 can have 4 tube inputs that are either open or blocked during a given step of a medical procedure. In a liposuction or aspiration 402 step, the tube to the liposuction cannula and the vacuum tube may be open while the irrigation tube and vent tube are closed. In a hold and mix or washing 404 step, all 4 inputs can be blocked. In an irrigation or transfer 406 step, the tube to the liposuction cannula and the vacuum tube may be closed while the irrigation tube and the vent tube can be open. In a vacuum/clear 408 step, the tube to the liposuction cannula and the irrigation tube may be closed while the vacuum tube and the vent tube can be open.

Accordingly, and consistent with the decision matrix or foreseeable variations thereof depending on the particular tissue processing being performed, methods of processing adipose tissue are provided. The methods can include at least the following steps, which can be implemented using the various devices described herein and illustrated in any of the disclosed figures. The method can include a first step wherein the device, via a multi-position switch (see, e.g., handle 903 or switch 1003), is set for a liposuction mode, opening a tissue transfer input port and a vacuum port. The method can include a second step, for processing tissue, wherein the switch may be set to a mode for holding and processing (e.g., mixing or incubating) tissue, with all ports likely being closed. The method can further include a third step for irrigation, wherein the multi-position switch is set to allow opening of one or more irrigation or fluid input ports; and a fourth step, for vacuuming (e.g., to remove irrigation or fluid).

It will be appreciated, however, that the various steps may be modified, and/or repeated. For example, multiple irrigation and vacuum/cleaning steps may be performed, and additional ports can be included, as discussed herein.

Figure 5:
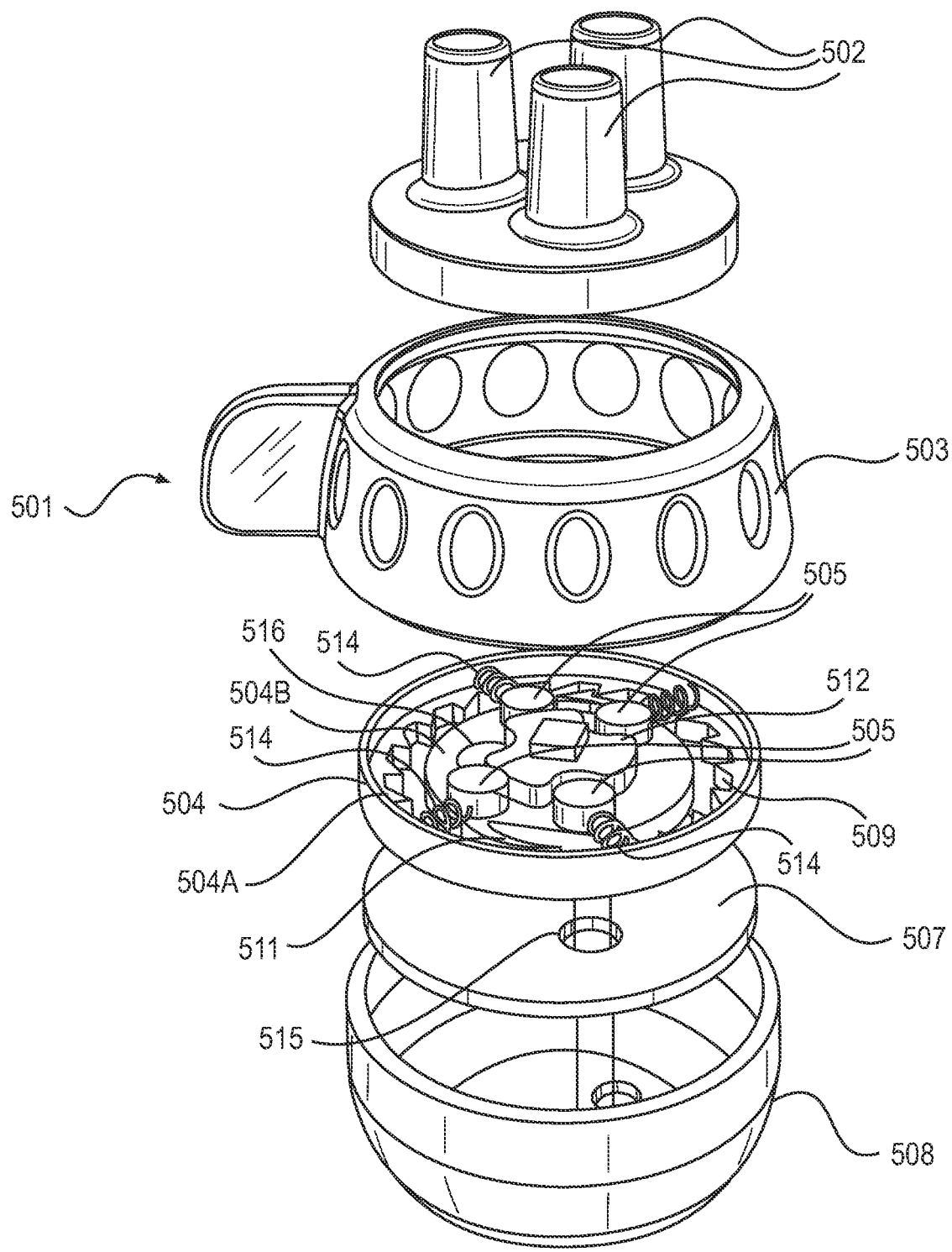
FIG. 5 is an exploded view of an alternative tube management device according to the present invention.

An alternate embodiment of a tube management device 501 is shown in FIG. 5. The tube management device 501 can include ports 502 and a multi-position switch 503. Tubes can pass from the ports 502 through a tube restrictor plate 504 and a tube stabilizer plate 507 before passing out of the device 501. Based on the position of the multi-position switch, restrictor elements 505 on the tube restrictor plate 504 can allow or obstruct flow through each of the tubes. The contents of the tube management device 501 can be contained within an exterior wall 508 that forms a body.

As with the previously discussed embodiments, the ports can have a variety of configurations. For example, the ports 502 may be straight-walled or barbed; threaded or unthreaded; and have no fittings, luer fittings, swaged fittings, or any other type of connector demanded by application-specific requirements. Although the ports 502 are depicted in this embodiment as extending out from the body of the tube management device 501, the ports may also be threaded or unthreaded recesses or holes or may extend inward from the device surface into the body of the device 501. Although only three ports are depicted in FIG. 5, any number of ports can be chosen to match the number of tubes needed in a particular application. Substances including, but not limited to, gases, liquids, chemical solutions, and biological tissues can flow into or out from the ports 502 depending upon the position of the multi-position switch and the requirements of any particular step of the surgical procedure.

The positions of the multi-position switch 503 can be used to switch among different device configurations. In some embodiments, the multi-position switch 503 is a rotating body or knob and the rotational angle of the body determines the switch state. In accordance with various embodiments, the multi-position switch 503 may be any mechanical or electronic switch (including rotational or linear throw switches) that, through appropriate linkages, can alter the state of openness of tubes passing through the device. In some embodiments, the multi-position switch 503 can include non-slip grips or similar features to facilitate easier operation by a user, in particular by a user wearing surgical gloves. The positions of the multi-position switch 503 may correspond to steps in a procedure. For example, the steps in a procedure might include liposuction/tissue extraction, hold and mix, irrigation, and vacuum/clear steps.

The tube restrictor plate 504 can block or allow flow through the tubes that pass through the tube through-holes 516 of the plate through the use of flow-restricting devices. The tube restrictor plate 504 may include an external ring 504a that is rotatably engaged with a central portion 504b. Tubes can pass through the tube restrictor plate 504 through tube through-holes 516 adjacent to flow-restricting devices. In accordance with various embodiments and as depicted in FIG. 5, the tube restrictor plate 504 may be provided with flow-restricting devices in the form of a contoured central hub 512 on the central portion 504b and sliding blocks 505 that force the tubes against the hub 512 via the integrated springs 514 attached to the external ring 504a. The sliding blocks 505 may be shaped as flat plates, cylinders, ovals, spheres, ovoid configuration, or any other shape that meets application-specific requirements. In some embodiments, the contoured central hub 512 may have an equal number of recesses to the number of ports 502, and each tube may pass through a tube through-hole 516 adjacent to a recess of the contoured central hub. When a sliding block 505 attached to an integrated spring 512 is in line with a recess of the contoured central hub 512, the force of the spring may extend the sliding block and force it against a tube. In some embodiments, the central portion 504b of the tube restrictor plate 504 may be fixedly attached to the tube stabilizer plate 507. As the multi-position switch 503 changes from one position to another, the external ring 504a of the tube restriction plate 504 may rotate while the central portion 504b containing the contoured central hub 512 does not rotate relative to the tube stabilizer plate 507.

In accordance with various embodiments, the external ring 504a may be provided with a one-way ratcheting mechanism 509. The teeth of the ratcheting mechanism can engage with a pawl 511 positioned on the central portion 504b of the tube restriction plate 504 such that rotation of the external ring 504a is allowed in one direction but prevented in the opposite direction. Although the pawl 511 is depicted as being located on the central portion 504b in this embodiment, it will be apparent to those of ordinary skill in the art that the pawl could be attached at other points throughout the tube management device 501 such as the interior of the multi-position switch 503 or the tube stabilizer plate 507.

The tube management device 501 can also include a tube stabilizer plate 507. The tube stabilizer plate 507 may have tube through-holes 515 to allow tubes to pass through. In some embodiments, the diameter of each of the tube through-holes 515 in the tube stabilizer plate 507 may be equal to or slightly greater than the outer diameter of the corresponding tube that passes through the hole to provide a secure fit around the outside of each tube without compression. The tube stabilizer plate 507 can hold the tube in position so that activation or movement of the tube restrictor plate 504 cannot twist, reorient, or move the tubes.

Figure 6:
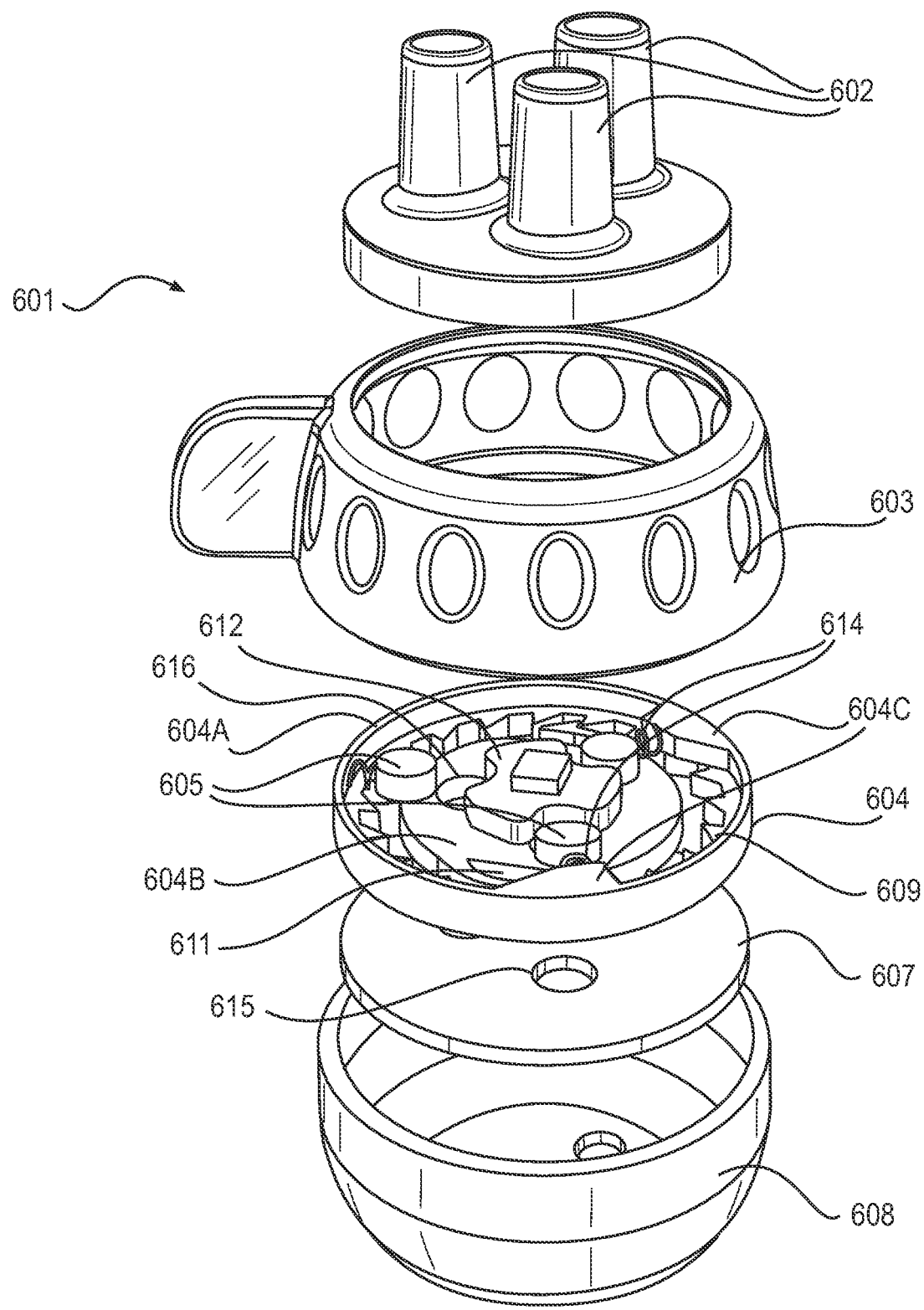
FIG. 6 illustrates a variant of the tube management device displayed in FIG. 5, according to various embodiments.

Another embodiment of a tube management device is shown in FIG. 6. The tube management device 601 can include ports 602 and a multi-position switch 603. The device 601 can include a tube stabilizer plate 607 and a tube restrictor plate 604 containing flow restriction devices. The components of the device 601 can be enclosed within a body 608.

The ports 602 are the connection between the tube management device 601 and the exterior world. In accordance with various embodiments, the ports 602 may be straight-walled or barbed; threaded or unthreaded; and have no fittings, luer fittings, swaged fittings, or any other type of connector demanded by application-specific requirements. Although the ports 602 are depicted in this embodiment as extending out from the body of the tube management device 601, the ports may also be threaded or unthreaded holes or may extend inward from the device surface into the body of the device 601. Although only three ports are depicted in FIG. 6, it will be evident to one of ordinary skill in the art that any number of ports 602 can be chosen to match the number of tubes needed in a particular application. Fluids including, but not limited to, gases, liquids, chemical solutions, and biological tissues can flow into or out from the ports 602 depending upon the position of the multi-position switch and the requirements of any particular step of the medical procedure.

The positions of the multi-position switch 603 can be used to switch among different device configurations. In some embodiments, the multi-position switch 603 is a rotating body or knob and the rotational angle of the body determines the switch state. In accordance with various embodiments, the multi-position switch 603 may be any mechanical or electronic switch (including rotational or linear throw switches) that, through appropriate linkages, can alter the state of openness of tubes passing through the device. In some embodiments, the multi-position switch 603 can include non-slip grips or similar features to facilitate easier operation by a user, in particular by a user wearing surgical gloves. The positions of the multi-position switch 603 may correspond to steps in a procedure. For example, the steps in a procedure might include liposuction/tissue extraction, hold and mix, irrigation, and vacuum/clear steps.

The tube restrictor plate 604 may include an external ring 604a that is rotatably engaged with a central portion 604b. Tubes may pass through tube through-holes 616 adjacent to flow-restricting devices. In accordance with various embodiments and as depicted in FIG. 6, the tube restrictor plate 604 may be provided with flow-restricting devices in the form of a contoured central hub 612 on the central portion 604b and sliding blocks 605 that force the tubes against the hub 612 via the integrated springs 614 attached to the external ring 604a. The sliding blocks 605 may be shaped as flat plates, cylinders, ovals, spheres, eggs, or any other shape that meets application-specific requirements. In some embodiments, the contoured central hub 612 may have an equal number of recesses to the number of ports 602, and each tube may pass through a tube through-hole 616 adjacent to a recess of the contoured central hub. When a sliding block 605 attached to an integrated spring 612 is in line with a recess of the contoured central hub 612, the force of the spring may extend the sliding block and force it against a tube. As the multi-position switch 603 changes from one position to another, the external ring 604a of the tube restriction plate 604 may rotate while the central portion 604b containing the contoured central hub 612 does not rotate relative to the tube stabilizer plate 607. In accordance with various embodiments, the sliding blocks 605 and integrated springs 614 can be placed at different radial depths using spacers 604c.

The tube management device 601 can have a tube stabilizer plate 607 in some embodiments. The tube stabilizer plate 607 may have tube through-holes 615 to allow tubes to pass through. In preferred embodiments, the diameter of each of the tube through-holes 615 in the tube stabilizer plate 607 may be equal to the outer diameter of the corresponding tube that passes through the hole to provide a secure fit around the outside of each tube without compression. The tube stabilizer plate 607 can hold the tube in position so that activation or movement of the tube restrictor plate 604 cannot twist, reorient, or move the tubes.

Figure 7:
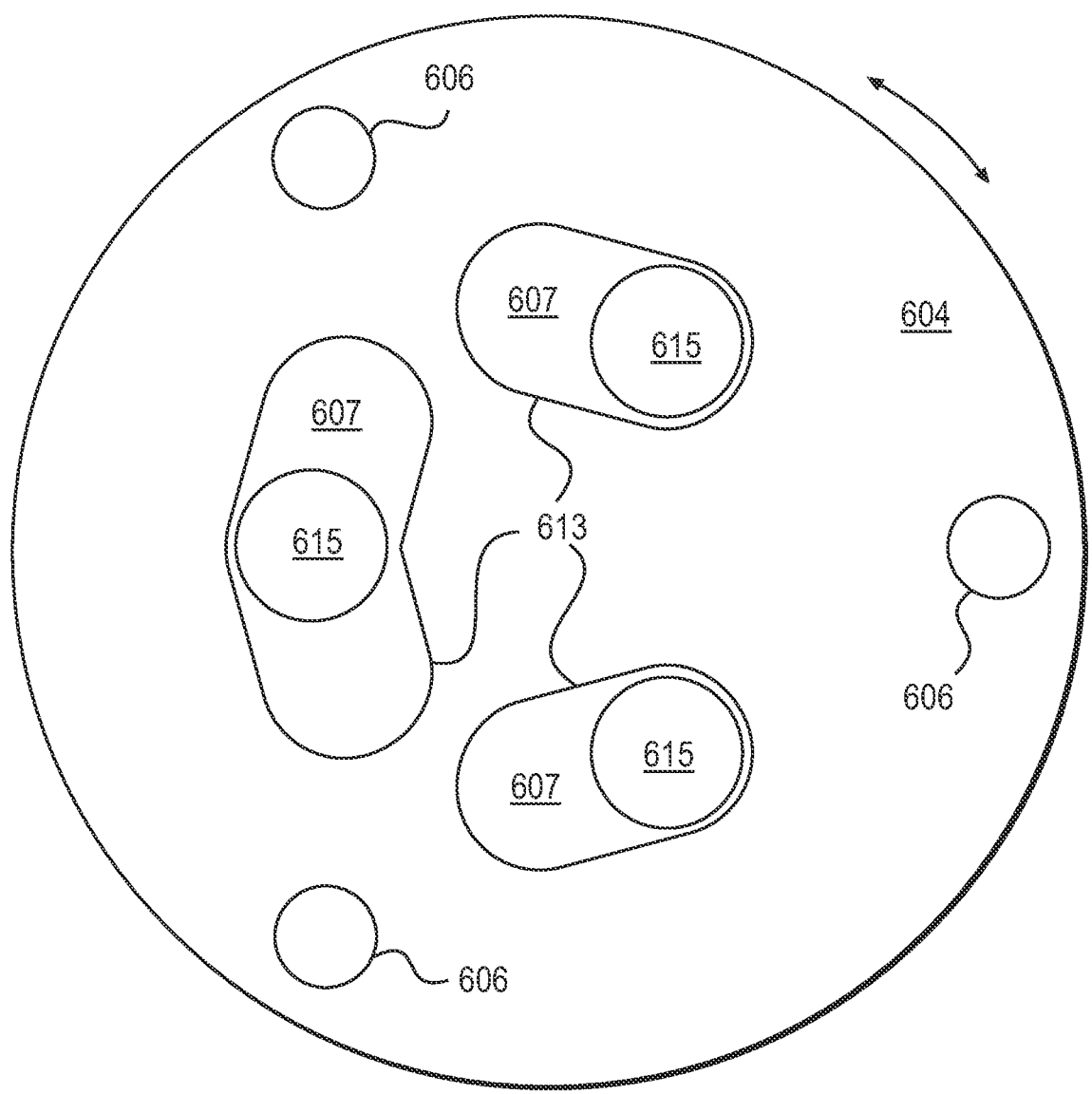
FIG. 7 is a top view of a tube restrictor plate and a tube stabilizer plate of the tube management device of the embodiment shown in FIG. 6.

A top view of the tube restrictor plate 604 overlaid on tube stabilizer plate 607 of the embodiment of FIG. 6 is shown in FIG. 7. In accordance with various embodiments, the tube restrictor plate 604 can have slots 613 to allow the tubes to change position with respect to the contoured central hub 612 of the central portion 604b and the associated flow-restricting devices. In this way, a single embodiment of the tube restrictor plate 604 can be used in more than one configuration. When a tube is in an "in" position, the tube passes near a recess of the contoured central hub 612 and can be closed by sliding blocks 605 attached to spacers 604c extending from the external ring 604a. When a tube is in an "out" position, the tube passes near an extended portion of the contoured central hub 612. In this position, the tube can be closed by sliding blocks 605 that are attached by integrated springs 614 directly to the external ring 604a. In a preferred embodiment, sliding blocks 605 attached directly to the external ring 604a without spacers 604c cannot reach tubes adjacent to recesses of the contoured central hub 612.

In accordance with various embodiments, the external ring 604a may be provided with a one-way ratcheting mechanism 609. The teeth of the ratcheting mechanism can engage with a pawl 611 positioned on the central portion 604b of the tube restriction plate 604 such that rotation of the external ring 604a is allowed in one direction but prevented in the opposite direction. Although the pawl 611 is depicted as being located on the central portion 604b in this embodiment, it will be apparent to those of ordinary skill in the art that the pawl could be attached at other points throughout the tube management device 601 such as the interior of the multi-position switch 603 or the tube stabilizer plate 607.

A method of managing surgical conduits is also envisioned by the inventors. The method includes providing several tubes and several flow-restricting devices within a body where each of the flow-restricting devices is proximal to at least one of the tubes and providing a multi-position switch wherein the flow in a first subset of the tubes is restricted by the flow-restricting devices when the switch is in a first position and flow in a second subset of tubes different than the first subset is restricted by the flow-restricting devices when the switch is in a second position. The method can further include switching from the first position of the multi-position switch to the second position.

The step of providing several tubes and several flow-restricting devices within a body where each of the flow-restricting devices is proximal to at least one of the tubes may include, but is not limited to, passing tubes through ports 102 and past flow-restricting devices 105 in a tube management device 101 as described above in connection with FIGS. 1-3.

The step of providing a multi-position switch wherein the flow in a first subset of the tubes is restricted by the flow-restricting devices when the switch is in a first position and flow in a second subset of tubes different than the first subset is restricted by the flow-restricting devices when the switch is in a second position may include, but is not limited to, providing a multi-position switch 103 in a tube management device 101 as described above in connection with FIGS. 1-3.

The step of switching from the first position of the multi-position switch to the second position may include, but is not limited to, switching a multi-position switch 103 from a first position to a second position as described above in connection with FIGS. 1 and 2.

Figure 8:
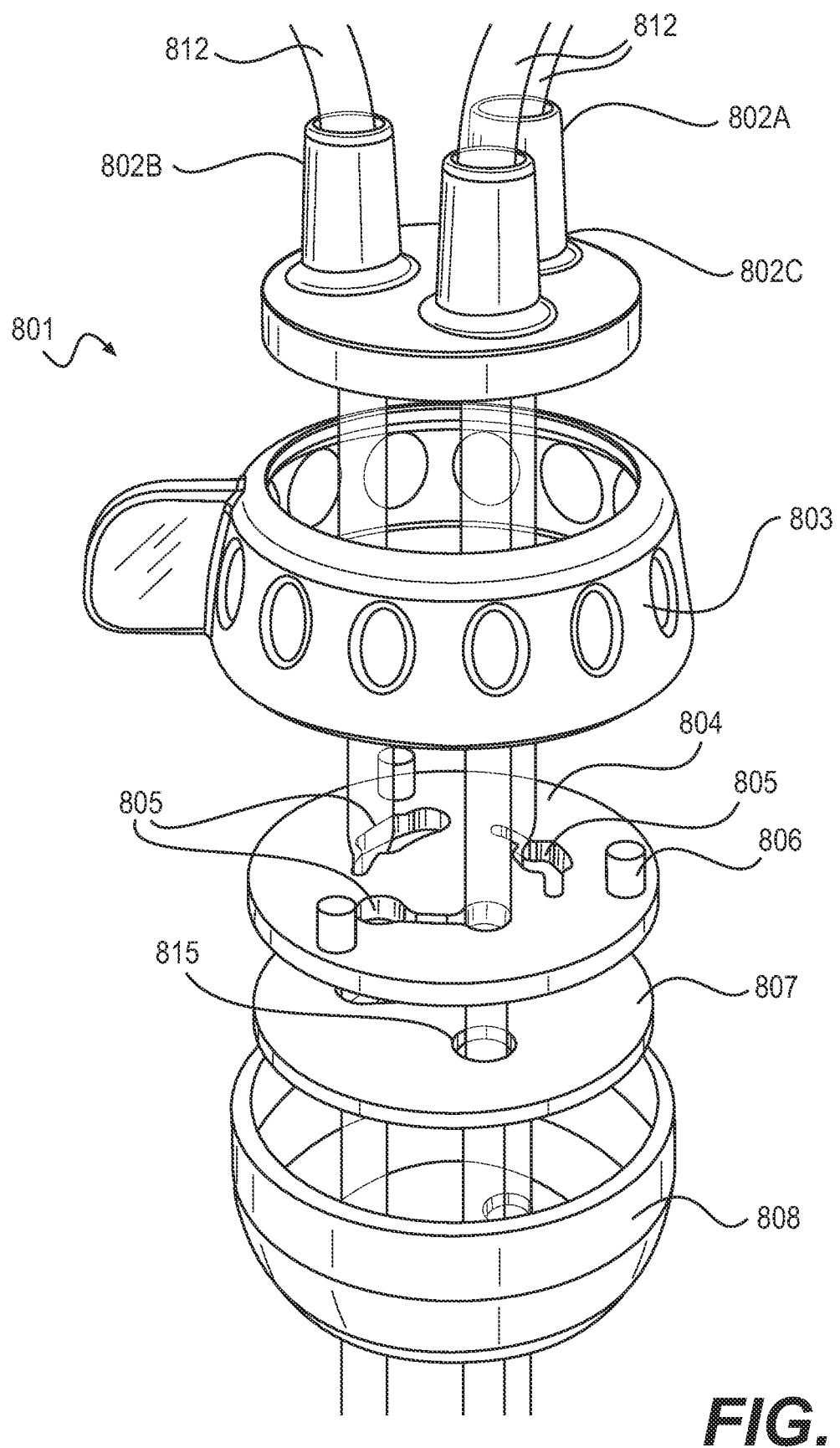
FIG. 8 illustrates a tube management device according to various embodiments.

An exploded view of an alternative embodiment of a tube management device 801 is shown in FIG. 8. The tube management device 801 may include ports 802a, 802b, 802c and a multi-position switch 803. Tubes 812 pass through the ports 802a, 802b, 802c and then through a tube restrictor plate 804 and a tube stabilizer plate 807 before passing out of the device 801. Based on the position of the multi-position switch 803, restrictor elements 805 on the tube restrictor plate 804 can allow or obstruct flow through each of the tubes 812. In some embodiments, the contents of the tube management device 801 can be contained within an exterior wall 808 that forms a body.

The ports 802a, 802b, 802c can have a variety of configurations as described previously with respect to FIG. 2. In accordance with various embodiments, the ports 802a, 802b, 802c may be straight-walled or barbed; threaded or unthreaded; and have no fittings, luer fittings, swaged fittings, or any other type of connector suitable for a specific application. Although the ports 802a, 802b, 802c are depicted as extending out from the body of the tube management device 801, the ports may also be threaded or unthreaded holes or recesses or may extend inward from the surface into the body of the device 801. Although only three ports are depicted in FIG. 8, any number of ports can be chosen to match the number of tubes 812 needed in a particular application. Substances including, but not limited to, gases, liquids, chemical solutions, and biological tissues can flow into or out of tubes 812 passing through the ports 802a, 802b, 802c depending upon the position of the multi-position switch and the requirements of any particular step of a medical procedure.

As described above with reference to FIG. 2, the position of the multi-position switch 803 can be used to switch among different device configurations. In some embodiments, the multi-position switch 803 is a rotating body or knob, and the rotational angle of the body determines the switch state. In accordance with various embodiments, the multi-position switch 803 may be any mechanical or electronic switch (including rotational or linear throw switches) that, through appropriate linkages, can alter the state of openness of the tubes 812. In some embodiments, the multi-position switch 803 can include non-slip grips or similar features to facilitate easier operation by a user, in particular by a user wearing surgical gloves. The positions of the multi-position switch 803 may correspond to steps in a procedure. For example, the steps in a procedure might include liposuction/tissue extraction, hold and mix, irrigation, and vacuum/clear steps.

The tube restrictor plate 804 can block or allow flow through the tubes 812 as they pass through the plate through the use of flow-restricting devices. Similar to the embodiments depicted in FIGS. 2 and 3, the tube restrictor plate 804 may be provided with both flow-restricting devices and tube through-holes in the form of contoured radial slots 805. In alternative embodiments, the flow-restricting devices can be similar to those described above with reference to the embodiments of FIGS. 5 and 6. The slots 805 can have a slot width that varies according to the desired action of the slot upon a tube 812 for each angular position of the tube restrictor plate 804. For example, each slot 805 may include two slot widths that correspond to unrestricted flow in a tube 812 and complete blockage of flow in a tube 812. Alternatively, each slot may have a range of widths corresponding to different levels of flow restriction.

The tube restrictor plate 804 may have locating features 806 that can interlock with the multi-position switch 803. The locating features 806 can help the user align the tube restrictor plate 804 with the multi-position switch 803 and within the tube management device 801 so that the contoured radial slots 805 are properly in-line with their respective ports 802a, 802b, 802c. In addition, the locating features 806 can match with complementary features on the multi-position switch so that the switch's position reflects the proper tubing state within the tube management device 801. In some embodiments, the locating features 806 can fix the multi-position switch 803 to the tube restrictor plate 804 such that they move in concert when the switch is rotated.

The tube management device 801 can have a tube stabilizer plate 807. The tube stabilizer plate 807 may have tube through-holes 815 to allow tubes to pass therethrough. In some embodiments, the diameter of each of the tube through-holes 815 in the tube stabilizer plate 807 may be equal or approximately equal to the outer diameter of the corresponding tube that passes through the hole to provide a secure fit around the outside of each tube without compression. The tube stabilizer plate 807 can hold the tube in position so that activation or movement of the tube restrictor plate 804 cannot twist, reorient, or move the tubes.

The tubes 812 of tube management device 801 can be made of any material that meets application-specific requirements. The tubes 812 may be made of, for example but not limited to, PVC, high-density polyethylene, nylon, latex, silicone, polyurethane, TYGON®, or any non-reactive tubing or hose. As depicted in FIG. 8, the tubes 812 may extend out of the ports 802a, 802b, 802c or may terminate within or below the ports 802a, 802b, 802c. The tubes 812 may be permanently attached to the tube management device 801, for example, at the ports 802a, 802b, 802c or body 808, or the tubes 812 may be removable and/or replaceable. In accordance with various embodiments, the tubes 812 may be disposed of after each procedure and replaced with new tubes 812 to allow for reuse of tube management device 801 for multiple procedures.

The embodiments described above include tube management devices that are operable to release or constrict flow within tubes depending upon the configuration of the device. In addition to tube management devices, flow management devices taught herein can allow or interrupt flow between a plurality of first openings and a plurality of second openings. The first and second openings can be connected to fluid ports or tubes to carry liquids, gases, or biological material. In some embodiments, the first openings and the second openings can be defined in stationary or movable walls, plates, or other barrier materials that otherwise prevent the passage of liquids, gases, or biological material. In addition, the various embodiments can be combined and interchanged, e.g., using combinations of tube management devices described above and the systems for controlling flow through various openings. Several embodiments and implementations of flow management devices are described below.

Figure 9A:
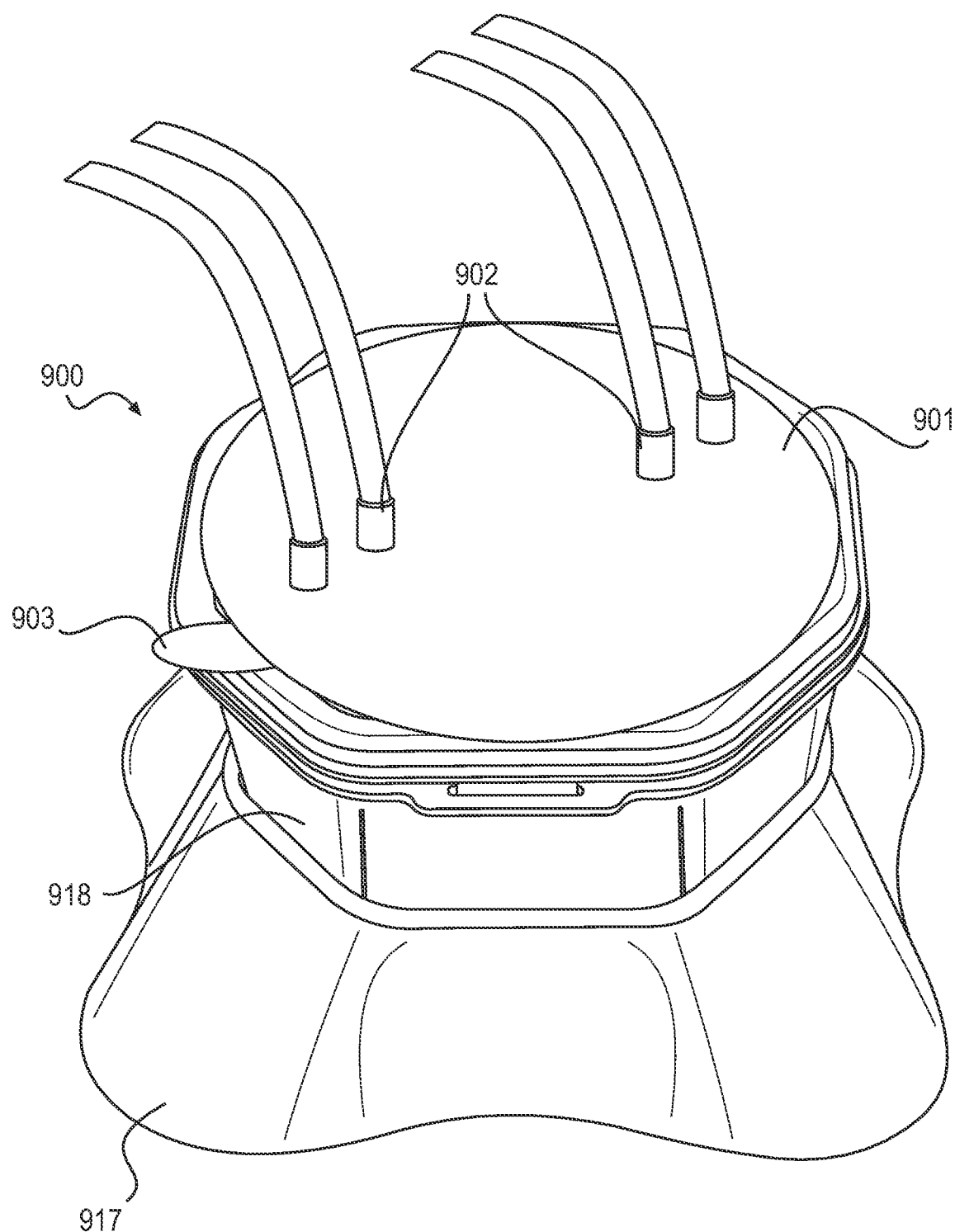
FIG. 9A illustrates a tissue processing device including a flow management device in accordance with various embodiments of the present disclosure.

FIG. 9A illustrates a tissue processing device 900 including a flow management device 901, a canister 918, and a stabilizing base 917. The flow management device 901 can include ports 902 and a handle 903, which can serve as a multi-position switch. By moving the handle 903, a user can allow, stop, or impede flow (e.g., from medical tubing) to the ports 902 and into the canister 918. In some embodiments, the canister 918 can be separated from and reattached to the stabilizing base 917.

Figure 9B:
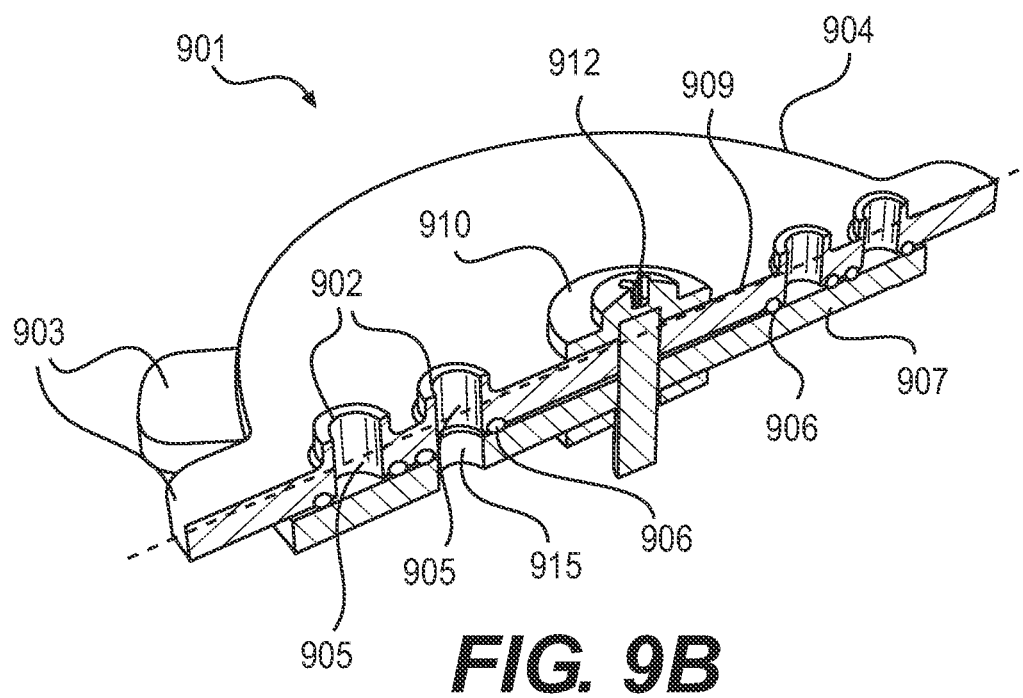
FIG. 9B illustrates a cutaway view of the flow management device of FIG. 9A in accordance with various embodiments of the present disclosure.
Figure 9C:
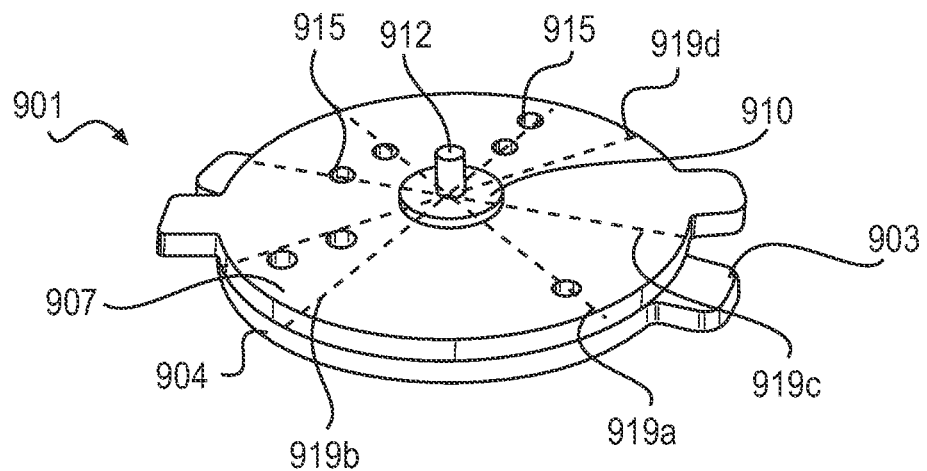
FIG. 9C illustrates a partial view of a component of the flow management device shown in FIG. 9B in accordance with some embodiments of the present disclosure.

FIG. 9B illustrates a cutaway view of the flow management device 901 of FIG. 9A while FIG. 9C illustrates a partial view of a component of the flow management device 901 in accordance with various embodiments of the present disclosure. The flow management device 901 can include a plurality of first openings 905 passing through a first plate 904 and a plurality of second openings 915 passing through a second plate 907. The first plate 904 can be placed in different rotational positions with respect to the second plate 907. In some positions of the first plate 904, a subset of the plurality of first openings 905 can be placed in fluid communication with a subset of the plurality of second openings 915 to allow passage of gases, fluids, or tissue materials through the first plate 904 and second plate 907, and therefore into or out of a treatment system.

The first plate 904 can be coupled to the second plate 907 such that the plates can be moved relative to one another to control flow through the device 901. For example, the first plate 904 and second plate 907 can be coupled using a rotatable connection such as a pivot 912 and retaining washers 910. The flow management device 901 including the first plate 904 and the second plate 907 can act as a lid to enclose the tissue processing device 900. The first plate 904 can be stationary while the second plate 907 rotates with respect to a reference (such as the canister 918). In some embodiments, the second plate 907 can be stationary while the first plate 904 rotates with respect to a reference (such as the canister 918). In some embodiments, both the first plate 904 and the second plate 907 can rotate with respect to a reference (such as the canister 918). In some embodiments, the first plate 904 and the second plate 907 can include low-friction polymers such as acetal.

Although the first and second plates are depicted in FIG. 9B as flat plates with a round perimeter, it is contemplated that the first and second plates could be any shape, dimension, or thickness that does not interfere with the purposes described herein. For example, the plurality of first openings and the plurality of second openings can be defined on curved surfaces such as walls or barriers that can translate, rotate, slide, or otherwise change position with respect to one another.

In addition, the plates can be alternatively replaced with or described as a barrier wall(s) that can prevent flow of fluid unless openings passing therethrough are aligned. Accordingly, the devices discussed herein can include a plurality of first openings 905 passing through a first barrier wall 904 and a plurality of second openings 915 passing through a second barrier wall 907. The first barrier wall 904 can be placed in different rotational positions with respect to the second barrier wall 907. In some positions of the first barrier wall 904, a subset of the plurality of first openings 905 can be placed in fluid communication with a subset of the plurality of second openings 915 to allow passage of gases, fluids, or tissue materials through the first barrier wall 904 and second barrier wall 907, and therefore into or out of a treatment system.

Figure 9D:
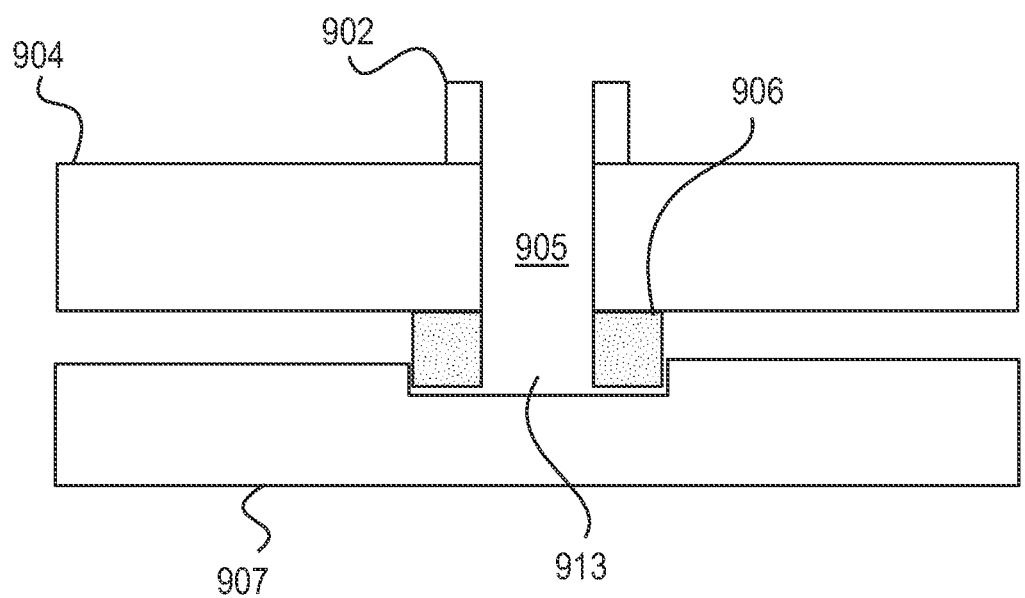
FIG. 9D illustrates a side cross-sectional view of the flow management device of FIG. 9B in accordance with some embodiments of the present disclosure.

Each of the plurality of first openings 905 or the plurality of second openings 915 can be surrounded at an end by a seal 906. The seals 906 may be an O-ring, a grommet, or any suitable sealing element. In some embodiments, the seal(s) 906 can be formed of thermoplastic elastomer (TPE) and can be molded concurrently with the first plate 904 or second plate 907 using a twin-shot molding technique. The seals 906 can create a barrier to prevent gas, fluid, or other material from escaping between the first plate 904 and the second plate 907. The first plate, second plate, or both can include a plurality of recessed portions 913 sized to fit the seals 906 as shown in FIG. 9D. The seals 906 can be placed into the recessed portions 913. When the seals 906 are placed in the recessed portion 913, the flow management device 901 is in a stored state that can avoid placing compressive forces on the seals 906 when the system is not used for an extended time such as during shipping or storage. By not subjecting the seals 906 to long periods of compression, the life of the seals 906 can be extended. In some embodiments, none of the first openings 905 is in fluid communication with any second opening 915 while the flow management device 901 is in the stored state. Although the recessed portion 906 is illustrated as being in the second plate 907 in FIG. 9D, it is also contemplated that the recessed portions 906 could be in the first plate 904 or both the first plate 904 and the second plate 907.

The first plate 904 can include ports 902 to couple tubes 912 to the first plate 904. The ports 902 can have a variety of configurations. In accordance with various embodiments, the ports 902 may be straight-walled or barbed; threaded or unthreaded; and have no fittings, luer fittings, swaged fittings, or any other type of connector suitable for a specific application. Although the ports 902 are depicted as extending out from the body of the flow management device 901, the ports may also be threaded or unthreaded holes or recesses or may extend inward from the surface into the first plate 904. Although only four ports are depicted in FIG. 9A, any number of ports can be chosen to match the number of tubes needed in a particular application. Substances including, but not limited to, gases, liquids, chemical solutions, and biological tissues can flow into or out from the ports 902 depending upon the position of the first plate or second plate and the requirements of any particular step of the medical procedure.

The flow management device 901 can include handles 903 to enable a user to more easily rotate one or both of the first plate 904 and the second plate 907. The handles 903 can be formed integrally with the first plate 904, second plate 907, or both or can be formed separately and attached.

In some embodiments, the plurality of first openings 905 can be oriented in one or more lines 909 along the first plate 904 or may be positioned in other arrangements on the first plate 904. In some embodiments, the plurality of second openings 915 can be oriented in one or more lines 919a-919d along the second plate 907, or can be positioned in other suitable arrangements on the second plate 907. Each of the lines 919a-919d can correspond, for example, to one of the steps 402, 404, 406, 408 in the decision matrix 400 as described above with reference to FIG. 4. For example, the position of the first plate 904 or second plate 907 can be adjusted to bring the line 909 including four first openings 905 into alignment with the line 919a including two second openings 915. This operation will place two first openings 905 into fluid communication with two second openings 915 as described above for step 402 in decision matrix 400. The line 909 can be aligned with other lines 919b-919d corresponding to the other steps in the decision matrix, respectively.

The flow management device 901 described above with respect to FIGS. 9A-9D includes two plates and can operate to restrict the flow by rotating the first plate 904 with respect to the second plate 907. In other embodiments taught herein below, a flow management device 1000 or system can include a third plate sandwiched between the first plate and the second plate. By changing the position or rotation of the third plate, fluid flow can be allowed or interrupted between openings in the first plate and the second plate.

Figure 10A:
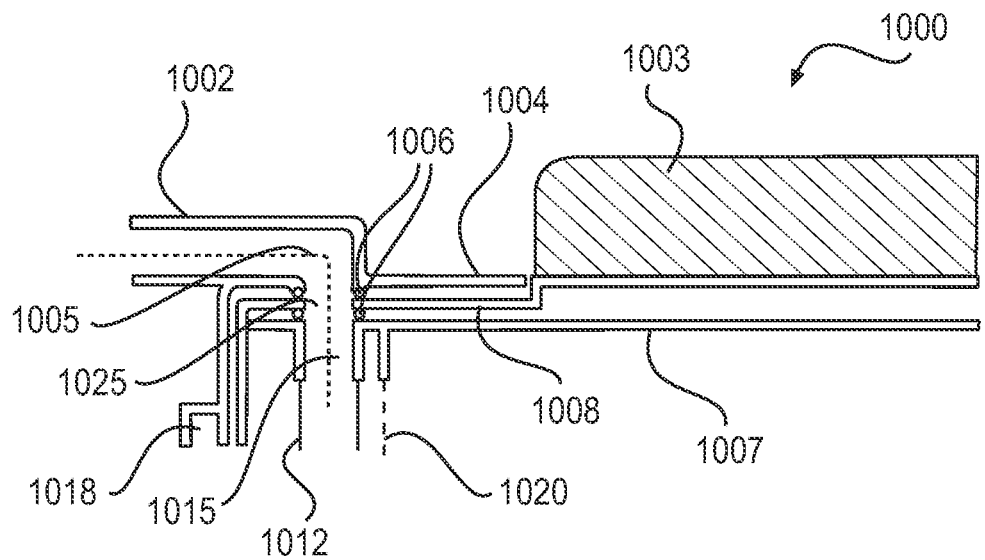
FIGS. 10A and 10B illustrate cross-sectional views of portions of flow management devices in accordance with various embodiments of the present disclosure.
Figure 10B:
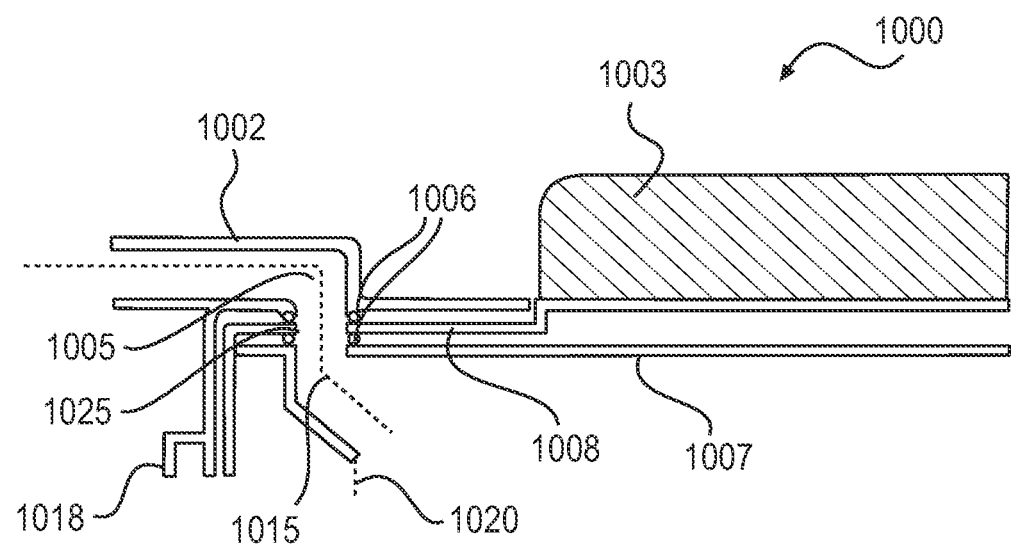

FIGS. 10A and 10B illustrate cross-sectional views of portions of flow management devices 1000 in accordance with various embodiments of the present disclosure. As shown in FIG. 10A, the flow management device 1000 includes a first plate 1004, a second plate 1007, and a third plate 1008. In some embodiments, the first plate 1004 can include a plurality of first openings 1005, the second plate 1007 can include a plurality of second openings 1015, and the third plate can include one or more third openings 1025. By placing the third plate 1008 in different rotational positions with respect to the first plate 1004 and the second plate 1007, the third openings 1025 can be configured to allow fluid communication between a subset of the first openings 1005 and a subset of the second openings 1015.

In addition, the plates can be alternatively replaced with or described as a barrier wall(s) that can prevent flow of fluid unless openings passing therethrough are aligned. Accordingly, the flow management device 1000 includes a first barrier wall 1004, a second barrier wall 1007, and a third barrier wall 1008. In some embodiments, the first barrier wall 1004 can include a plurality of first openings 1005, the second barrier wall 1007 can include a plurality of second openings 1015, and the third barrier wall can include one or more third openings 1025. By placing the third barrier wall 1008 in different rotational positions with respect to the first barrier wall 1004 and the second barrier wall 1007, the third openings 1025 can be configured to allow fluid communication between a subset of the first openings 1005 and a subset of the second openings 1015.

In accordance with various embodiments, the third plate 1008 can be disk-shaped and the one or more third openings 1025 in the third plate 1008 can be arranged at the same radial position on the disk or at different radial positions. In some embodiments, the third plate 1008 can rotate while the first plate 1004 and the second plate 1007 are stationary.

In some embodiments, the one or more third openings 1025 can be surrounded on one or both sides of the third plate 1008 by a seal 1006. In some embodiments, the seal 1006 may be an O-ring, a grommet, or any suitable sealing element. The seal 1006 can create a barrier to prevent gas, fluid, or other material from escaping between the first plate 1004 and the third plate 1008 or the second plate 1007 and the third plate 1008. In some embodiments, the first plate 1004, second plate 1007, or third plate 1008, alone or in any combination, can include a plurality of recessed portions sized to fit the seals 1006. The recessed portions can operate as described above with respect to FIG. 9D to protect the seals 1006 from experiencing extended outs of compression. In some embodiments, none of the first openings 1005 is in fluid communication with any of the third openings 1025 disposed in the third plate 1008 or with any second opening 1015 while the flow management device 1000 is in the stored state.

In some embodiments, the first plate 1004 can include one or more ports 1002 to couple tubes 1012 to the first plate 1004 similar to the ports 902 described above with reference to FIG. 9A. Each of the one or more ports can be in fluid communication with one of the plurality of first openings 1005 in the first plate 1004. In some embodiments, the first plate 1004 can be coupled to a sidewall 1018 to form an enclosed tissue-processing device.

The multi-position switch 1003 can cause rotation of the third plate 1008 with respect to the first plate 1004 and the second plate 1007. The multi-position switch 1003 can include knobs or dials that rotate or can include handles that a user can grip to cause rotation.

In one embodiment the device can include at least two chambers separated by a filter, membrane, and/or solid wall. By aligning the various openings between the two or more plates, access to the chambers can be controlled. The chambers can be positioned next to each other in a side-by-side configuration or with one chamber on top of the other chamber. Alternatively, and as described below, a first chamber can be positioned within a second chamber.

In FIG. 10A, the combined opening formed by the first opening 1005, second opening 1015, and third opening 1025 can be used to draw a vacuum on the interior of the container 1018 using, for example, a vacuum pump or in-house vacuum provided at a facility. The vacuum can be directed into the other chamber. In accordance with various embodiments, the second plate 1007 can act as a frame to support an inner mesh 1020. The inner mesh 1020 can contain material such as tissue products while allowing fluid to pass through. In some embodiments, a transfer port can be in fluid communication with the interior volume of the container or mesh. In some embodiments, the transfer port can be in fluid communication with an inner chamber defined within the inner mesh 1020. Alternatively or additionally, the devices described herein can include additional transfer ports that are in fluid communication with the container interior outside the inner mesh 1020.

In FIG. 10B, the combined opening formed by the first opening 1005, the second opening 1015, and the third opening 1025 can be used to transport fluids such as Ringer's solution or tissues such as those associated with liposuction (i.e., liposuction-derived adipose tissue). In some embodiments, the second opening 1015 can be connected to an inner chamber such that tissue products entering through the second opening 1015 are captured inside the inner chamber. In some embodiments, the second opening 1015 can be connected to an outer chamber such that fluids in the outer chamber can be removed through the second opening 1015.

As shown in FIGS. 10A and 10B, a portion of the second opening can define a pathway that directs flow of fluids, gasses, and/or solids into the inner and/or outer chamber. As shown in FIG. 10B, the second opening can define a pathway inside the device that directs material into a desired location within the device. In one embodiment, the second opening has an angled configuration to direct material into the inner chamber of the device. As shown in FIG. 10B, vacuum tubing 1012 can be coupled to the second plate 1007 to extend a pathway into a desired location within the device.

Figure 11A:
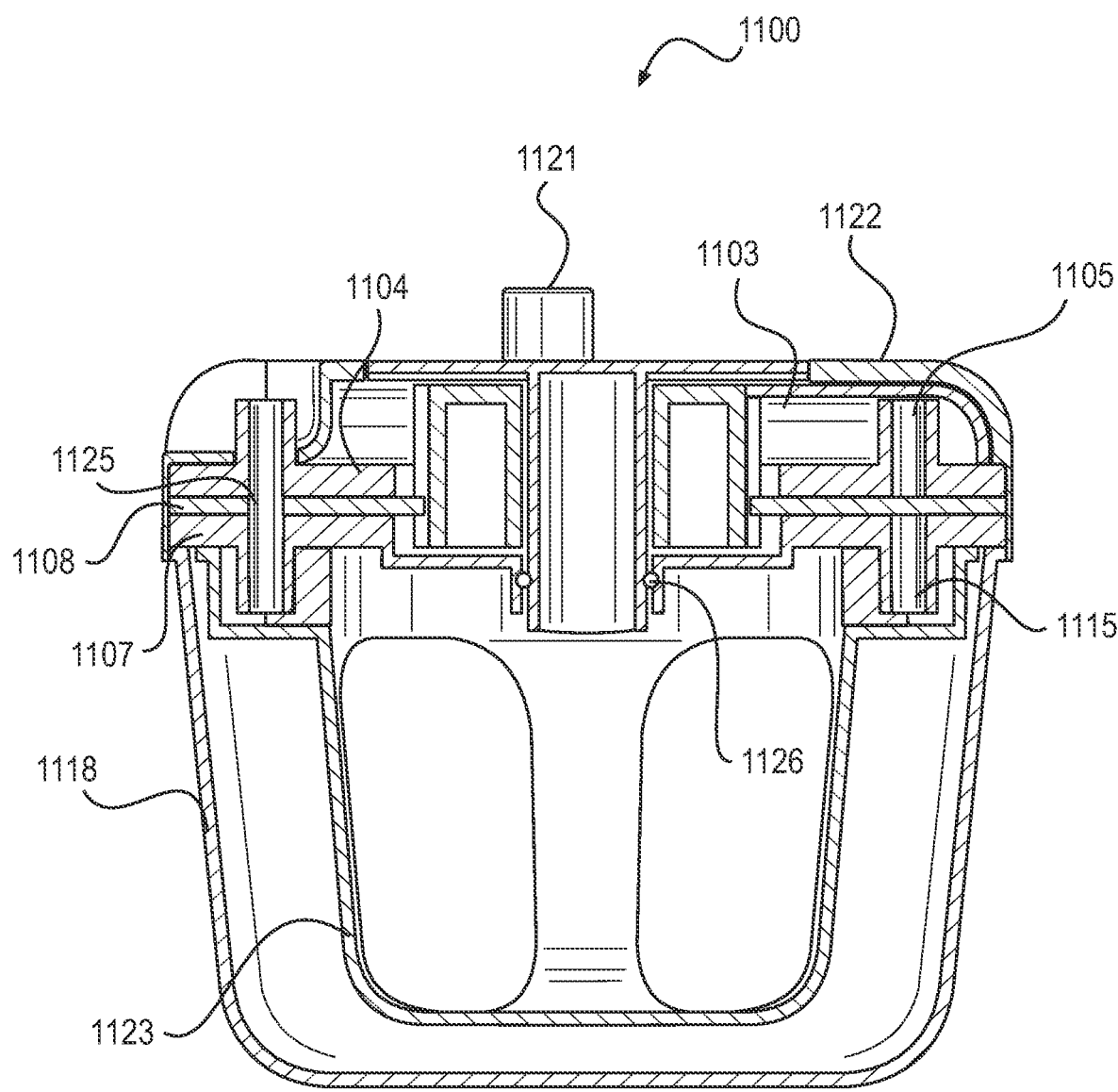
FIG. 11A illustrates a cutaway view of a tissue treatment system including an integrated flow management device in accordance with various embodiments of the present disclosure.
Figure 11B:
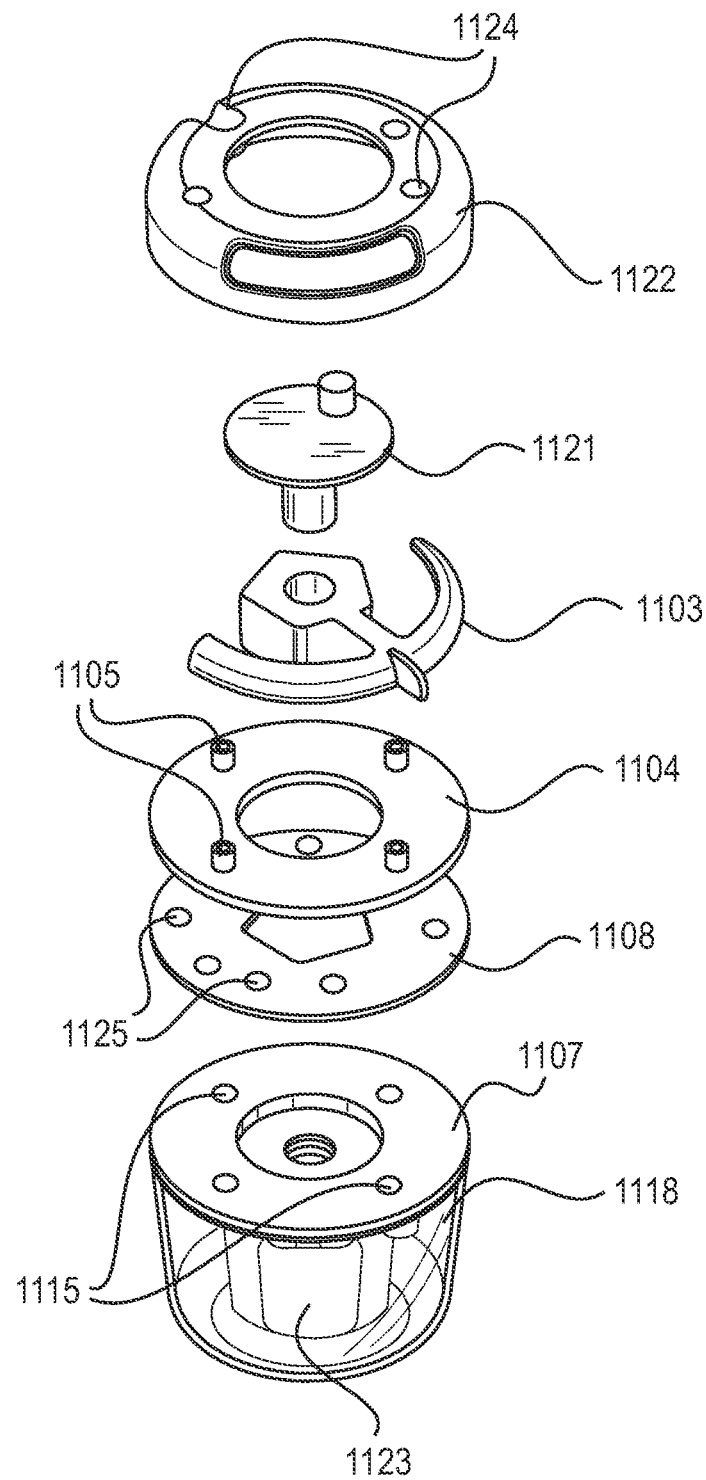
FIG. 11B illustrates an exploded view of the tissue treatment system of FIG. 11A.

FIGS. 11A and 11B illustrate a cutaway view and an exploded view, respectively, of a tissue treatment system 1100 including an integrated flow management device in accordance with some embodiments of the present disclosure. The flow management device is similar to the flow management device 1000 described above with respect to FIG. 10A or 10B. The tissue treatment system 1100 can include a top cover 1122, a rotary handle 1121, a multi-position switch 1103, a first plate 1104 including a plurality of first openings 1105 therethrough, a second plate 1107 including a plurality of second openings 1115 therethrough, a third plate 1108 including one or more third openings 1125 therethrough, a container 1118, and a filter 1123. When assembled, the tissue treatment system 1100 can be used in some embodiments to process adipose tissue including steps such as aspiration, irrigation, mixing, separation, or transfer. By operating the multi-position switch 1103 coupled to the third plate 1108, the third openings 1125 can be positioned to allow fluid communication between a subset of the first openings 1105 and a subset of the second openings 1115. In some embodiments, placement of the multi-position switch 1103 in a first position can connect a subset of first openings 1105 to a subset of second openings 1115 that are in fluid communication with the inner chamber 1140 of the system 1100. In some embodiments, placement of the multi-position switch 1103 in a second position can connect a subset of first openings 1105 to a subset of second openings 1115 that are in fluid communication with the outer chamber 1141 of the system 1100.

In some embodiments, the top cover 1122 can be attached to the container 1118 using a snap fit or an adhesive to promote sterility inside the tissue treatment system 1100. In some embodiments, the top cover 1122 can include openings or recesses 1124 to connect the first openings 1105 to the exterior of the device. In some embodiments, the top cover 1122 can fit over or sandwich the multi-position switch 1103.

After cleaning the tissue within the device, it can be important not to allow inadvertent access to the clean tissue to avoid contamination and to maintain sterile conditions within the device. In some embodiments, the second plate 1107 can be permanently affixed to the container 1118. By affixing the second plate 1107 to the container 1118, a seal can be formed that prevents contamination from entering the device. In some embodiments, the second plate 1107 can be affixed to the container 1118 using adhesives, heat sealing, or fasteners such as screws.

In accordance with various embodiments, the third plate 1108 can be disk-shaped and the one or more third openings 1125 in the third plate can be arranged at the same radial position on the disk or at different radial positions. In some embodiments, the third plate 1108 can rotate while the first plate 1104 and the second plate 1107 are stationary. In some embodiments, the first plate 1104 and second plate 1107 are coupled to sandwich or retain the third plate 1108 between them. As discussed above with reference to FIG. 10A, the one or more third openings 1125 can be surrounded on one or both sides of the third plate 1108 by a seal.

The rotary handle 1121 can extend through the center of the tissue treatment system 1100 and engage with mixing blades (not shown) in the filter 1123 or container 1118. By rotating the rotary handle 1121, tissue within the filter 1123 or container 1118 can be mechanically processed to allow washing or separation of components of the tissue as part of a tissue treatment regimen. In some embodiments, the filter 1123 can be a filter structure as described in greater detail below with reference to FIGS. 16A-18B. In an exemplary embodiment, the filter 1123 can act as a dividing wall or barrier to separate an inner chamber 1140 from an outer chamber 1141.

In some embodiments, the first plate 1104 can include one or more ports to couple tubes to the first openings 1105 of the first plate 1104 similar to the ports 902 described above with reference to FIG. 9A. In some embodiments, the rotary handle 1121 can engage with a seal 1126 that prevents fluids, gases, or tissue components from exiting the filter 1121 or container 1118. In accordance with various embodiments, the seal 1126 can be integrated into the rotary handle 1121 or into the second plate 1107.

The multi-position switch 1103 can cause rotation of the third plate 1108 with respect to the first plate 1104 and the second plate 1107 in some embodiments. The multi-position switch 1103 can include knobs or dials that rotate or can include handles that a user can grip to cause rotation. In some embodiments, a portion of the multi-position switch 1103 can have a complementary shape to a central hole of the third plate 1108. For example, the central hole of the third plate 1108 can be shaped as a pentagon or other polygonal shape and the portion of the multi-position switch 1103 can be shaped as a pentagon that fits within the hole of the third plate 1108. The complementary shapes of the portion of the multi-position switch 1103 and the central hole of the third plate 1108 can enable the multi-position switch 1103 to engage and rotate the third plate 1108 in some embodiments.

In some embodiments, the second plate 1107 can be coupled to the container 1118 using a snap fit or adhesive fit.

Figure 12A:
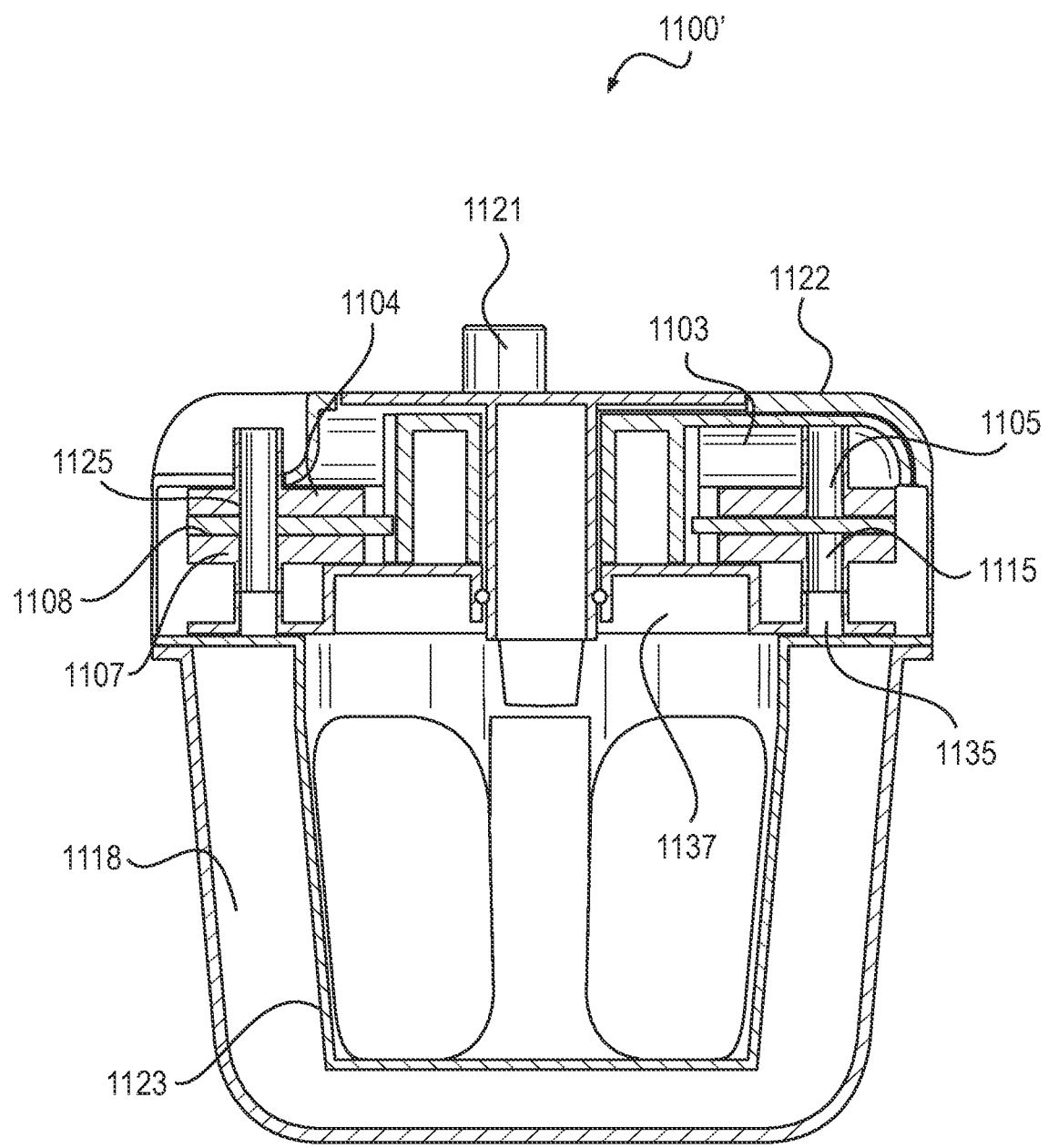
FIG. 12A illustrates a cutaway view of a tissue treatment system including a flow management device subassembly in accordance with various embodiments of the present disclosure.
Figure 12B:
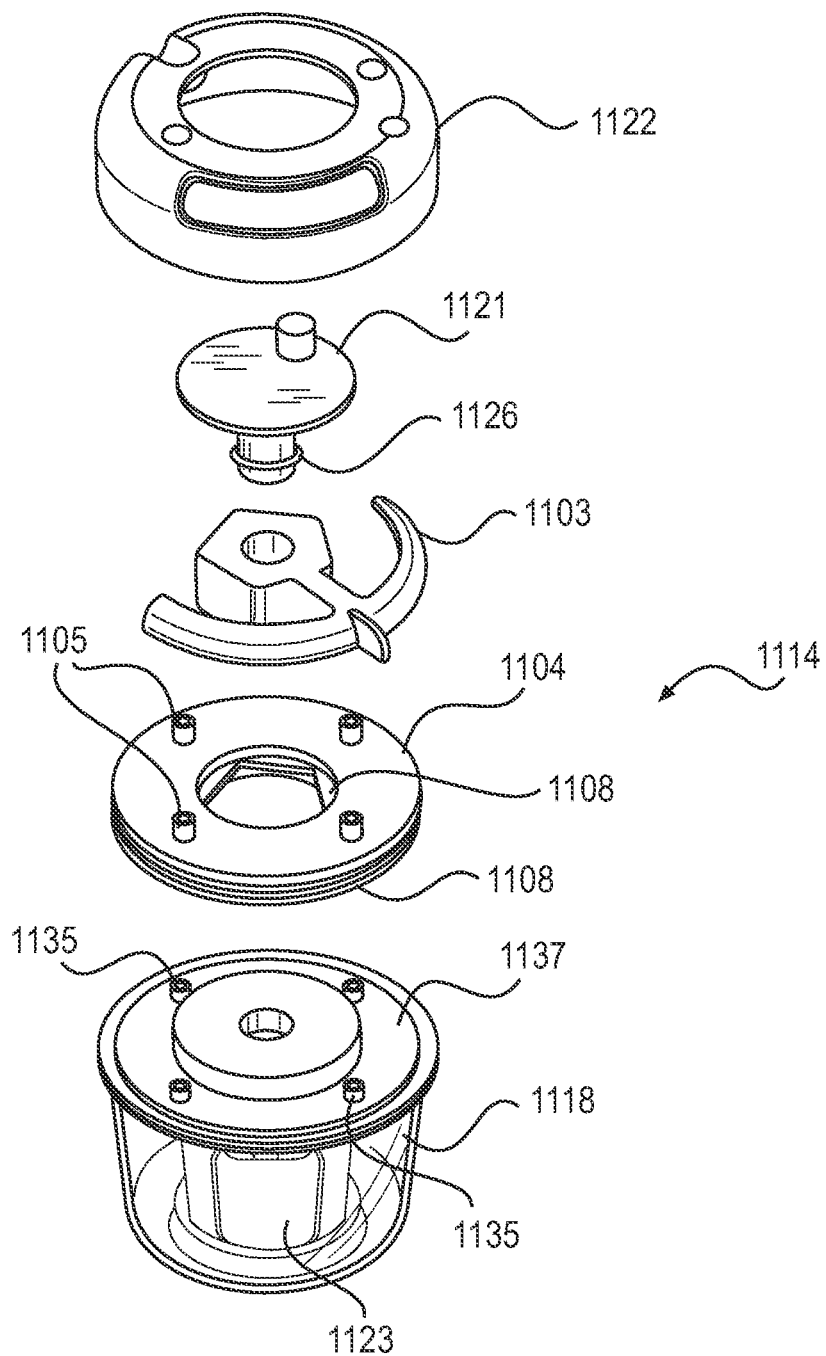
FIG. 12B illustrates an exploded view of the tissue treatment system of FIG. 12A.

FIGS. 12A and 12B show a cutaway view and an exploded view, respectively, of an alternative embodiment of a tissue treatment system 1100' including an integrated flow management device. The flow management device is similar to the flow management device described above with respect to FIG. 10A or 10B. The primary difference between the tissue treatment system 1100 of FIGS. 11A-11B and the tissue treatment system 1100' of FIGS. 12A and 12B relates to component integration and manufacturing. The tissue treatment system 1100' can include a valve assembly 1114 that includes the first plate 1103, the second plate 1107, and the third plate 1108. The tissue treatment system 1100' can also include a filter top 1137 that includes a plurality of third openings 1125 that connect the interior of the container 1118 and the second openings 1115 of the second plate 1107. By operating the multi-position switch 1103 coupled to the third plate 1108, the third openings 1125 can be positioned to allow fluid communication between a subset of the first openings 1105 and a subset of the second openings 1115 thereby also placing a subset of the third openings 1135 in fluid communication with the subset of the first openings 1105.

After cleaning the tissue within the device, it can be important not to allow inadvertent access to the clean tissue to avoid contamination and to maintain sterile conditions within the device. In some embodiments, the filter top 1137, top cover 1122, or both can be permanently affixed to the container 1118. By affixing the filter top 1137 and the container 1118, a seal can be formed that prevents contamination from entering the device. In some embodiments, the filter top 1137, top cover 1122, or both can be affixed to the container 1118 using adhesives, heat sealing, or fasteners such as screws.

The filter top 1137 can be coupled with the filter 1123 using a snap fit or an adhesive fit. In some embodiments, the filter assembly 1114 can be replaceable or interchangeable. In some embodiments, the tissue treatment device 1100' can be provided with multiple filter assemblies 1114 that are configured to correspond to different sets of tissue treatment protocols. In such embodiments, the user can select a filter assembly 1114 to fit their application at the beginning of the procedure and can snap the filter assembly 1114, multi-position switch 1103, rotary handle 1121, and top cover 1122 in place.

Embodiments described above include one or more walls or barriers such as flat plates to restrict or allow flow between the first openings and the second openings. In alternative embodiments described below with respect to FIGS. 13A-14B, different components such as cylindrical spindles or diaphragm values provide the capability to restrict flow between first and second openings.

Figure 13A:
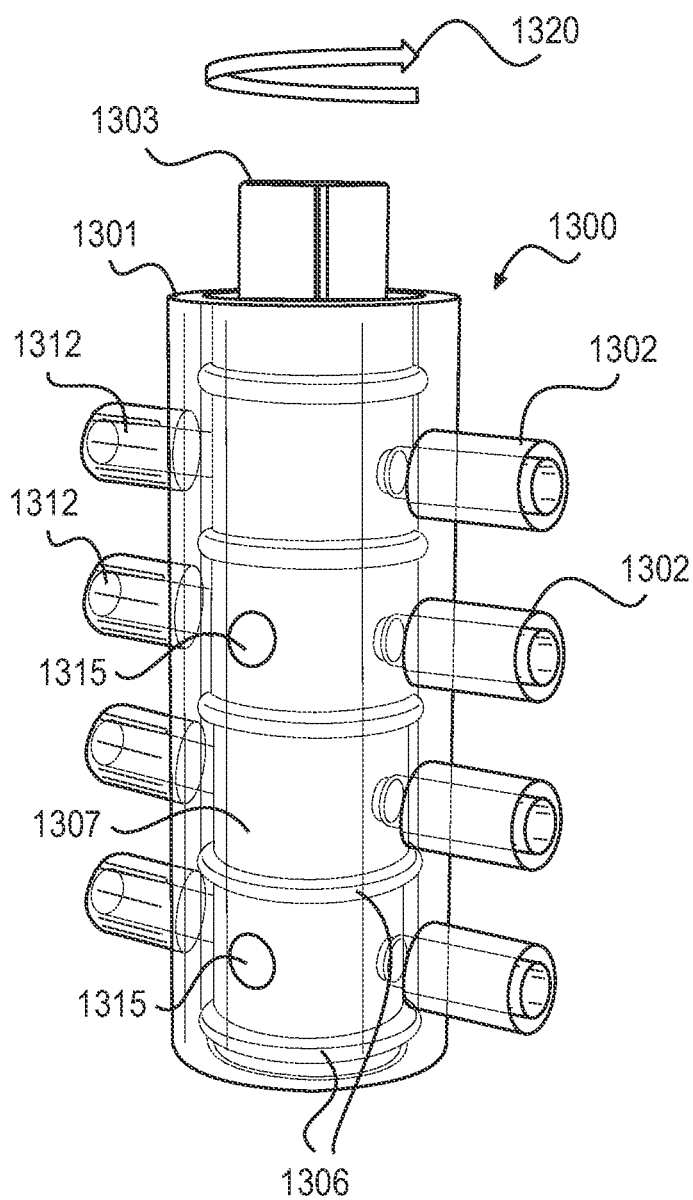
FIG. 13A illustrates a flow management device including a spindle in accordance with various embodiments of the present disclosure.
Figure 13B:
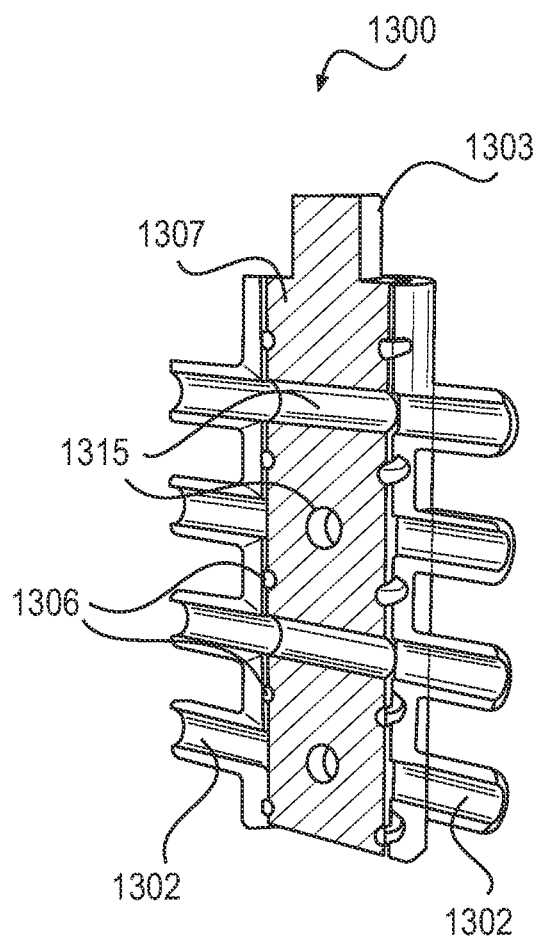
FIG. 13B illustrates a cross-sectional view of the flow management device shown in FIG. 13A.

FIG. 13A depicts a flow management device 1300 including a spindle in accordance with various embodiments of the present disclosure. FIG. 13B illustrates a cross-sectional view of the flow management device 1300. The flow management device 1300 includes a body 1301 having a plurality of first openings 1302 and a plurality of second openings 1312, a spindle 1307 coupled to a multi-position switch 1303 and a plurality of third openings 1315. By operating the multi-position switch 1303, the spindle 1307 can rotate in a direction 1320. Operation of the multi-position switch 1303 can position some or all of the third openings 1315 to place a subset of the first openings 1302 into fluid communication with a subset of the second openings 1312.

In some embodiments, the plurality of third openings 1315 can include more than one opening each axial position of the spindle 1307. In such embodiments, different openings at the same axial position can have different azimuthal trajectories. The use of multiple openings at the same axial position along the spindle 1307 can increase the number of possible connection configurations for a given spindle 1307. According to the rotational orientation of the spindle 1307, each of the third openings 1315 can connect one of the first openings 1302 to one of the second openings 1312.

In some embodiments, seals 1306 may be placed at positions along the spindle 1307 to obstruct the passage of fluid, gas, or tissue material between the spindle 1307 and the body 1301. The seals 1306 can be O-rings, grommets, or gaskets and can be made of rubber, polymer, or any other suitable material. In some embodiments, the seals 1306 can be formed of thermoplastic elastomer using a molding technique such as twin-shot molding.

The multi-position switch 1303 can be integrated directly into the spindle 1307 in some embodiments or can be a separate device that causes the spindle 1307 to rotate. In some embodiments, the multi-position switch 1303 can be operated by hand. In some embodiments, the multi-position switch 1303 can be optimally shaped to enable the use of tools such as wrenches to improve a user's leverage in setting the multi-position switch 1303. Although the multi-position switch 1303 is shown rotating in direction 1320 in FIG. 13A, the multi-position switch 1303 can be rotated in either direction in some embodiments.

The body 1301 can include ports or connections adjacent to the first openings 1305 or the second openings 1315 that allow connection to a variety of different tubes or hoses. For example, the ports or connections adjacent to the first openings 1305 or the second openings 1315 can include barbs, threads, fittings or other appropriate connectors.

Figure 14A:
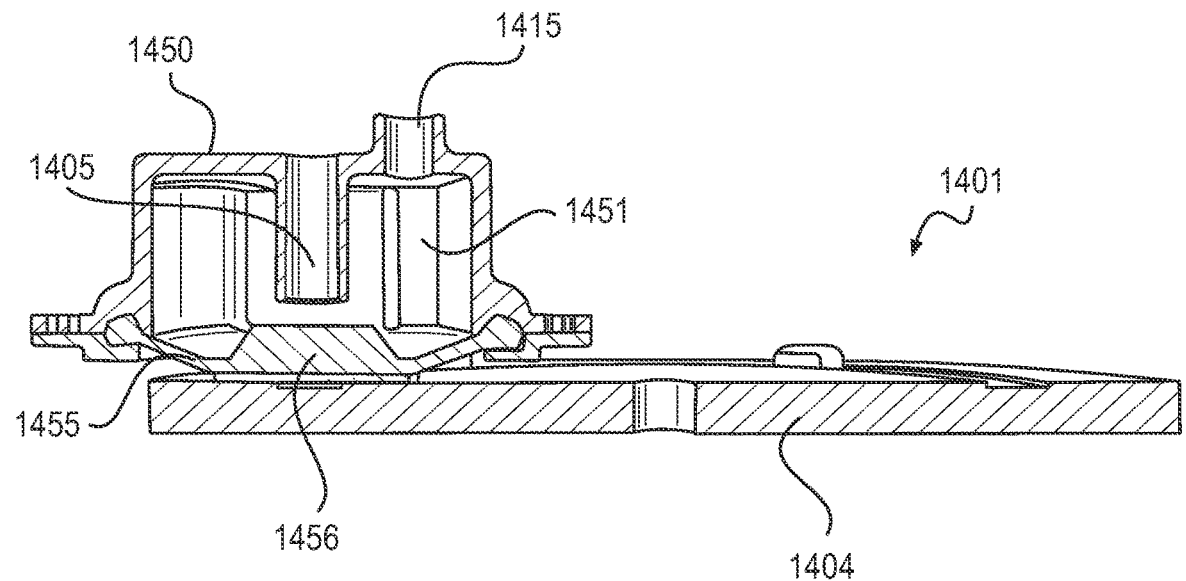
FIG. 14A illustrates a cross-sectional view of a flow management device including a diaphragm valve in an open position in accordance with various embodiments of the present disclosure.
Figure 14B:
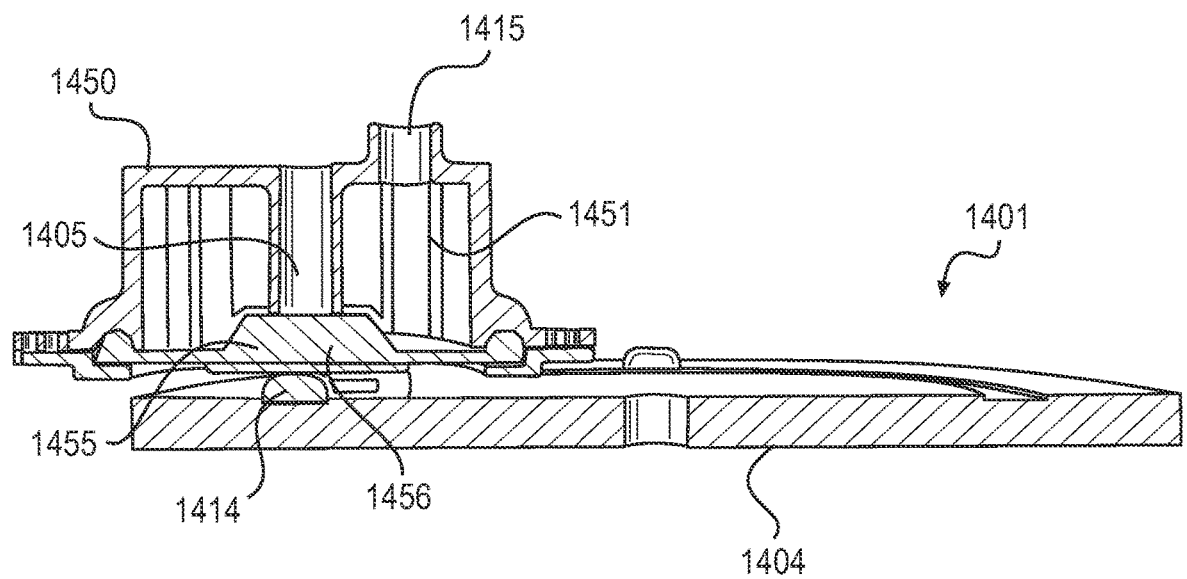
FIG. 14B illustrates a cross-sectional view of the flow management device including a diaphragm valve in a closed position in accordance with various embodiments of the present disclosure.

FIGS. 14A and 14B illustrate a flow management device 1401 including a diaphragm valve in open and closed positions, respectively, according to various embodiments of the present disclosure. The flow management device 1401 can include a rotating plate 1404, and one or more diaphragm units 1450. The diaphragm unit 1450 can include a flexible diaphragm 1455 and an inner chamber 1451. The flexible diaphragm 1455 can be actuated to open or close fluid pathways in the flow management device 1401. In some embodiments, the diaphragm 1450 can include materials such as silicone. In some embodiments, the diaphragm 1455 can include a boss 1456.

In an open position, the diaphragm unit 1450 places a first opening 1405, inner chamber 1451, and second opening 1415 into fluid communication. In a closed position, the first opening 1405 of the diaphragm unit 1450 is no longer in fluid communication with the inner chamber 1451 or the second opening 1415.

The rotating plate 1404 can include one or more protrusions 1414. In some embodiments, the rotating plate 1404 can be rotated to different rotational positions with respect to the diaphragm units 1450. By rotating the rotating plate 1404, a protrusion 1414 can be positioned below the diaphragm unit 1450. The protrusion can force the flexible diaphragm 1455 upwards to seal the boss 1456 against the one or more first openings 1405 passing through the diaphragm unit 1450 thereby placing the diaphragm unit 1450 in a closed position. By sealing the one or more first openings 1405, the diaphragm 1450 can interrupt fluid communication between the first openings 1405 and second openings 1415.

In some embodiments, a separate diaphragm unit 1450 can be supplied for each fluid connection that is to be controlled. In some embodiments, a single diaphragm unit can include more than one boss 1456, more than one first opening 1405, or more than one second opening 1415. In some embodiments, rotating plate 1404 can have small patterns of protrusions 1414 at different azimuthal positions on the plate 1404 to simultaneously provide control of multiple diaphragm units 1450 for each position of the rotating plate 1404.

In FIG. 15A, a tissue treatment system 1530 is illustrated that includes a turbine 1520 in accordance with various embodiments. The turbine 1520 can turn the mixing shaft 1535 including mixing blades or paddles 1534 to agitate the tissue inside the tissue treatment system. The turbine 1520 can include a rotor with a central shaft 1521 and rotor blades 1528 as shown in FIG. 15C. In some embodiments, the turbine 1520 can have an air intake 1522 and air outlet 1525. Upon attachment of the air outlet 1525 to a source of negative pressure such as a vacuum pump, the rotor blades 1528 will move thus turning the central shaft 1521.

As shown in FIG. 15B, the end 1526 of the central shaft 1521 can engage with the mixing shaft 1535 so that the central shaft 1521 and mixing shaft 1535 rotate in concert. In accordance with various embodiments, the engagement of the central shaft 1521 with the mixing shaft 1535 can take any suitable form. For example, as shown in FIG. 15B, the end 1526 of the central shaft 1521 can have a hexagonal cutout that matches a hexagonal extension on the mixing shaft 1535. Other shapes are also possible including squares, stars, and other polygons. In some embodiments, the turbine 1520 can be separated from the base of the tissue treatment system 1530, and a manually operated rotation system such as a rotary handle can be installed in its place. In some embodiments, the separable turbine 1520 can be sterilizable or reusable to allow use of a single turbine 1520 for multiple tissue processing procedures with multiple tissue treatment canisters or containers. In some embodiments, the turbine 1520 can be disposable.

Because a solution including washing fluids and adipose or other tissues can be viscous, a user that is manually agitating the tissue may become fatigued before the washing sequence is complete. In addition, the agitation may be inconsistent if the user varies the speed of rotation of the rotary handle throughout the washing sequence. Rotation of the mixing shaft 1535 using a turbine 1520 can improve consistency of mixing. For example, a constant level of negative pressure applied at the air outlet 1525 can cause the mixing shaft 1535 to rotate at a constant rate of rotation. In addition, the turbine 1520 can operate at a consistent speed for an extended period of time as necessary according to the needs of the practitioner.

Figure 15D:
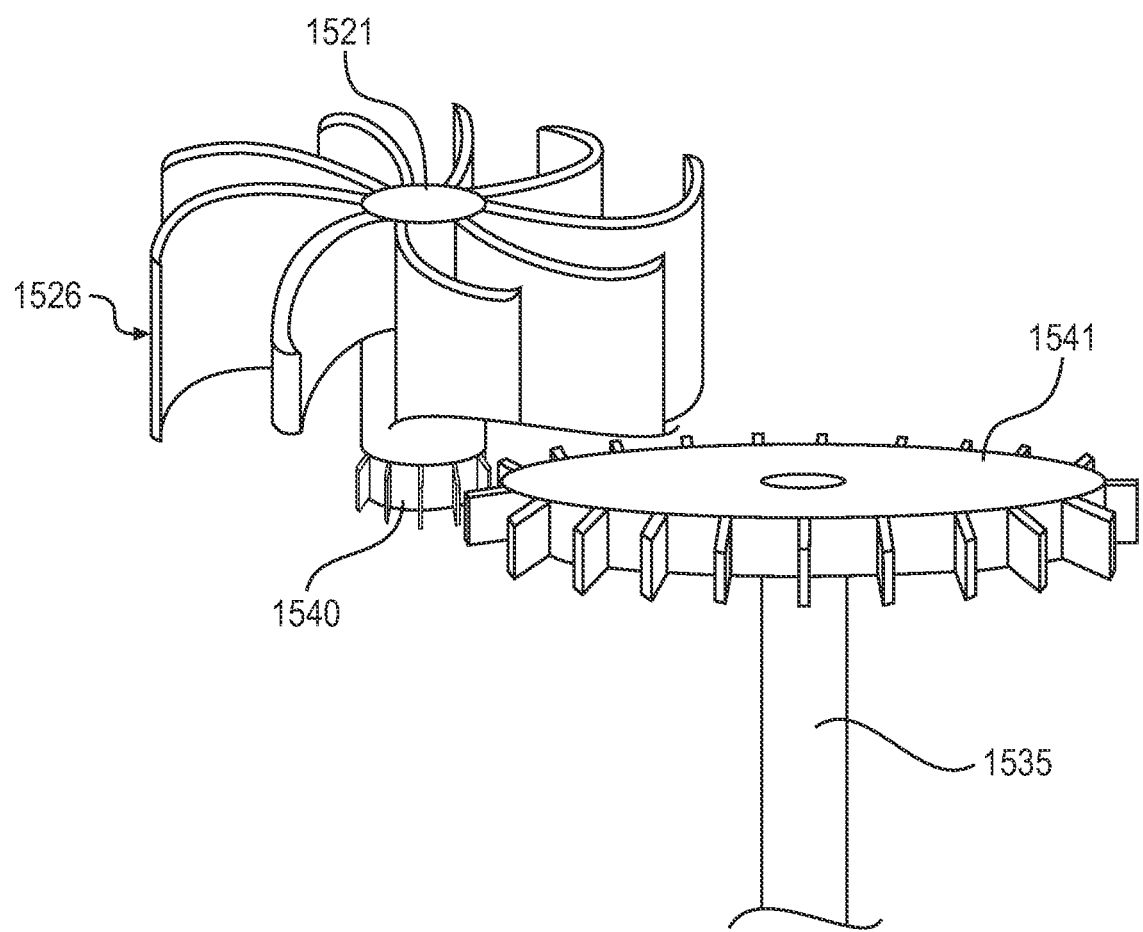
FIG. 15D illustrates engagement of a turbine with a mixing shaft through a gear system in accordance with various embodiments of the present disclosure.

FIG. 15D illustrates a modification to the turbine wherein a smaller gear 1540 is attached to the central shaft 1521. The teeth of the smaller gear 1540 can engage with teeth on a larger gear 1541 attached to the mixing shaft 1535. In some embodiments, the ratio of sizes of the smaller gear 1540 and the larger gear 1541 can be chosen to optimize rotations per minute of the mixing shaft 1535 for adipose tissue washing. In some embodiments, the tissue treatment system 1530 can include multiple removable and attachable small gears 1540 or large gears 1541 to enable a practitioner to tune the gear ratio and, thus, the speed of rotation to the desired level.

Figure 16:
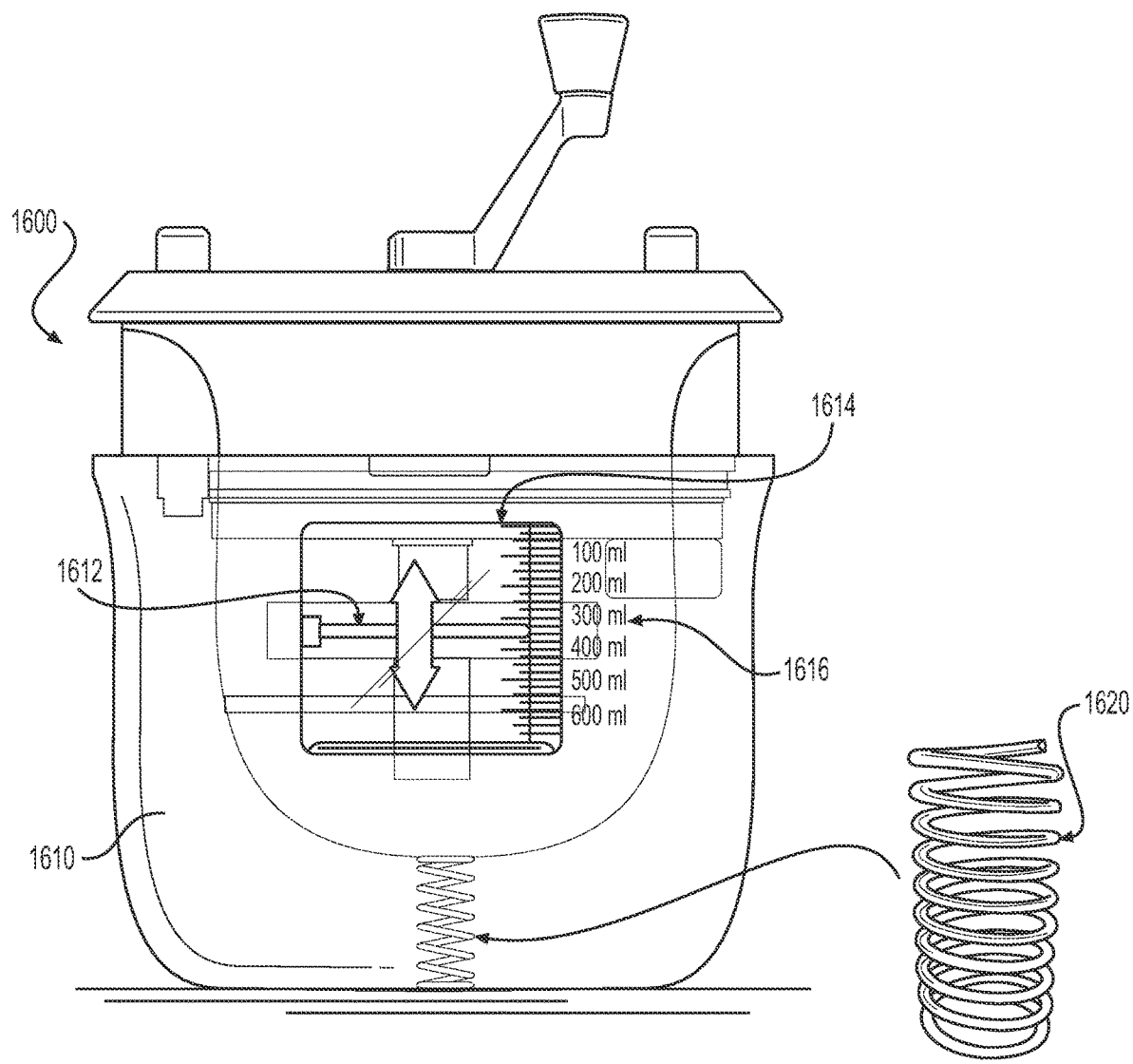
FIG. 16 illustrates a tissue treatment system including a volume measurement device in accordance with various embodiments of the present disclosure.

FIG. 16 illustrates a tissue treatment system 1600 including a volume measurement device 1610 in accordance with various embodiments of the present disclosure. In some embodiments, the volume measurement device 1610 can include a spring 1620 and needle gauge 1612. In accordance with various embodiments, the spring 1620 can be calibrated to compress by a specific distance for a given applied force. The spring 1620 can be placed below a vessel that holds the tissue in the tissue treatment system. For a given weight of tissue in the tissue treatment system 1600, the spring 1620 can compress a prescribed distance, and the needle gauge 1612 can indicate the mass of tissue present. In some embodiments, the needle gauge 1612 can be visible through a window 1614 in the exterior wall of the tissue treatment system 1600. In some embodiments, the needle gauge 1612 can indicate values on a scale 1616. The scale 1616 can be labeled in mass units or volume units.

Figure 17B:
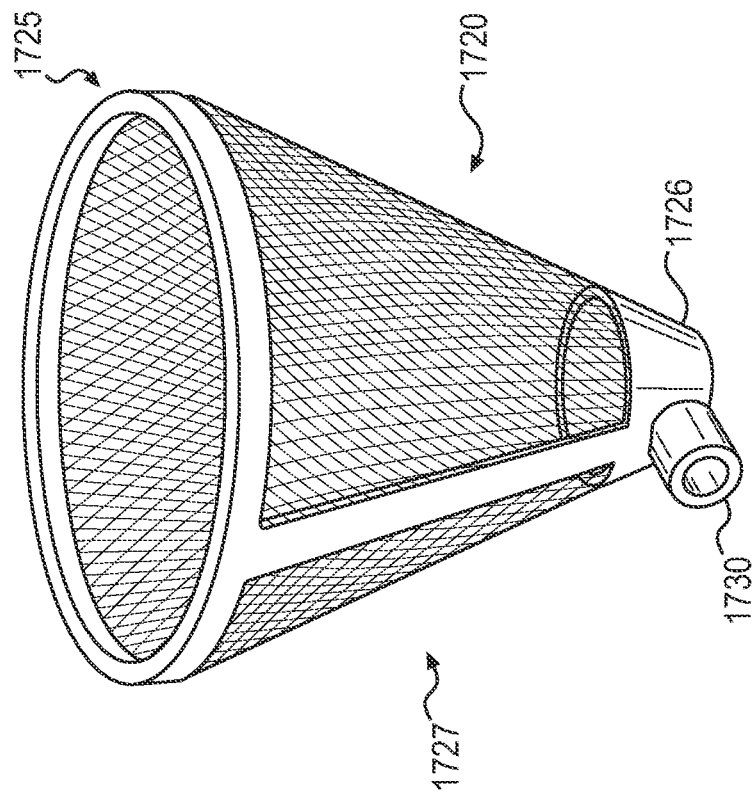
FIGS. 17A and 17B illustrate various mesh filters for use in tissue treatment systems according to various embodiments of the present disclosure.
Figure 17A:
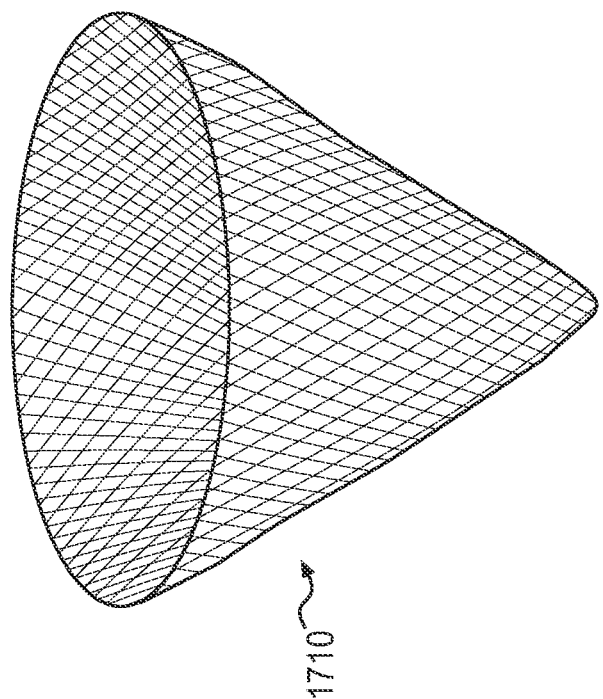

FIGS. 17A and 17B illustrate one embodiment of a filter structure that can divide first and second portions or chambers of the devices and systems described herein. The dividing wall defined by the filter structure can include a frame member 1725 that provides structural support. Frame member 1725 can be formed of a material that provides rigidity and is formed from solid material. In one aspect, the frame member 1725 is formed of liquid-impervious material. Frame member 1725 can mate with or be formed integral with a top portion of the device. For example, the frame member 1725 can mate with or be formed integral to a second plate 1107 as described above with reference to FIG. 11A. The bottom portion 1726 of the frame member 1725 can define a transfer port 1730 for removal of materials from within the inner chamber of the device adjacent to the bottom portion of the device. In one aspect, frame member 1725 extends from the top portion of the interior of the device to the bottom of the interior of the device. In some embodiments, the frame member 1725 can surround an upper border of the filter 1710 or mesh wall. In additional embodiments, the frame member 1725 can extend along at least a portion of a side wall of the mesh wall to a bottom portion of the mesh wall.

Frame member 1725 can include a window 1727 defined by the frame member. Various filters 1710 can be mated with the frame member to allow movement of liquid and gas from between the inner and outer chambers of the device. The filter 1710 can be mated within one or more windows 1727. For example, as shown in FIG. 17B, a window defined between the top and bottom portions of the frame member can include a filter 1710. The filter 1710 can define a portion of the dividing wall that divides the first and second chambers of the device. In one embodiment, the filter and/or filter windows do not extend to the top most part and/or bottom most part of the frame member. Alternatively, a single filter 1710 can be seated within the frame member. In some embodiments, the filter 1710 can be a mesh wall supported by the frame or frame member that acts to divide the first chamber from the second chamber.

In some embodiments, a mesh filter 1710 as shown in FIG. 17A can have a conical shape. In various embodiments, the narrow end of the mesh filter 1710 can come to a point or a line seam, or the mesh filter 1710 can have a flat panel on the bottom. In some embodiments, the cone shape of the mesh filter 1710 can smooth out areas where adipose tissue or other tissue components can get stuck. As shown in FIG. 17B, a mesh filter 1720 can also include a superstructure 1725 to provide greater form and stability to the mesh filter 1720. In some embodiments, the superstructure of the frame member 1725 can be overmolded plastic. In some embodiments, the mesh filter 1720 can include an integrated transfer port 1730. The transfer port 1730 can be used to extract tissue from a tissue treatment system after washing, separating, and mixing cycles are complete.

Figure 17C:
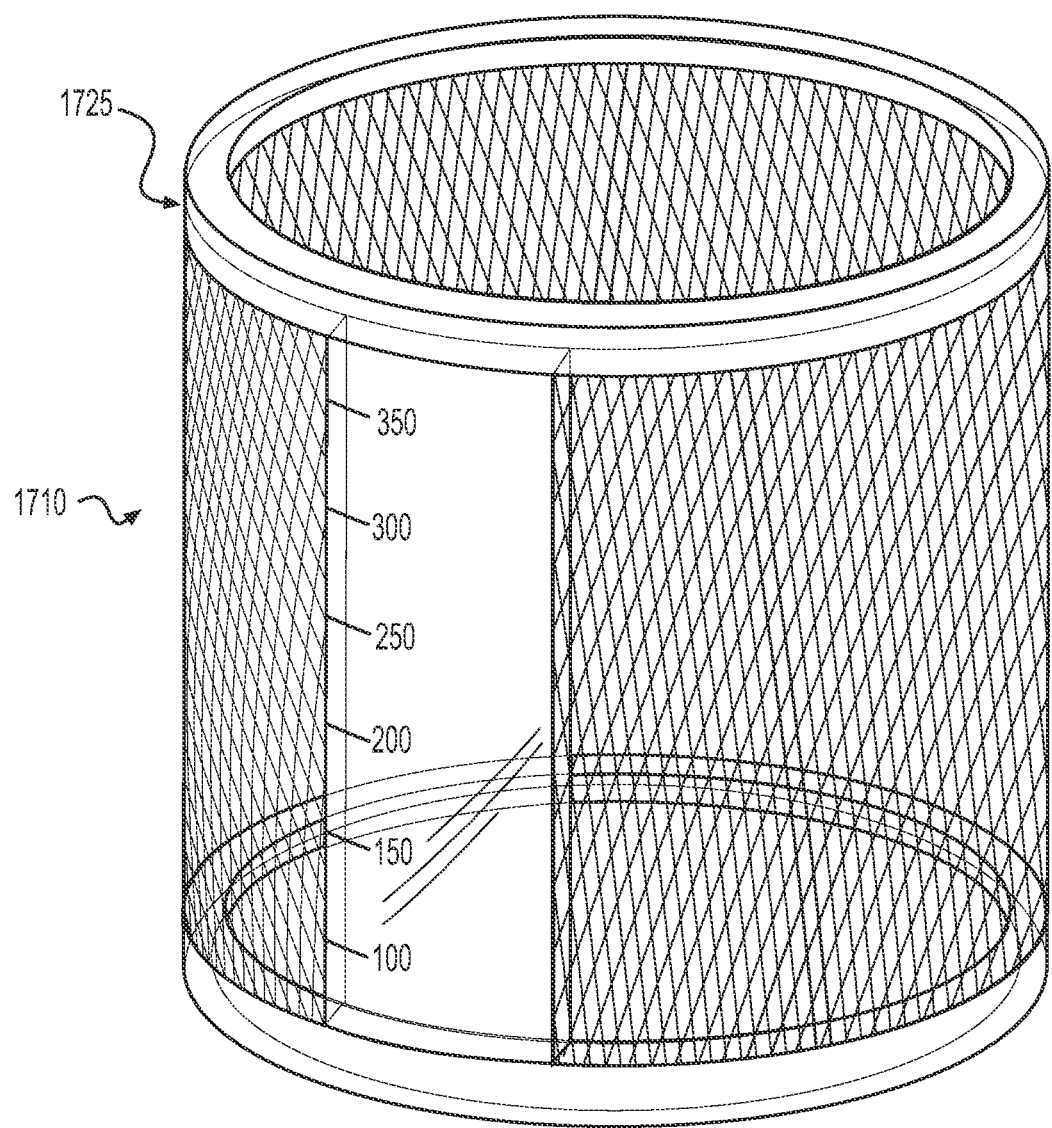
FIG. 17C illustrates a straight-walled mesh filter according to various embodiments of the present disclosure.

FIG. 17C illustrates a straight-walled mesh filter according to various embodiments of the present disclosure. Use of a straight-walled mesh filter can allow use of mixing blades of equal length from top to bottom of the shaft. The frame member 1725 of the mesh filter 1710 can promote a "squeegee" effect to help remove material from the mesh filter 1710 and reduce waste during extraction. In some embodiments, the frame member 1720 can include a transparent material to improve visibility of the contents within the mesh filter 1710.

FIGS. 18A and 18B illustrate a disassembled and assembled filter structure 1810, respectively, according to various embodiments of the present disclosure. The filter structure 1810 can include a frame member 1850 and a filter 1815. The frame member 1850 can include one or more windows 1827. In some embodiments, the filter 1815 can be mated within the windows 1827.

In some embodiments, the filter 1815 can include cut-through holes 1816 to hold the filter in place against the frame member 1850. In some embodiments, the frame member 1850 can include a boss feature 1856 or other catch feature to engage with the cut-through holes 1816 and position the filter 1815. In accordance with various embodiments, the filter 1815 can be cut to fit the frame member 1850 such that removed portions 1818 of the filter 1815 line up with solid portions 1858 of the frame member 1850. In some embodiments, the solid portions 1858 comprise extensions from the frame member 1850. The frame member 1850 can surround an upper border of the filter 1815 and have multiple solid portions 1858 as extensions along at least a portion of a side wall of the mesh wall to a bottom portion of the mesh wall. In accordance with various embodiments, the filter 1815 can include a synthetic or natural mesh-like material.

The filter structure 1810 can include a transfer port 1860 near the bottom of the filter structure. In prior systems, removal of cleaned tissue from the tissue treatment system generally required inversion of the tissue treatment system to bring the tissue in proximity to an entry/exit port at the top of the device. In this case, inversion of the device is undesirable as it requires the device to be completely disconnected from attached tubing and awkwardly held upside-down by a practitioner. Alternatively, a separate port having an extension tube was used to extract clean tissue from the device. In this case, the tube typically presented an obstruction to the motion of the mixing blades, and tissue trapped near the tube did not properly wash or mix. In embodiments of the present disclosure, the transfer port 1860 can allow removal of tissue from the tissue treatment system through or near the bottom of the container. The tissue can be drawn into the transfer port 1860 by gravity or through the application of negative pressure. In some embodiments, the transfer port 1860 can be used to extract fluids, gases, or solids or can be used to insert fluids, gases, or solids. In certain embodiments, the transfer port 1860 can be in fluid communication with the inner chamber of a tissue treatment device as described above with reference to FIGS. 11A and 12A. In other embodiments, the transfer port 1860 can be in fluid communication with the outer chamber of the tissue treatment device. In some embodiments, a portion of the transfer port 1860 can be equipped to engage with syringes of various sizes, luer locks, or any other suitable connector 1861.

Figure 18C:
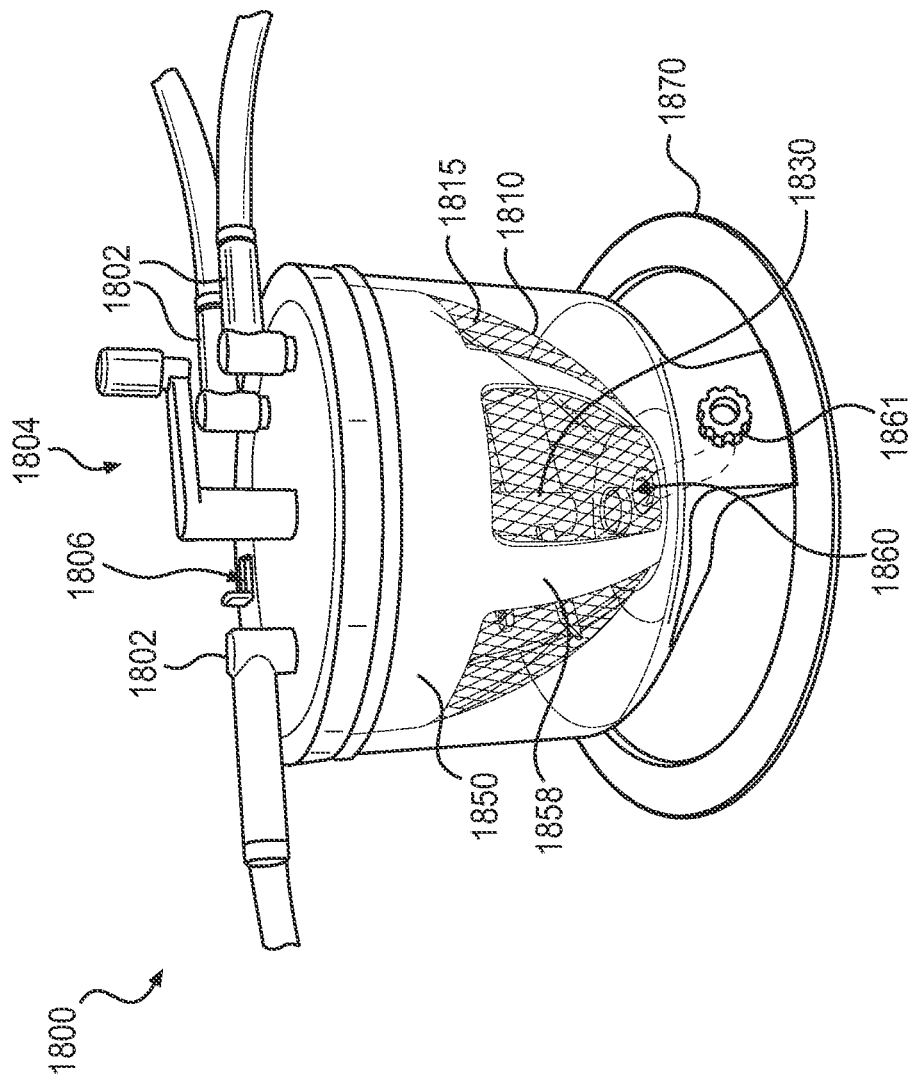
FIG. 18C illustrates a tissue treatment system including a filtering structure.

FIG. 18C illustrates a tissue treatment system 1800 including a filter structure 1810 in accordance with various embodiments described herein. The tissue treatment system 1800 can include a plurality of ports 1802, one or more mixing blades 1830, a base 1870, and a filter structure 1810.

As described above with reference to FIGS. 18A-18B, the filter structure can divide first and second portions or chambers of the tissue treatment system 1800. The dividing wall defined by the filter structure 1810 can include a frame member 1850 that provides structural support. In various embodiments, frame member 1850 can mate with or be formed integral with a top portion of the device. For example, the frame member 1850 can mate with or be formed integral to a second plate 1107 as described above with reference to FIG. 11A. In some embodiments, the filter structure, top portion, and bottom portion of the device including a transfer port 1860 can be built into one interior wall of the device. The bottom portion of the frame member 1850 can define a transfer port 1860 for removal of materials from within the inner chamber of the device adjacent to the bottom portion of the device. In one aspect, frame member 1850 extends from the top portion of the interior of the device to the bottom of the interior of the device. In some embodiments, the frame member 1850 can surround an upper border of the filter 1815 or mesh wall. In additional embodiments, the frame member 1850 can extend along at least a portion of a side wall of the mesh wall to a bottom portion of the mesh wall.

The manual forces that are applied to operate the handle 1804 to properly mix and wash tissue using the mixing blade(s) 1830 may be significant for some forms of tissue. In a typical setup, tissue washing and mixing will occur after other steps in a surgical procedure have already been performed such as tissue extraction. Mid-operation, the examination gloves worn by the surgeon or practitioner may contain foreign matter or fluid of a slippery nature that can make it difficult to grasp and operate the handle without tipping over the device. In accordance with various embodiments, the tissue treatment system 1800 can include a wide base 1870 (or 917 in FIG. 9A) at the bottom of the system to improve stability and prevent tipping or movement of the device during tissue mixing and washing. In some embodiments, the underside of at least a portion of the wide base 1870, 917 can include a high-friction, textured, or tacky substance such as rubber to prevent slipping or skidding of the tissue treatment system 1800 during use. In some embodiments, the wide base 1870, 917 can include fluids, metals, or other high density materials to provide additional weight to the base.

The wide base is illustrated with a couple of specific configurations, but it should be understood that the base can be modified to accomplish any one or more of maintaining device stability and preventing accidental tipping or movement. The base can include a flared outward section or other configurations (e.g., a box, a series of extensions, or multiple legs). The base can be defined by a widened section, for example, having a footprint or widest dimension that is 10%, 20%, 30%, 40% or more greater than the widest dimension of the lowest portion of the container of the treatment system, or 10%, 20%, 30%, 40% or more greater than the widest dimension of the top of the treatment system (thereby preventing a top-heavy or unstable structure).

In some embodiments, the tissue treatment device 1800 can include a multi-position switch 1806. The multi-position switch can operate to place different subsets of first openings in fluid communication with subsets of second openings as described above with reference to FIGS. 9A-12B.

FIG. 19A illustrates an exploded view of a conical filter structure 1910 for use in tissue treatment systems according to various embodiments of the present disclosure. Although illustrated in conjunction with a particular treatment system, the filter structure can be incorporated with any of the aforementioned tissue treatment systems described herein. As discussed further below, the filter structure can include a filtering portion or mesh structure that allows flow of fluid or debris of a selected size, while retaining tissue to be treated and/or implanted. In addition, the structure includes a frame, which can include a rigid, semi-rigid, or otherwise strong material to support the structure. The frame and filtering portion or mesh, together provide important advantages.

For example, known filters, such as polymeric meshes, may be prone to breakage, especially with vigorous washing or transfer processes. Accordingly, the frame, in its various possible configurations, allows a more robust structure that is less prone to failure during surgical processing. In addition, the filter can extend towards or all the way to the bottom of the treatment system. The extension to the bottom of the treatment system can allow formation of supporting side walls in the frame, and can allow further support of the filter by the bottom wall of the system. In addition, the filter, by extending toward the bottom of the system and including a frame, which itself can extend to and form a bottom portion of the filter, can be configured to engage with one or more transfer ports, thereby allowing insertion and/or extraction of fluids and tissue from the system's bottom— thereby obviating the need for top-only access using syringes or other devices.

Specific details of an exemplary filter are described as follows, but the general principals of the desirable filter structure can be understood from the foregoing and can be applied to filters used in any of the presently described tissue treatment systems and methods. The filter structure 1910 can include a filter 1915 and one or more rigid rings. In an exemplary embodiment, the filter 1915 can be formed of a single piece of material such as a mesh-like material that is sealed at a single seam. By using a single seam, the amount of mesh sealing that has to be performed during production can be reduced. In some embodiments, the filter structure 1910 can include an upper rigid ring 1922 and a lower rigid ring 1924. The upper rigid ring 1922 can include a sealing surface 1924 and a ridge 1925. In various embodiments, the sealing surface 1924 can be flat to allow for heat sealing or ultrasonic welding of the filter 1915 to the sealing surface 1924. The lower rigid ring 1924 can include a flat surface to facilitate heat sealing or ultrasonic welding of the filter 1915 to the lower rigid ring 1924. The rigid rings can be formed of plastic or any other suitable material including, but not limited to, metals or glass. In some embodiments, the filter 1915 can include a synthetic or natural mesh-like material. The filter 1915 can be a mesh wall that divides a first chamber from a second chamber. In some embodiments, the upper rigid ring 1922 can be a portion of a frame that surrounds the upper border of the filter 1915 such as a mesh.

FIG. 19B illustrates placement of the filter structure of FIG. 19A in a tissue treatment system according to various embodiments of the present disclosure. In some embodiments, the tissue treatment system can include an exoskeleton 1950. In an exemplary embodiment, the ridge 1925 on the upper rigid ring 1922 can engage with a shelf feature 1952 in the exoskeleton 1950. The engagement of the upper rigid ring 1922 and exoskeleton 1950 can include a sealing or press-fit step to let an assembler or practitioner know that the elements are engaged. In some embodiments, the lower rigid ring 1924 can be bonded or heat sealed to the exoskeleton 1950 to fix the mesh filter 1910 in place or to prevent leakage of tissue or fluids from within the mesh filter.

FIG. 19C illustrates a cross-sectional view of a filtering structure 1910 according to embodiments of the present application. The filtering structure 1910 can include the filter 1915, the upper rigid ring 1922, and an elastomeric O-ring 1932. The upper rigid ring 1922 can have a recess 1931 such as a groove. The elastomeric O-ring 1932 can be sized to fit tightly within the recess 1931. By pinning the filter 1915 in the recess 1931 using the elastomeric O-ring 1932, a tight seal is formed at the top of the filtering structure 1910 through which solids cannot pass in some embodiments.

FIGS. 19D and 19E illustrate a pre-form 1965 for a filtering structure 1910 and the finished filtering structure 1910, respectively, in accordance with various embodiments of the present application. The pre-form 1965 can be produced in a variety of suitable shapes. In some embodiments, the pre-form 1965 can have an axis of symmetry 1966 about which the pre-form can fold to produce the finished filtering structure 1910. Because the pre-form 1965 is typically a single flat piece of material, it can be manufactured using less complex machining techniques such as punching or die-cutting. In some embodiments, the pre-form 1965 can be folded and sealed to form the filtering structure 1910. For example, the edges 1966 of the pre-form 1965 can be heat-sealed, crimped, or pressed to achieve a seal that will not allow passage of solid materials. As a result, the filtering structure 1910 can have a pocket-like shape akin to a coffee filter in some embodiments.

FIGS. 20A and 20B illustrate two configurations of telescoping mixing paddles for use in tissue treatment systems according to various embodiments of the present disclosure. In accordance with various embodiments, the telescoping mixing paddle 2010 can convert to operate as both mixing paddles and as a piston or plunger. In an exemplary embodiment, the telescoping mixing paddle 2010 has blades at a first axial position 2012 and a second axial position 2014. In some embodiments, blades at different axial positions can rotate with respect to one other during the conversion from mixing form and piston form. Although the telescoping mixing paddle 2010 shown in FIGS. 20A-20D has blades at two axial positions, it is contemplated that blades could be at any number of axial positions along the paddle. The mixing paddle 2010 can be converted to a piston form as shown in FIG. 20B by bringing the blades at the first axial position 2012 and blades at the second axial position 2014 together at the same axial position. This can be accomplished by moving the blades at the first axial position 2012, the blades at the second axial position 2014, or both. In an exemplary embodiment, the piston form of the mixing paddle 2010 can have a complete bottom surface without significant gaps in the surface that would allow tissue to pass through.

FIGS. 20C and 20D illustrate side views of tissue treatment systems with telescoping mixing paddles in accordance with various embodiments. The telescoping mixing paddle 2010 is shown in mixing form in FIG. 20C and piston form in FIG. 20D. At the end of a tissue washing cycle, the piston form of the telescoping mixing paddle 2010 can be used to help extract tissue from the tissue treatment system. In the piston form, a user can press on an end 2015 of the telescoping mixing paddles in the piston form to force tissue towards an extraction port 2030 in the tissue treatment system.

FIGS. 21A-21D illustrate telescoping mixing paddles for use in tissue treatment systems according to various embodiments of the present disclosure. As shown in FIG. 21A, the telescoping mixing paddles 2110 can include a release button 2116 on an end 2115 of the paddles. In some embodiments, the release button 2116 can release a detent that allows the blades at different axial positions along the telescoping mixing paddle to be brought to the same axial position to form a piston or plunger. In some embodiments, the telescoping mixing paddles 2110 can be used in cooperation with mesh filter 2150 including a rigid molded exoskeleton 2152 and a mesh 2155. The rigid molded exoskeleton 2150 can give structure to the mesh filter 2150 that keeps the mesh 2155 in close contact with the outer edge of the blades of the telescoping mixing paddles 2110. The close contact between the blades and the mesh can enable efficient plunger action when the telescoping mixing paddles 2110 are in the piston form thereby improving extraction. FIG. 21B illustrates the telescoping mixing paddles 2110 in the expanded mixing or agitation mode to mix harvested fat and/or other tissue with cleaning or rinse solutions. FIG. 21C illustrates conversion of the telescoping mixing paddles 2110 from mixing mode to piston mode. In this embodiment, blades at the second axial position are raised up to the first axial position. In some embodiments, the blades can be locked in this position to assist in extracting rinsed and cleaned tissue. In FIG. 21D, the telescoping mixing paddles 2110 in the piston form can be pushed down to force the tissue to exit via an extraction port at the bottom of the device.

FIGS. 22A and 22B illustrate a tissue treatment system including a mixing device with a disc portion that can be opened or closed for use as an ejection piston in accordance with various embodiments of the present disclosure. The tissue treatment system 2200 can include a mesh canister 2250 into which a central shaft 2220 passes. The central shaft 2220 can include mixing blades 2230, a disc portion 2240, a handle 2214, and a rotating top lever 2212. During mixing and cleaning of tissue, open portions 2242 of the disc portion 2240 can allow tissue to travel through the disc portion. When the tissue has been cleaned and is ready for extraction, the central shaft 2220 can be slid up similar to a French press. In an exemplary embodiment, the rotating top lever 2212 can be rotated to place solid panels 2243 in the open portions 2242 of the disc portion 2240 thereby blocking the open portions. To enhance tissue extraction, the now solid disc portion 2240 can be lowered by pressing down on the central shaft 2220 to force tissue out of an extraction port 2260 at the bottom of the canister 2250.

Figure 23:
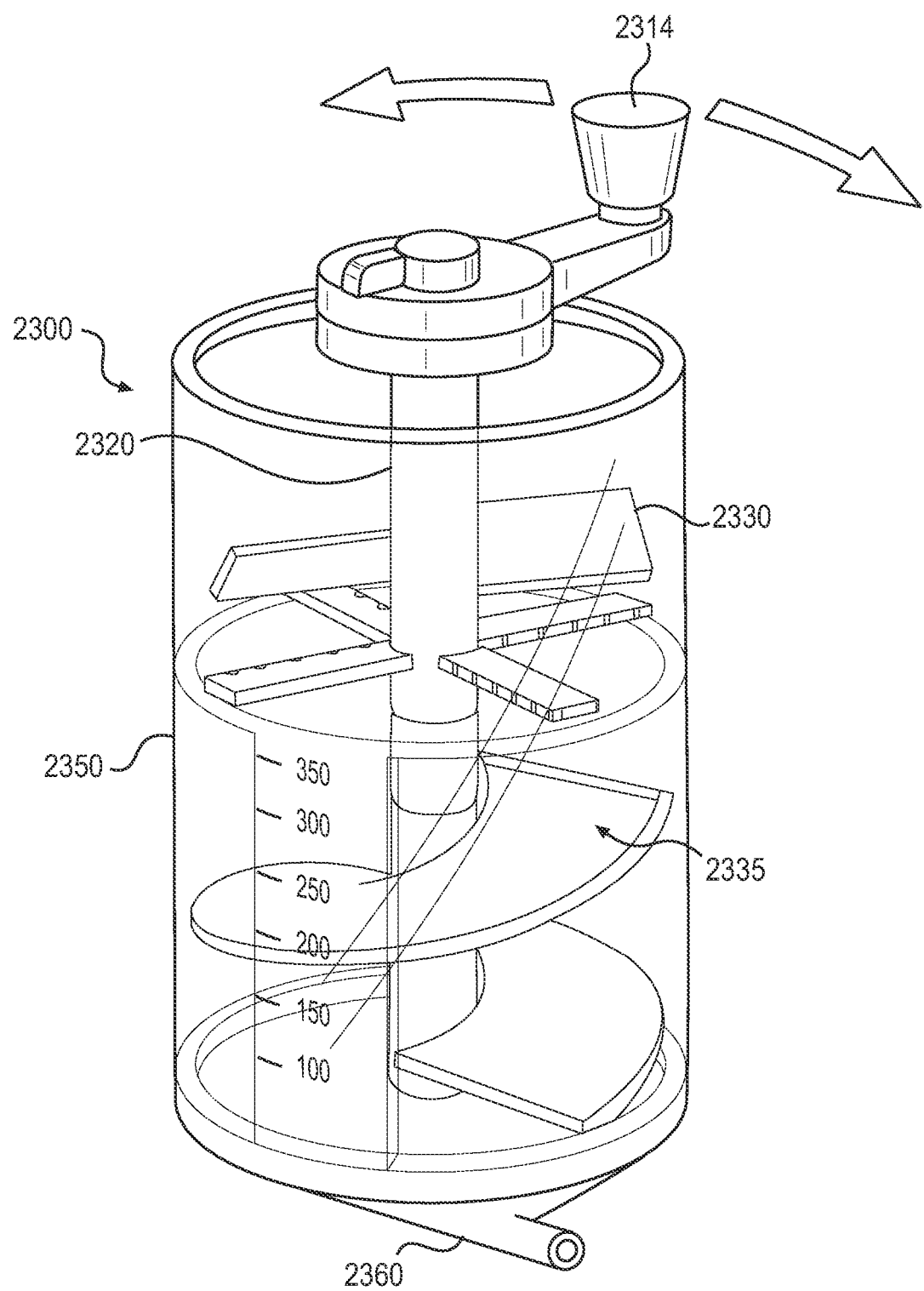
FIG. 23 illustrates a tissue treatment system with a mixing and auger system to facilitate tissue extraction in accordance with various embodiments of the present disclosure.
Figure 24B:
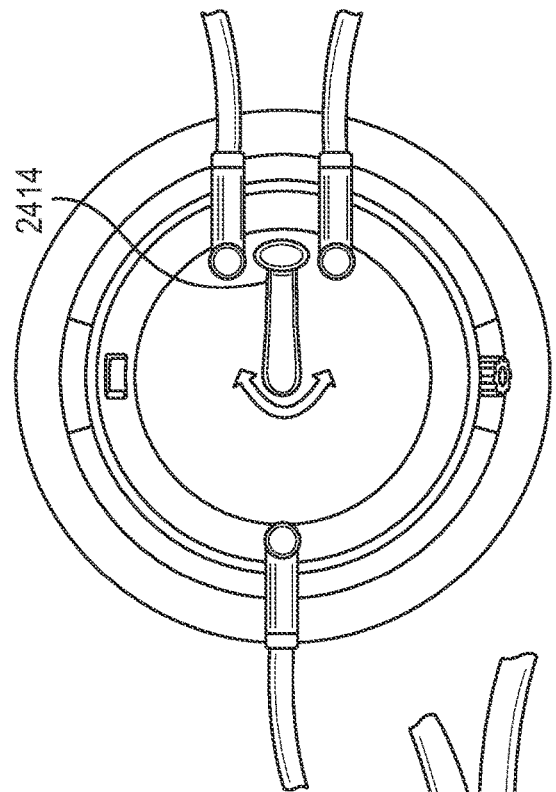
FIGS. 24A and 24B illustrate perspective and top views of the mixing and auger system of FIG. 23 in a tissue treatment system in accordance with various embodiments of the present disclosure.
Figure 24A:
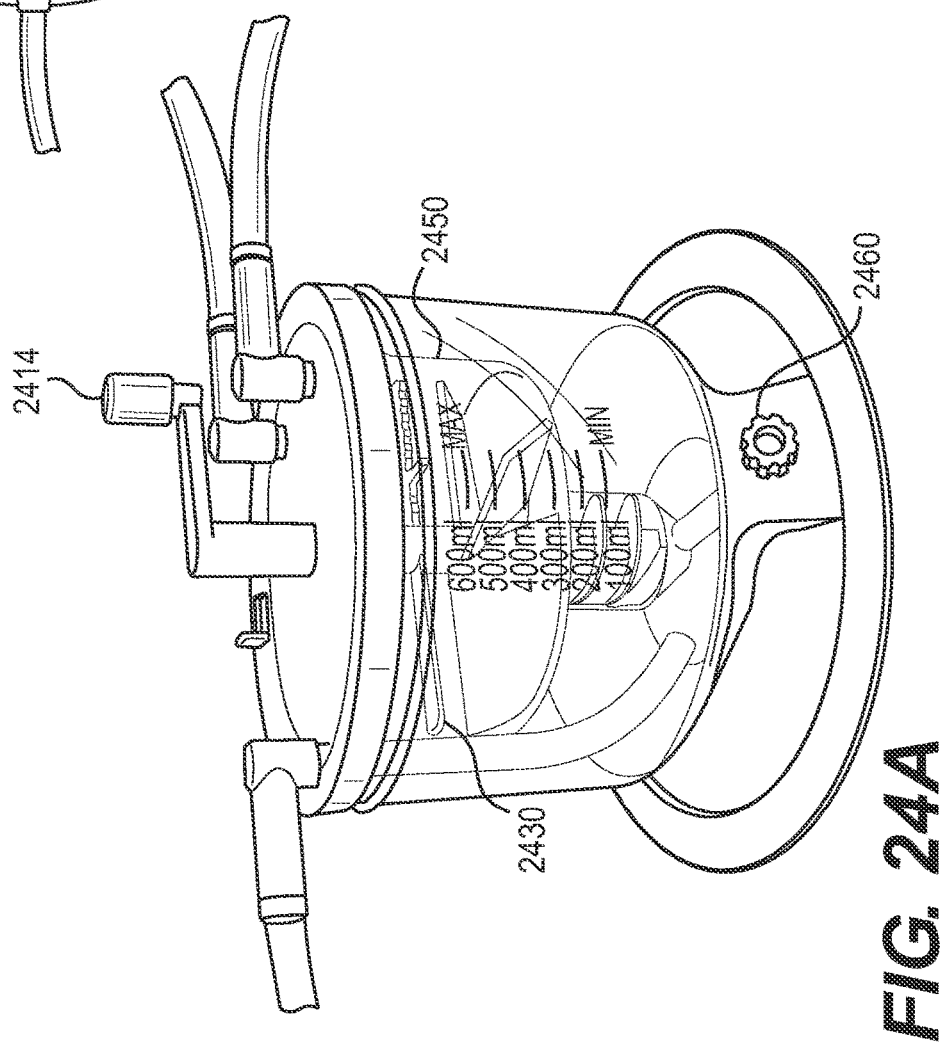
Figure 25B:
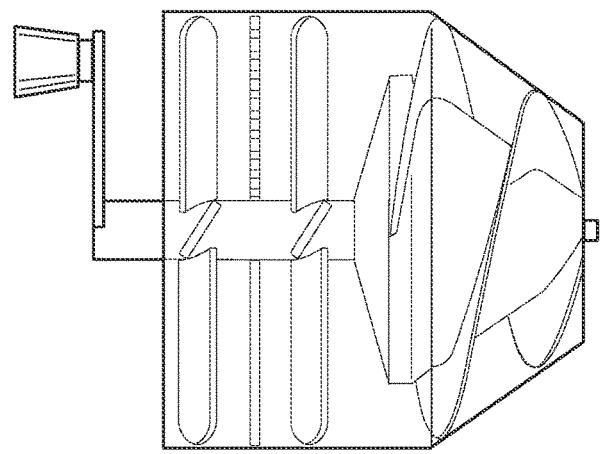
FIGS. 25A and 25B illustrate alternative embodiments of mixing and auger systems to facilitate tissue extraction in accordance with various embodiments of the present disclosure.
Figure 25A:
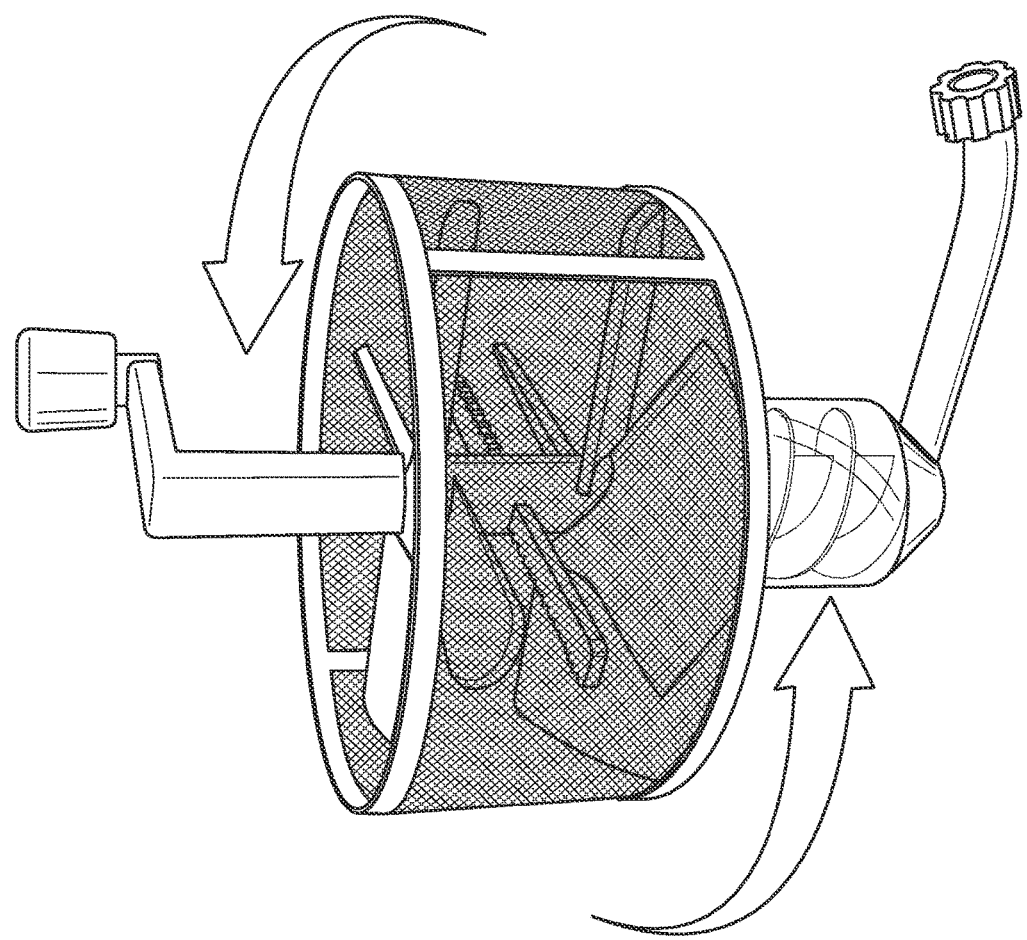

FIGS. 23-25 illustrate tissue treatment systems including mixing and auger systems to facilitate tissue extraction. FIG. 23 illustrates a tissue treatment system with a mixing and auger system to facilitate tissue extraction in accordance with various embodiments of the present disclosure. The mixing and auger system can include a central shaft 2320 that passes into an overmolded clear plastic mesh canister 2350. The central shaft 2320 can include mixing blades 2330, a handle 2314, and an auger 2335. In some embodiments, turning the rotating handle 2314 in one direction (e.g., clockwise) will mix tissue using the mixing blades 2330 while turning the rotating handle 2314 in the opposite direction (e.g., counter-clockwise) will auger the tissue to an extraction port 2360 at the bottom of the tissue treatment device 2300. FIGS. 24A and 24B illustrate perspective and top views of the mixing and auger system of FIG. 23 in a tissue treatment system in accordance with various embodiments of the present disclosure. FIGS. 25A and 25B illustrate alternative embodiments of mixing and auger systems to facilitate tissue extraction in accordance with various embodiments of the present disclosure. In accordance with various embodiments, the auger 2335 can be relatively wide (as illustrated in FIG. 25B) or narrow (as illustrated in FIG. 25A).

Figure 26B:
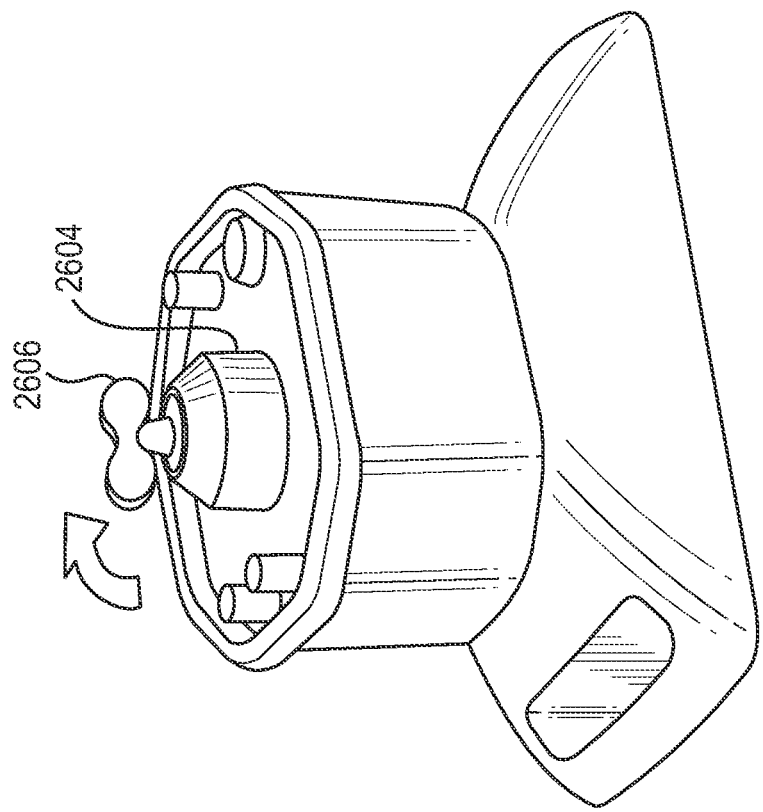
FIGS. 26A and 26B illustrate alternative embodiments of motorized tissue treatment systems in accordance with various embodiments of the present disclosure
Figure 26A:
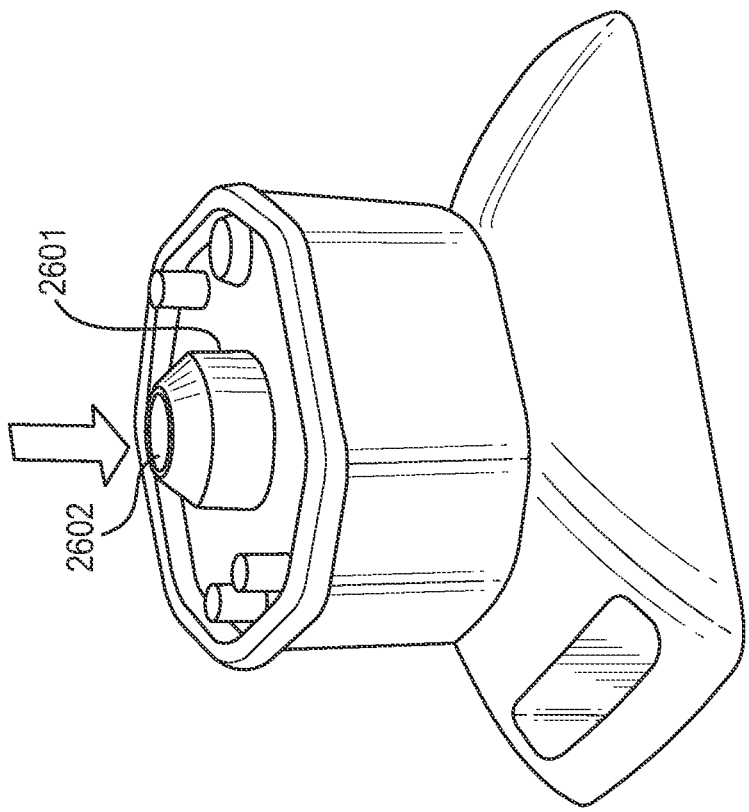

FIGS. 26A and 26B illustrate alternative embodiments of motorized tissue treatment systems in accordance with various embodiments of the present disclosure. In some embodiments, the motorized system can include a battery-powered motor 2601 to automatedly rotate the mixing blades. The motorized system can include a button 2602 to start and stop the motor 2601. In some embodiments, the motorized system can include a spring-loaded wind-up mechanism 2604 and a button. The spring-loaded wind-up mechanism can be wound using a knob 2606. In a preferred embodiment, a user can turn the knob 2606 to wind-up the wind-up mechanism 2604 and press the button to begin agitation. In accordance with various embodiments, the motorized system can rotate a central or mixing shaft at a controlled speed for a controlled duration. The use of controlled speed can ensure that the speed stays within maximum or minimum bounds, which can provide proper agitation without additional stress on the tissue. The ability to mix for a controlled duration can improve usability by allowing a user to attend to other tasks while mixing occurs and by reducing fatigue in the user after extended manual mixing.

Figure 27A:
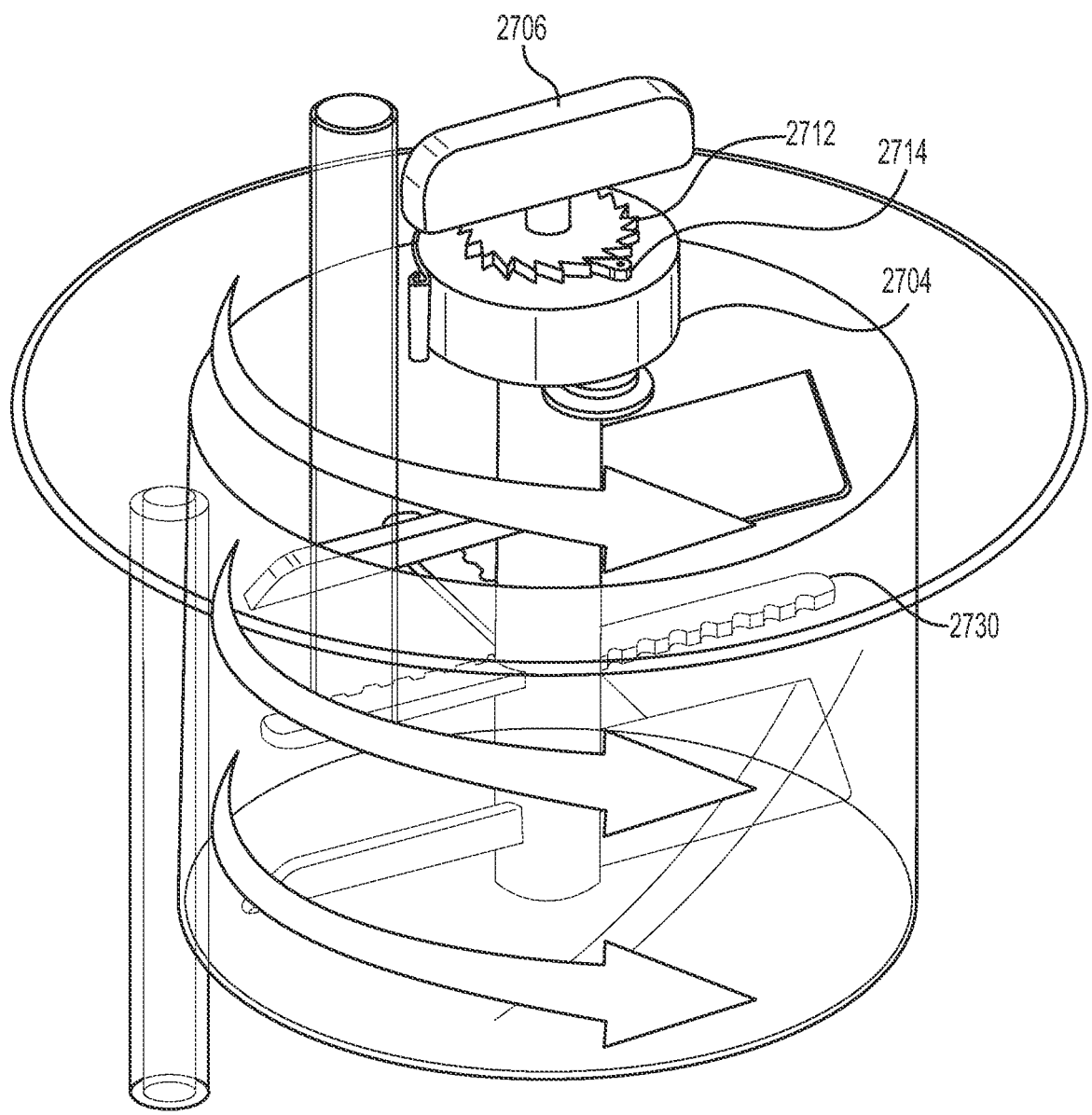
FIG. 27A illustrates a transparent open view of the motorized system to agitate tissue shown in FIG. 26B in accordance with various embodiments of the present disclosure.

FIG. 27A illustrates a transparent open view of the motorized system to agitate tissue shown in FIG. 26B in accordance with various embodiments of the present disclosure. The motorized system can include a knob 2706 and a ratchet mechanism. The ratchet mechanism can include a gear 2712 and a pawl 2714. A spring-loaded wind-up mechanism 2704 can be wound by turning the knob 2706. The pawl 2714 prevents the gear 2712 from unwinding. Activation of the button in some embodiments can release the pawl 2714 so that the gear 2712 can slowly unwind while powering rotation of mixing blades 2730.

Figure 27C:
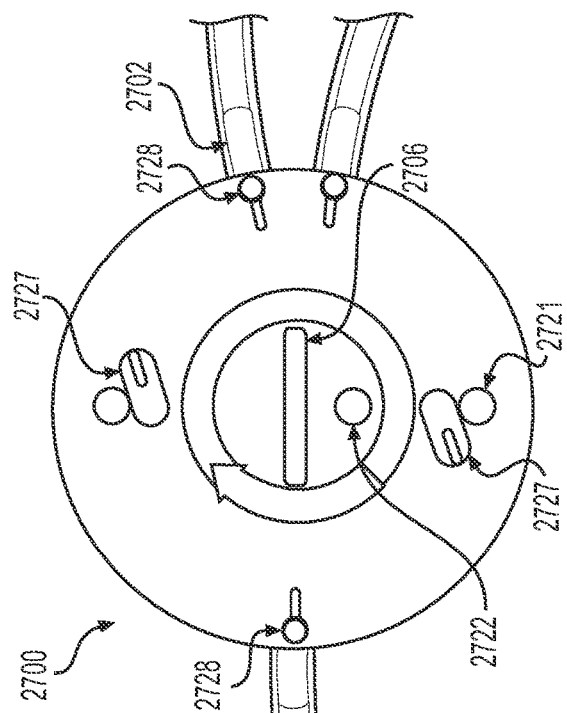
FIG. 27C illustrates a top view of a motorized tissue treatment device in accordance with various embodiments of the present disclosure.
Figure 27B:
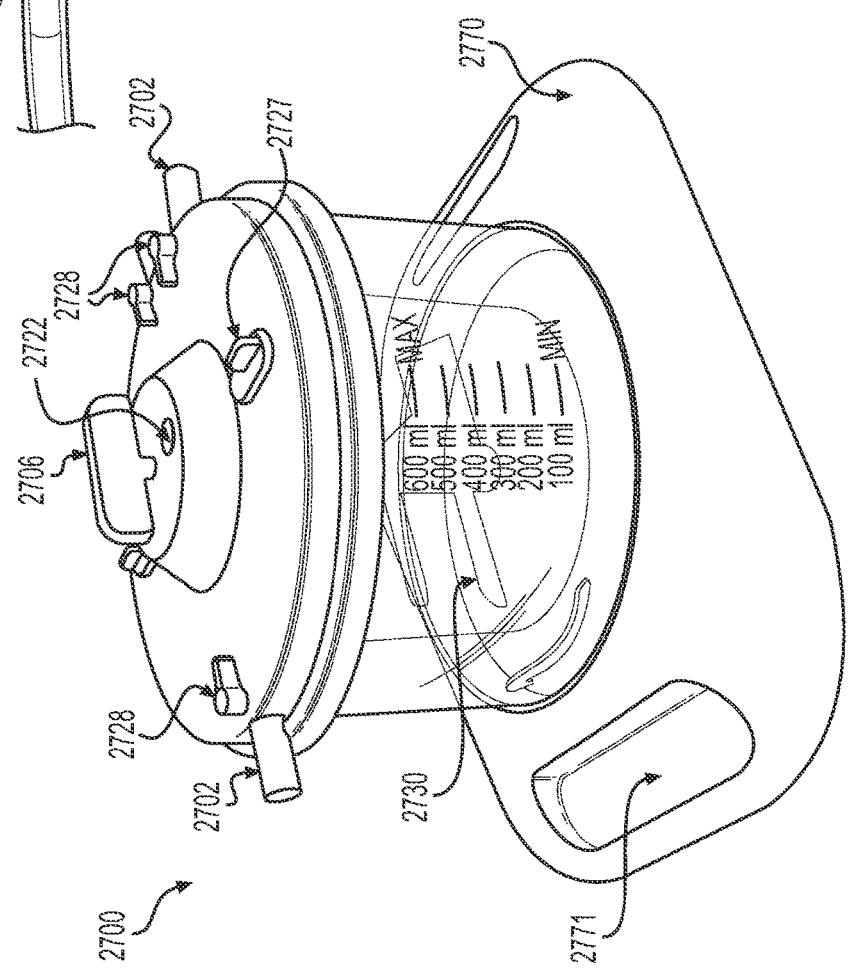
FIG. 27B illustrates a perspective view of a motorized tissue treatment device in accordance with various embodiments of the present disclosure.

FIGS. 27B and 27C illustrate perspective and top views, respectively, of a motorized or powered tissue treatment device 2700 according to various embodiments. In some embodiments, the motorized tissue treatment device 2700 can include a knob 2706 to operate a wind-up mechanism as described above to drive motion of the mixing blades 2730. The button 2722 can be used to release the energy stored in the system after winding up the knob 2706. The tissue treatment device 2700 can include vent ports 2721 to fluidically connect the interior of the device 2700 with the external environment. In some embodiments, the vent ports 2721 can be sealed or unsealed by operation of rotating vent seals 2727. The vent seals 2727 can include a sealing element such as a rubberized surface or O-ring to improve the seal around the vent port 2721 in some embodiments. The tissue treatment system 2700 can also include one or more valves 2728 connected to ports 2702 to control flow into and out of individual ports 2702. Valves 2728 connected individually to ports 2702 provide a simple solution to opening and closing access to the ports 2702 while performing steps in a tissue treatment procedure. Unlike clamping of hoses using loose clamps that can be misplaced or dropped (thus losing sterility), the valves 2728 can be integrated with the device 2700.

The tissue treatment device 2700 can also include a wide base 2770 similar to those described above for other embodiments. The wide base 2770 can include indentations 2771 to facilitate gripping of the device 2700 by the user. In some embodiments, the indentations 2771 can be formed during molding of the wide base 2770. In some embodiments, the indentations 2771 can include overmolded portions. The overmolded portions can include a rubberized material to improve grip of the device by the user.

Figure 28B:
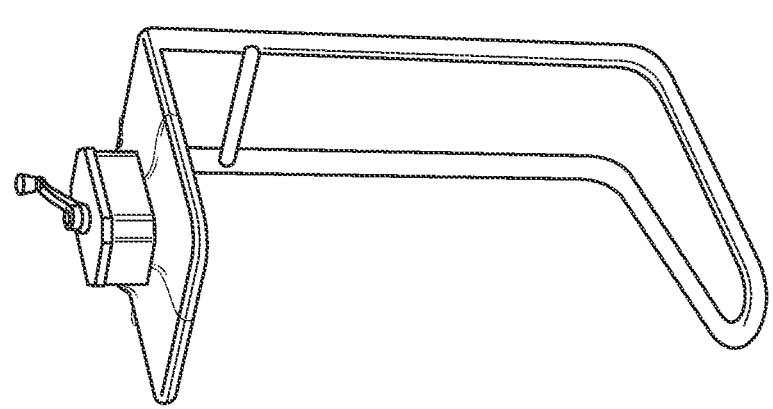
FIGS. 28A and 28B illustrate a tissue treatment system including a sterile drape in accordance with various embodiments of the present disclosure.
Figure 28A:
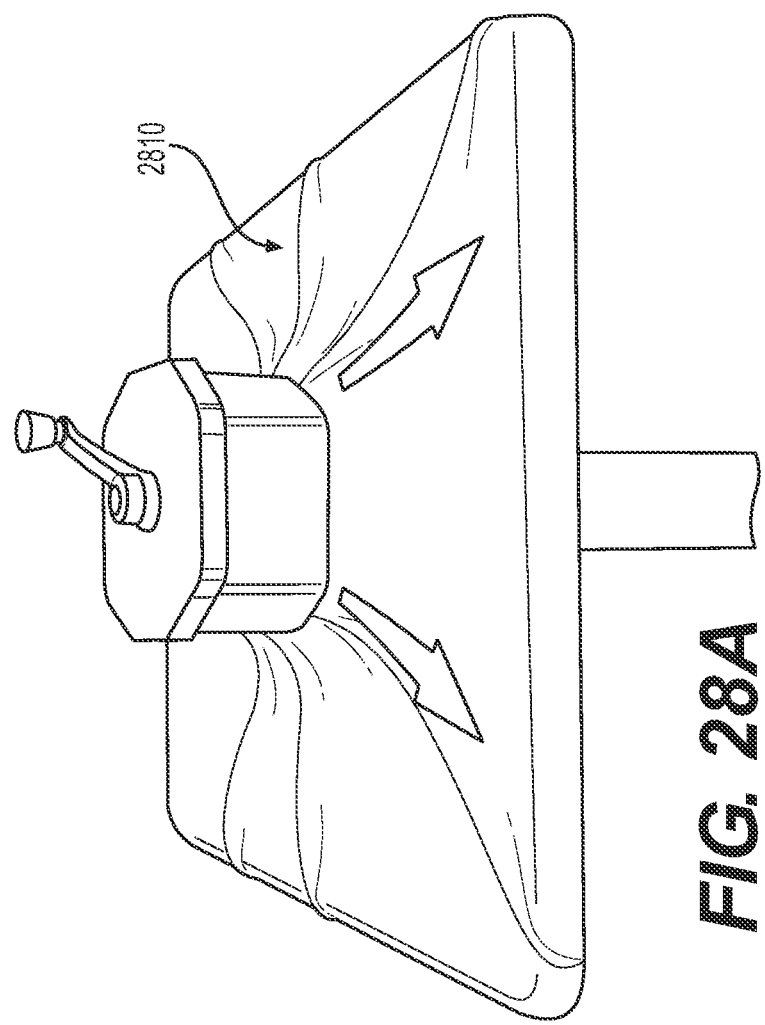
Figure 29A:
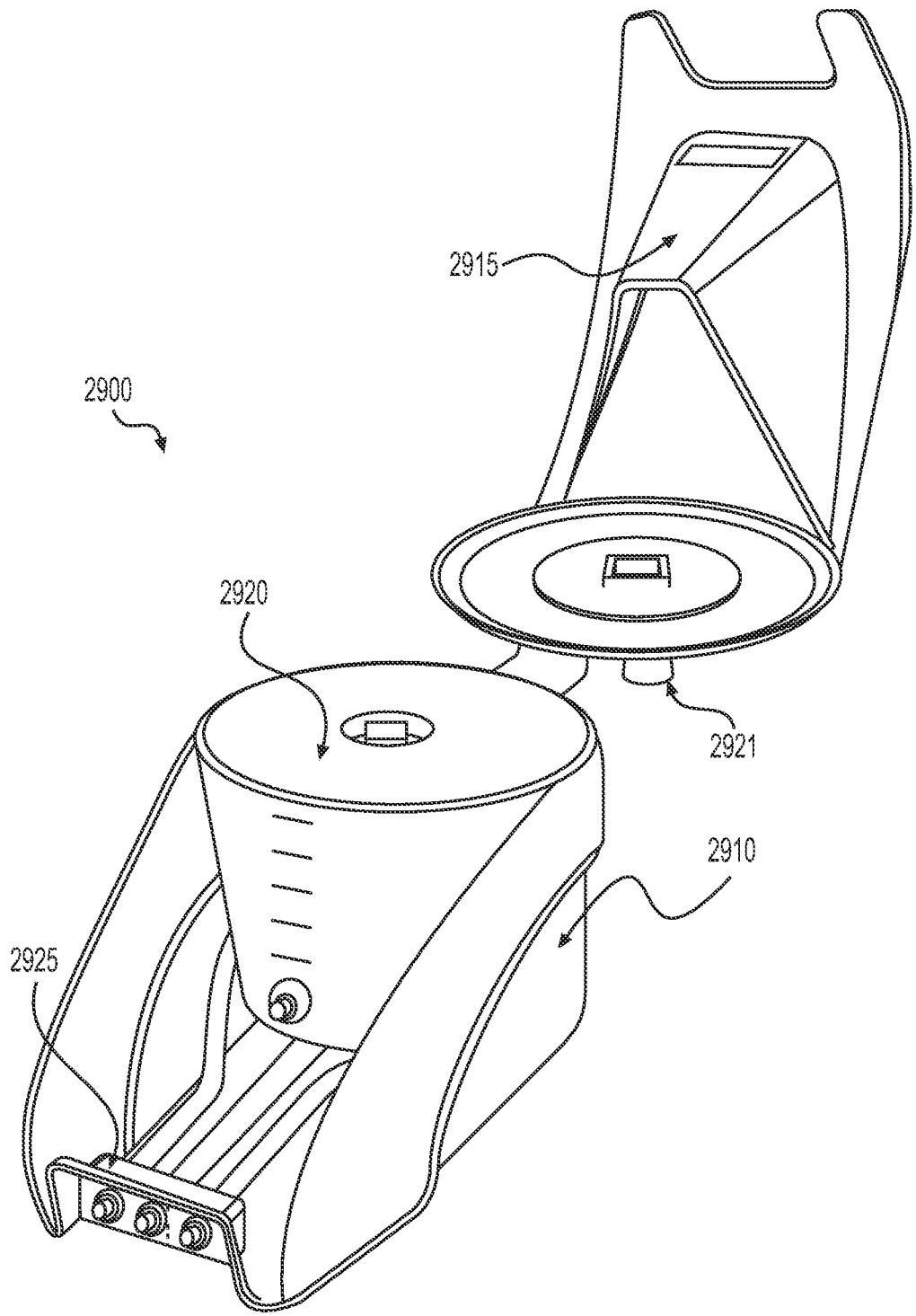
FIGS. 29A-29D illustrate a tissue treatment system including a base and a replaceable tissue processing unit in accordance with various embodiments of the present disclosure.
Figure 29C:
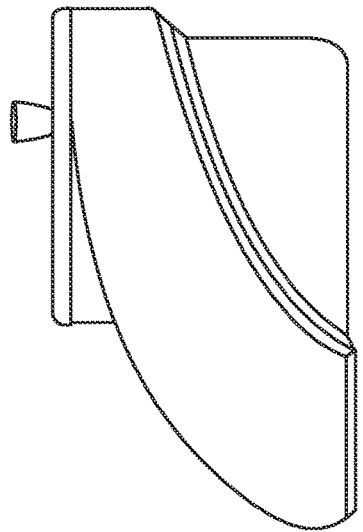
Figure 29D:
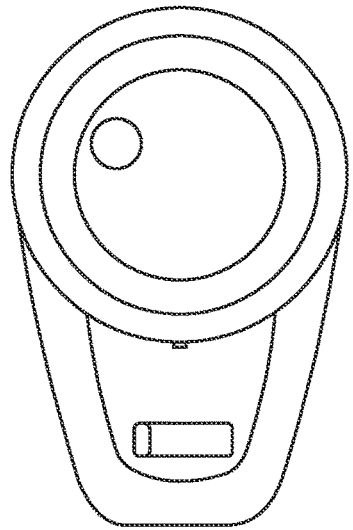
Figure 29B:
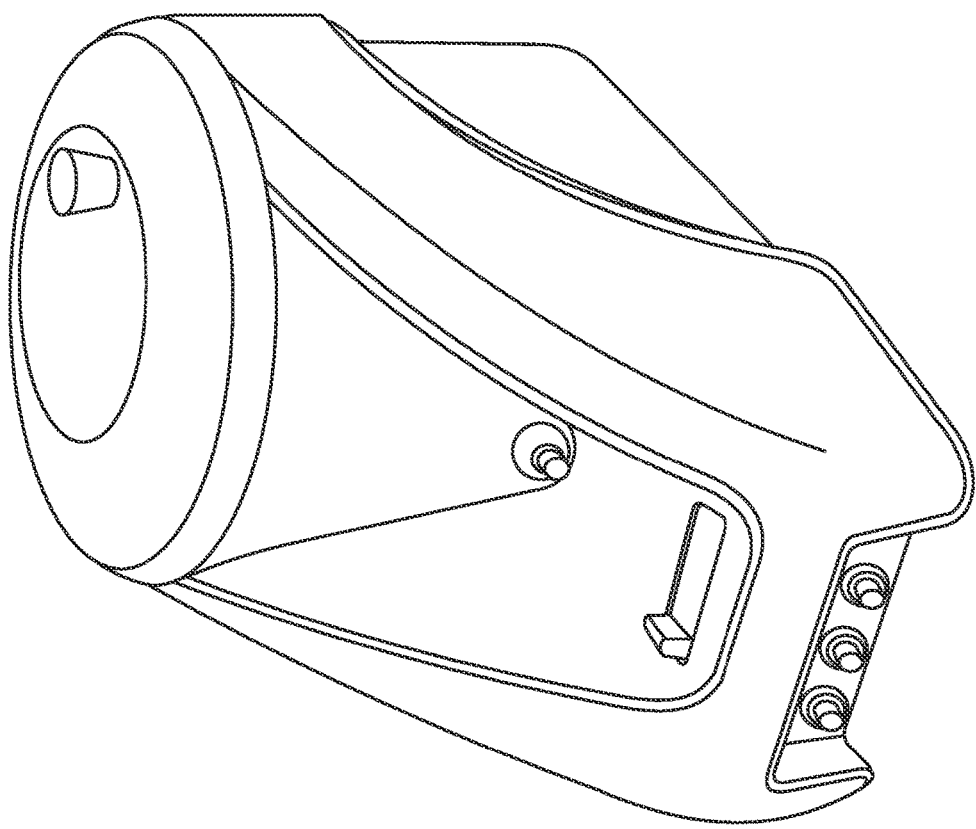

FIGS. 28A and 28B illustrate a tissue treatment system including a sterile drape in accordance with various embodiments of the present disclosure. In some embodiments, the sterile drape 2810 can come pre-attached to the canister or container of the tissue treatment system 2800. The sterile drape 2810 can be stretched over a working surface and adhered to the underside of the surface. In some embodiments, the sterile drape 2810 can include an adhesive. In some embodiments, the sterile drape 2810 can be sized to fit over a Mayo stand or other tray commonly found in surgical environments. Because various surgical procedures may have already occurred before use of a tissue treatment system occurs, a sterile drape 2810 attached directly to the tissue treatment system 2800 can quickly provide a practitioner with a sterile surface for tools by simply extending over and covering surfaces that may have been contaminated during earlier procedures.

FIGS. 29A-D illustrate a tissue treatment system 2900 including a base and a replaceable tissue processing unit in accordance with various embodiments of the present disclosure. The top cover 2915 of the base unit 2910 can lift to allow for insertion of the tissue processing unit including a container or canister 2920 and tube manifold assembly 2925. The top cover 2915 can be lowered for operation. In some embodiments, a rotating handle mechanism 2921 can be integrated into the base unit 2910 while the mixing blades can be integrated into the canister 2920. The use of a two-component system (base unit 2910 and canister 2920/tube manifold assembly 2925) can reduce per-unit costs for some portions of the system 2900. In some embodiments, the base unit 2910 can be reused for multiple procedures while the canister 2920 and tube manifold assembly 2925 can be single use and/or disposable. In some embodiments, the base unit 2910 can be sterilizable. In some embodiments, the base unit 2910 can be secured to a surface, e.g., table, during use to stabilize the base unit 2910. By securing the base unit 2910, the system 2900 is less likely to tip during mixing, agitation, or stirring of the contents of the system 2900.

Figure 30B:
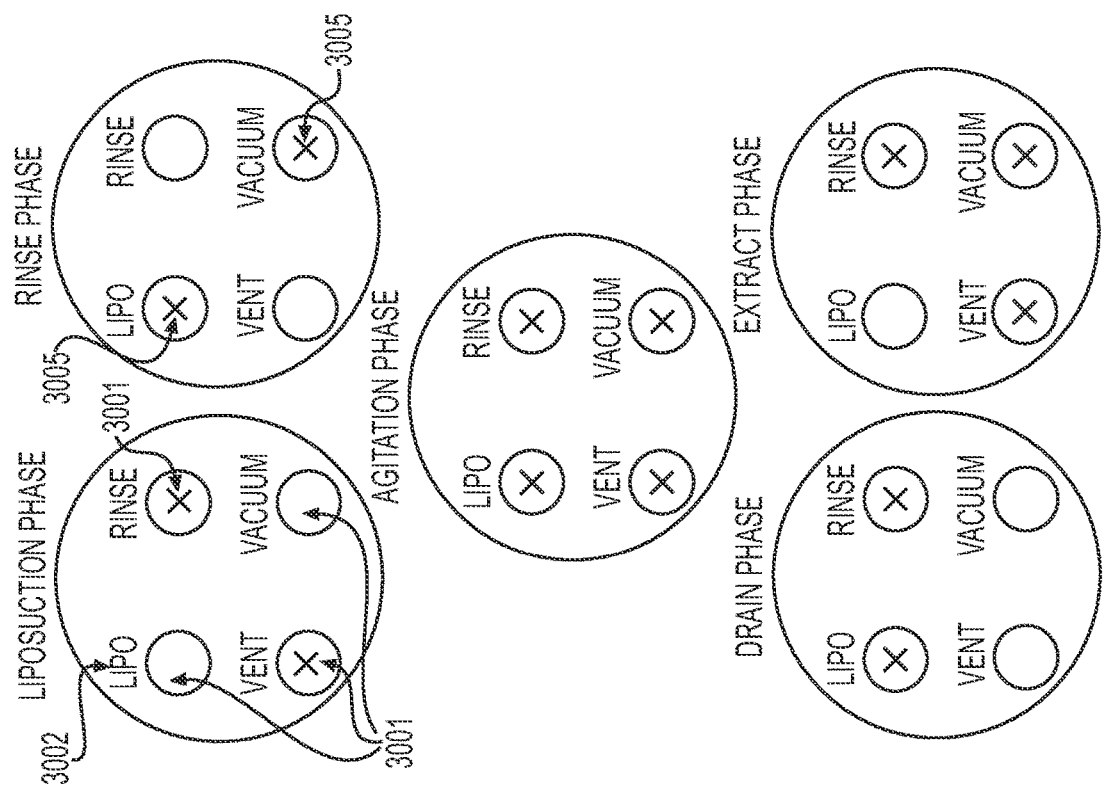
FIGS. 30A and 30B illustrate a tissue treatment system including a tube management device during various phases of operation in accordance with various embodiments of the present disclosure.
Figure 30A:
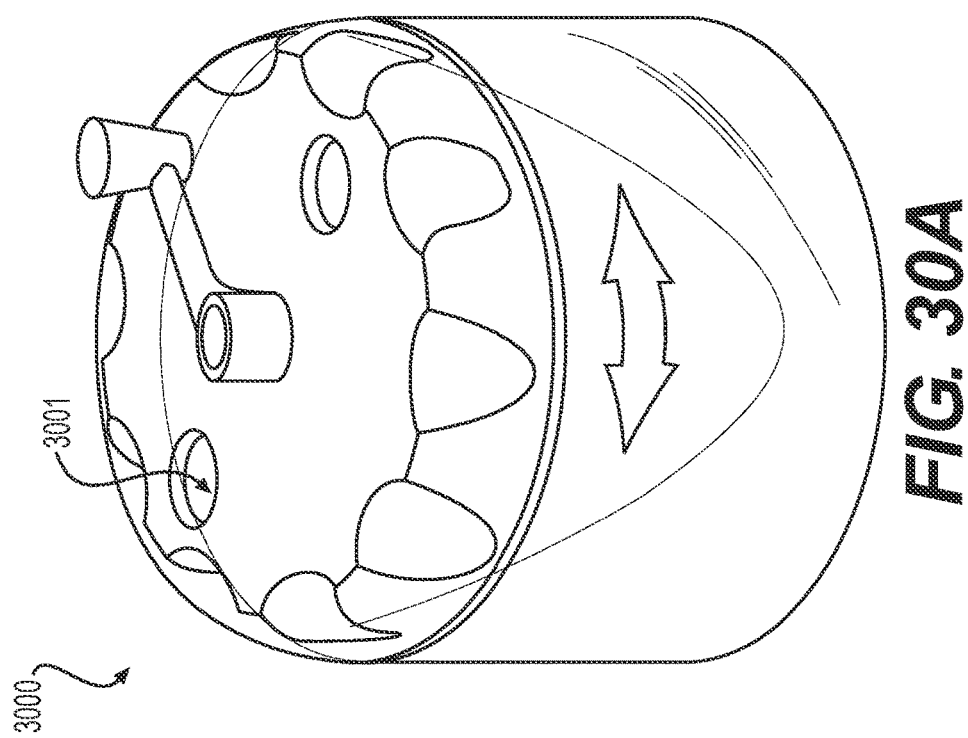

FIGS. 30A and 30B illustrate a tissue treatment system 3000 including a tube management device according to various embodiments of the present disclosure. In an exemplary embodiment, the system 3000 can use a tube-switching mechanism such as the flow management device 1000 described above with reference to FIG. 10A. The lid of the system 3000 can include holes 3001 to allow a portion of a plate (e.g., the first plate) to be seen through the holes 3001. In some embodiments, each hole 3001 can be associated with a port and can include an annotation 3002 that identifies the function of the port. Example annotations 3002 can include "Lipo," "Rinse," "Vent," and "Vacuum."

In some embodiments, the uppermost plate of a tube management system can be imprinted with writing or labels 3005 that indicate the current status of the tubing connections. For example, the plate can include "X"s that align with the holes 3001 when the plates within the tube management system are aligned correctly for a particular step in a tissue processing operation. Several exemplary arrangements of the labels 3005 as seen through the holes 3001 are shown in FIG. 30B. As an example, labels 3005 can appear in the holes 3001 corresponding to the vent and rinse ports during the drain phase to indicate that these ports are closed while the remaining ports (i.e., lipo and vacuum) are open and do not have labels 3005 appearing in corresponding holes 3001. Labels can be positioned on the plate to appear in holes as required to convey the open and closed status of ports for a variety of phases of the tissue processing operation, e.g., the liposuction, rinse, agitation, drain, and extraction phases. As described herein, the presence of a label 3005 indicates that a port is closed while those holes 3001 that do not have a label 3005 indicate ports that are open. However, one of ordinary skill in the art will appreciate that the labeled holes 3001 could indicate corresponding open ports while unlabeled holes 3001 could indicate closed ports.

FIGS. 31A-31D illustrate views of an alternative embodiment of a tube management device to that of FIGS. 30A-30B. In the depicted tube management device 3110, an indicator switch 3103 can point to an annotation 3113 that describes the current phase of the tissue processing procedure. That is, the indicator switch 3103 may not provide the user with direct information as to the open/closed status of any given port but can provide the user instead with information regarding the current step of the tissue processing procedure. In this way, the indicator switch 3103 can guide the user through the steps of action and open/close the corresponding connections for each step as described in greater detail below. Exemplary annotations 3113 can include "Harvest," "Wash," "Filter," and "Extract" in some embodiments. The use of an indicator switch 3103 as described herein above can eliminate the need for disconnections and connections of tubes to the ports 3102 as the tubes can be left connected throughout the procedure.

In some embodiments, the indicator switch 3103 can be configured to allow control of the second plate or third plate of a tube management device as described above with reference to FIGS. 9A-10B. In other embodiments, the tube management device 3110 can include an outer lid 3105 and an inner lid 3111 as described below.

Figure 32:
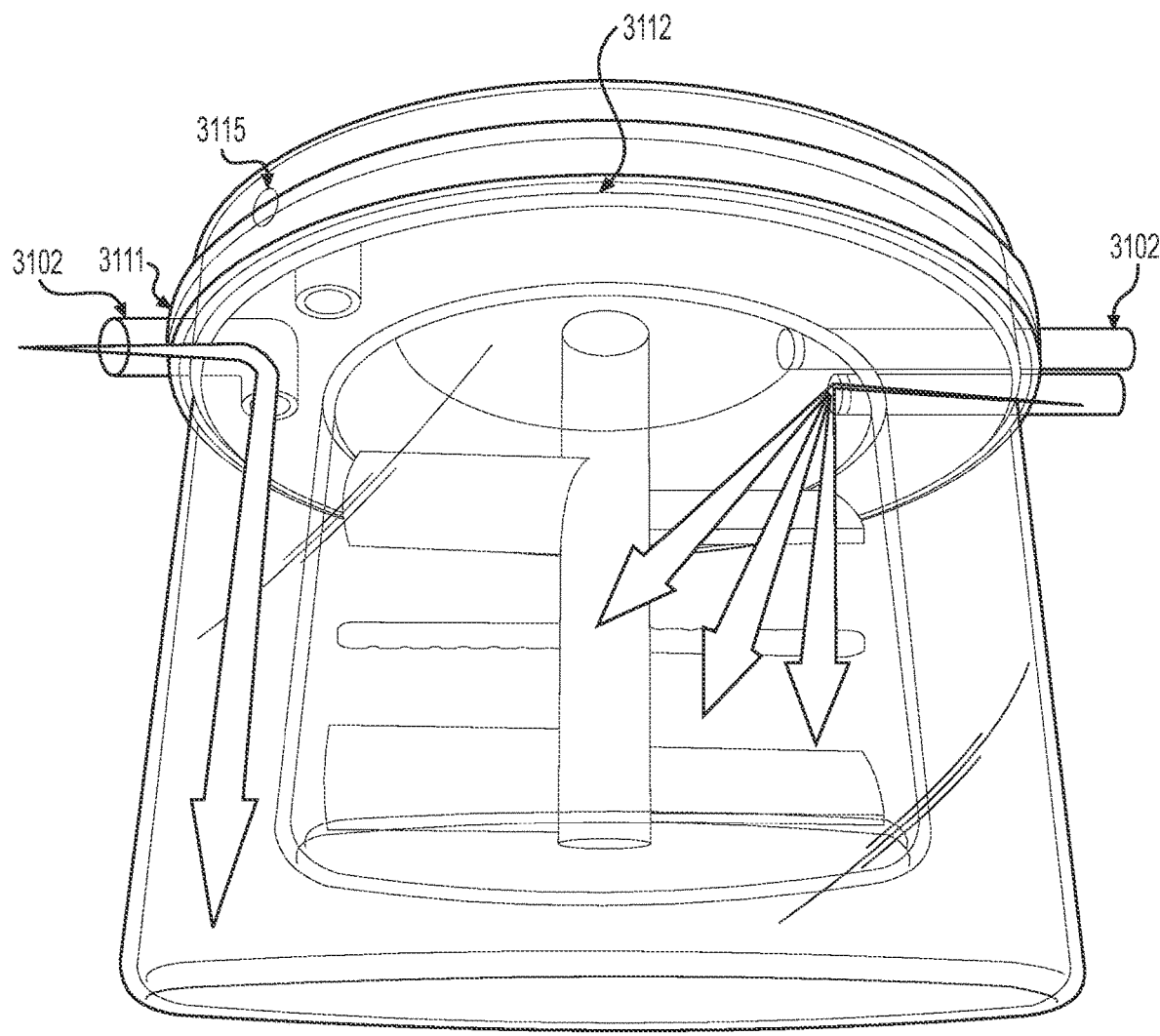
FIG. 32 illustrates an inferior perspective view of the tissue treatment system of FIG. 31A.
Figure 33A:
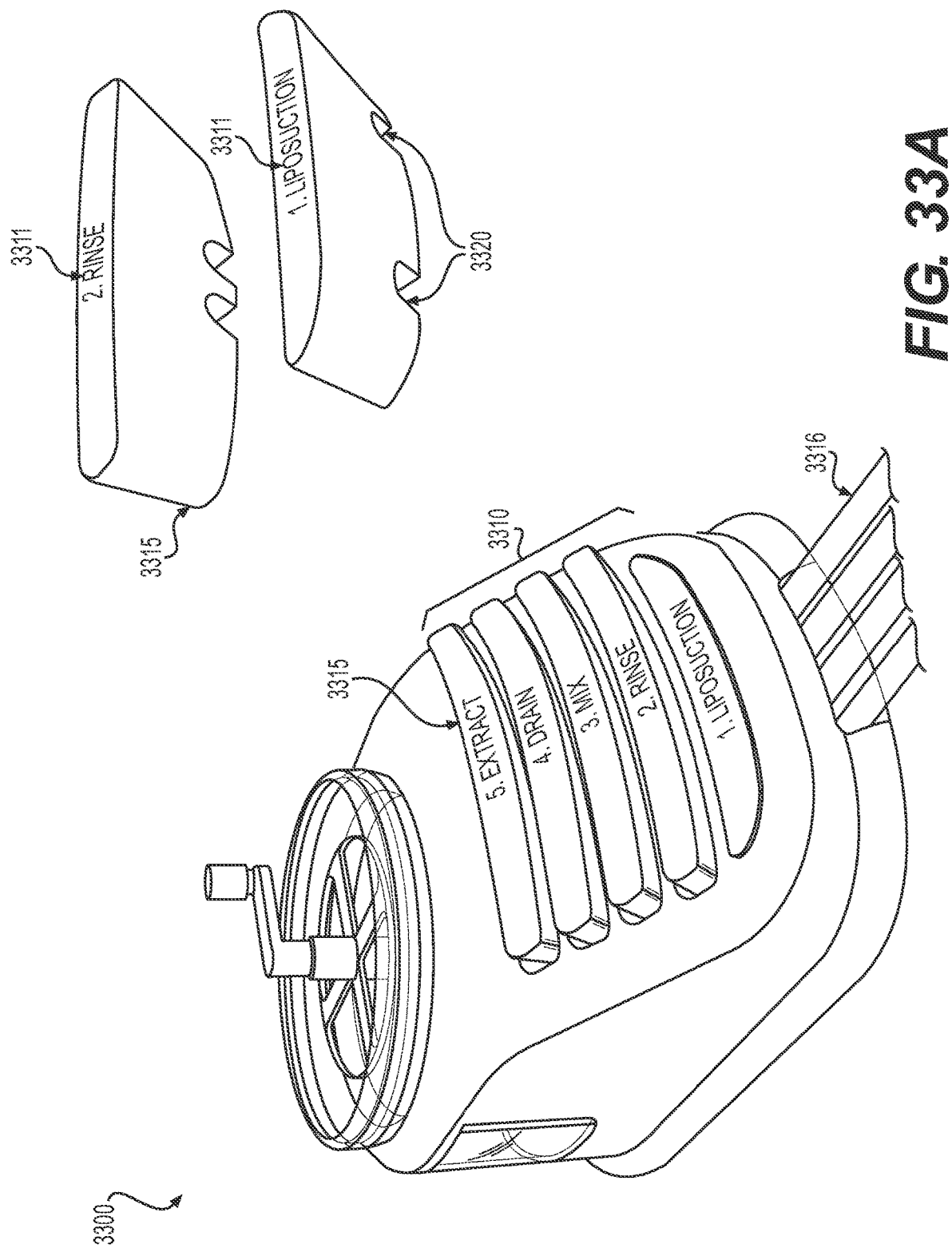

FIG. 32 illustrates a view from below of the tissue treatment system of FIG. 32A. As shown, the tube management device 3110 can include an outer lid 3111 and an inner lid 3112 seated within and rotatable relative to the outer lid 3111. In some embodiments, the inner lid can include a plurality of holes 3115 at various locations around the periphery of the inner lid 3112. Similarly, the outer lid 3111 can include a plurality of ports 3102 that are engageable with tubes to deliver tissue, fluids/solutions, or vacuum pressure to the system 3100. As the indicator switch 3103 is rotated, the inner lid 3112 can rotate with respect to the outer lid 3111 to bring a subset of the holes 3115 into fluid communication with one or more of the ports 3102. For example, when the indicator switch 3103 is pointing to the annotation for "Wash," the holes 3115 and ports 3102 align for the tubes for venting and carrying solution into the device can be connected while other holes are not connected. As shown in FIG. 32, some holes 3115 are fluidically connected to the interior of the container and internal to the filtering structure while other holes 3115 are fluidically connected to the interior of the container external to the filtering structure.

In some embodiments, sealing elements can be overmolded onto surfaces of the inner lid 3112 or outer lid 3111 to prevent leaking into the space between them. In some embodiments, each hole 3115 can be surrounded by a collar. In such an embodiment, the outer lid 3111 can be formed of a softer plastic material that will flex as the protruding collar of the inner lid 3112 rotates against it. This flexing can create a seal around the hole 3115. When the inner lid 3112 is rotated such that a hole 3115 aligns with a port 3102, the collar can "snap" into position as it aligns with the port 3102. In some embodiments, each hole 3115 can have an insert formed of a sealing material such as rubber to form a seal between inner lid 3112 and outer lid 3111 to prevent fluids or gases from escaping from the hole 3115.

FIGS. 33A-33D illustrate views of a tissue treatment system 3300 including a tube management device 3310 in accordance with various embodiments of the present disclosure. The tube management device 3310 can include a plurality of tube restriction devices in the form of press-down buttons 3315 that block or unblock the correct tubing lines 3316 when pressed. In some embodiments, each press-down button 3315 can include an annotation 3311 that corresponds to a step in the tissue processing procedure. Example annotations 3311 include "liposuction," "rinse," "mix," "drain," or "extract." In some embodiments, the annotations 3311 can include a numeral that indicates the placement of the corresponding step in the sequential order of steps that form the procedure.

In some embodiments, when a press-down button 3315 is pressed down and locked, the appropriate tubes 3316 are pinched off while other tubing paths are left open. For example and as shown in the isolated view of the press-down buttons 3315 in FIG. 33A, each press-down button 3315 can include one or more cutouts 3320 shaped to allow tubes that pass therethrough to remain unblocked when the button is pressed. In the example shown, four tubes 3316 can pass below the button 3315 labeled "2. Rinse" and the button labeled "1. Liposuction". When the button 3315 labeled "2. Rinse" is pressed, the two innermost tubes are not blocked while the two outermost tubes 3316 are blocked. When the button 3315 labeled "1. Liposuction" is pressed, the two innermost tubes 3316 are blocked while the two outermost tubes 3316 are not blocked.

Figure 34:
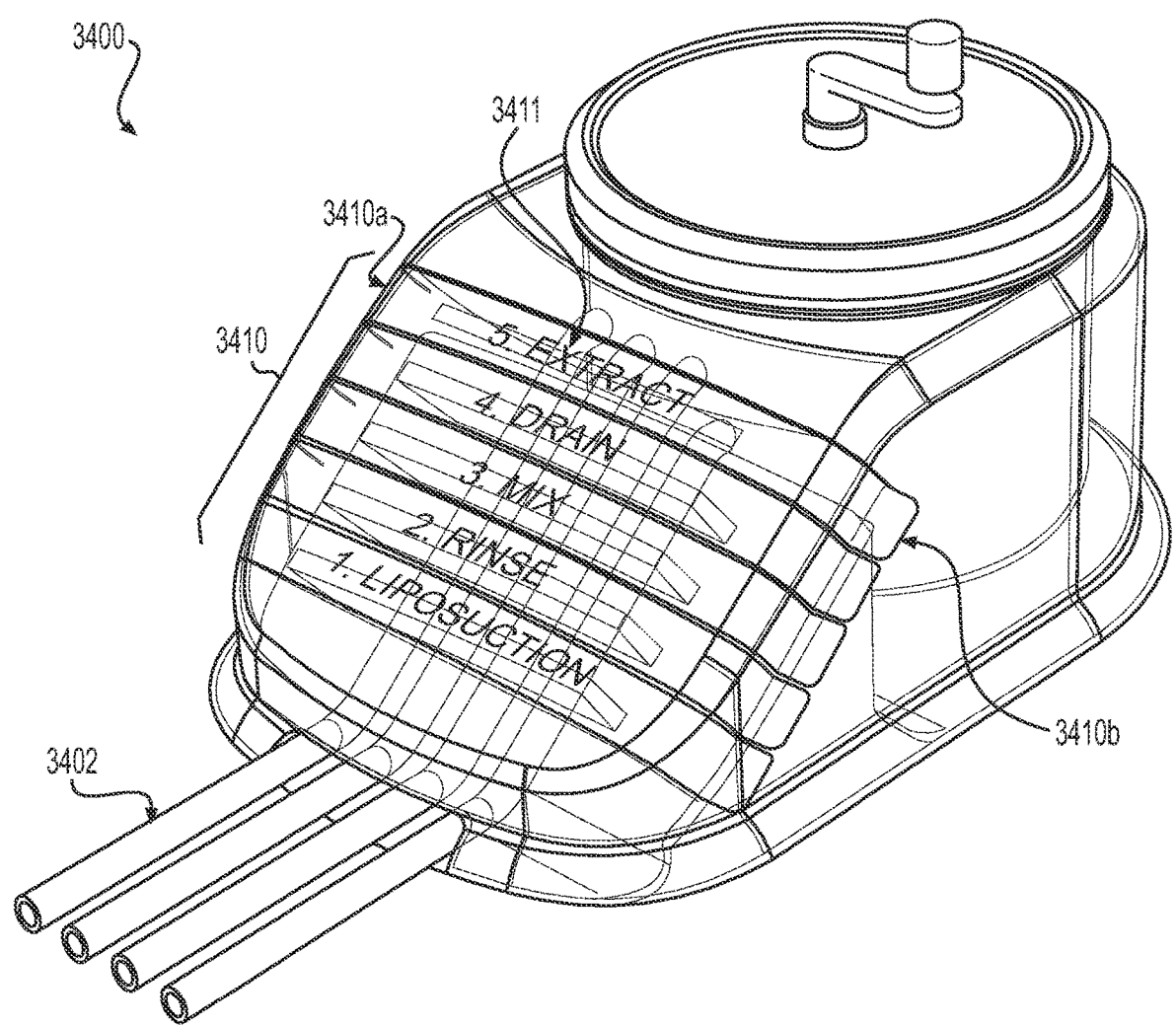
FIG. 34 illustrates a tissue treatment system including a tube management device in accordance with various embodiments of the present disclosure.

FIG. 34 illustrates a tissue treatment system 3400 including an alternative tube management device including a plurality of tube restriction devices in the form of snap-down panels 3410. The snap-down panels 3410 can clamp the appropriate tubes 3402 for each step in a tissue processing sequence in a manner similar to a pinch valve. For example, the underside of each snap-down panel 3410 can include a series of cutouts in similar fashion to the cutouts described above with reference to the press-down buttons 3315 of FIGS. 33A-33D. In some embodiments, each snap-down panel 3410 can include a hinged end 3410a and a grip end 3410b. The user can grasp the grip end 3410b to apply downward force to the snap-down panel 3410 to lock it into place. As such, the grip end 3410b can include a latch that engages with the body of the system 3400 to hold the panel in a locked-down position. In accordance with various embodiments, each snap-down panel 3410 can include an annotation 3411 that corresponds to a step in a tissue processing sequence. The user can thus be directed to perform steps in sequence by ordering activation of the snap-down panels in a progression from first step to last.

Figure 35:
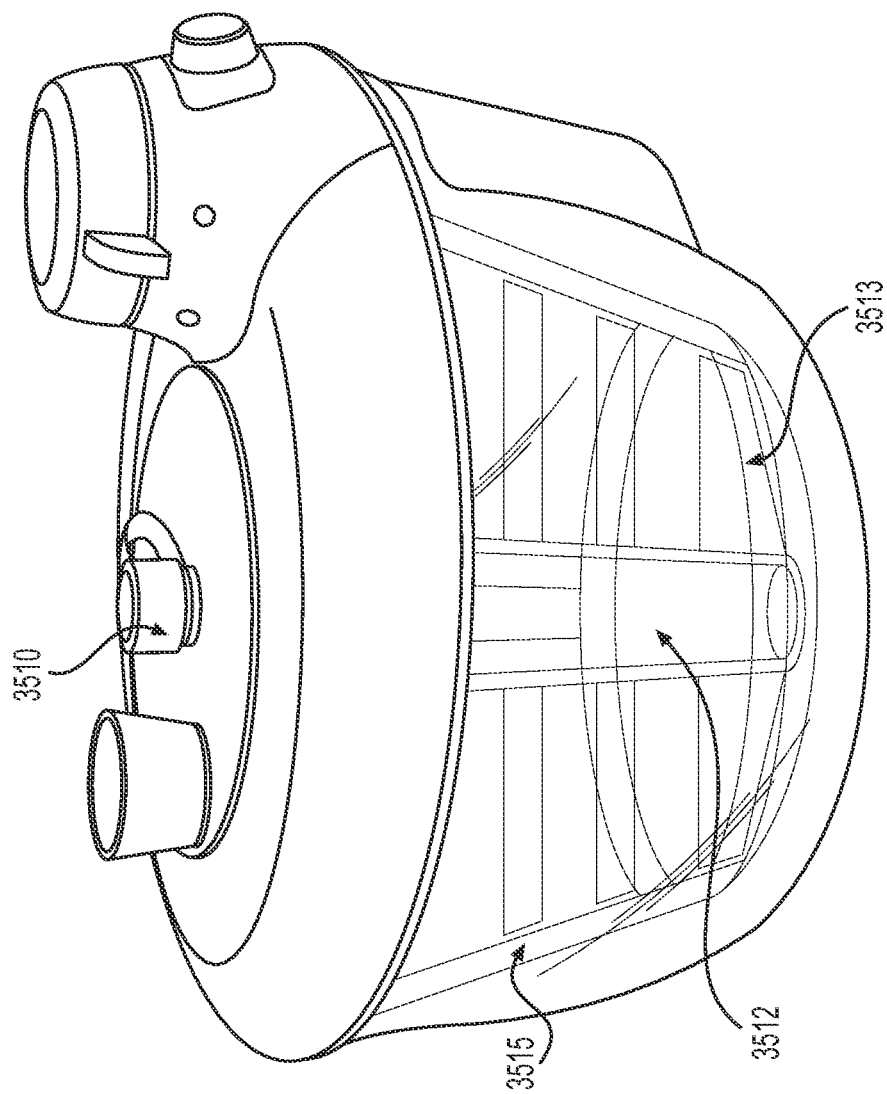
FIG. 35 illustrates a tissue treatment system including a hollow central shaft to extract adipose tissue in accordance with various embodiments of the present disclosure.
Figure 36:
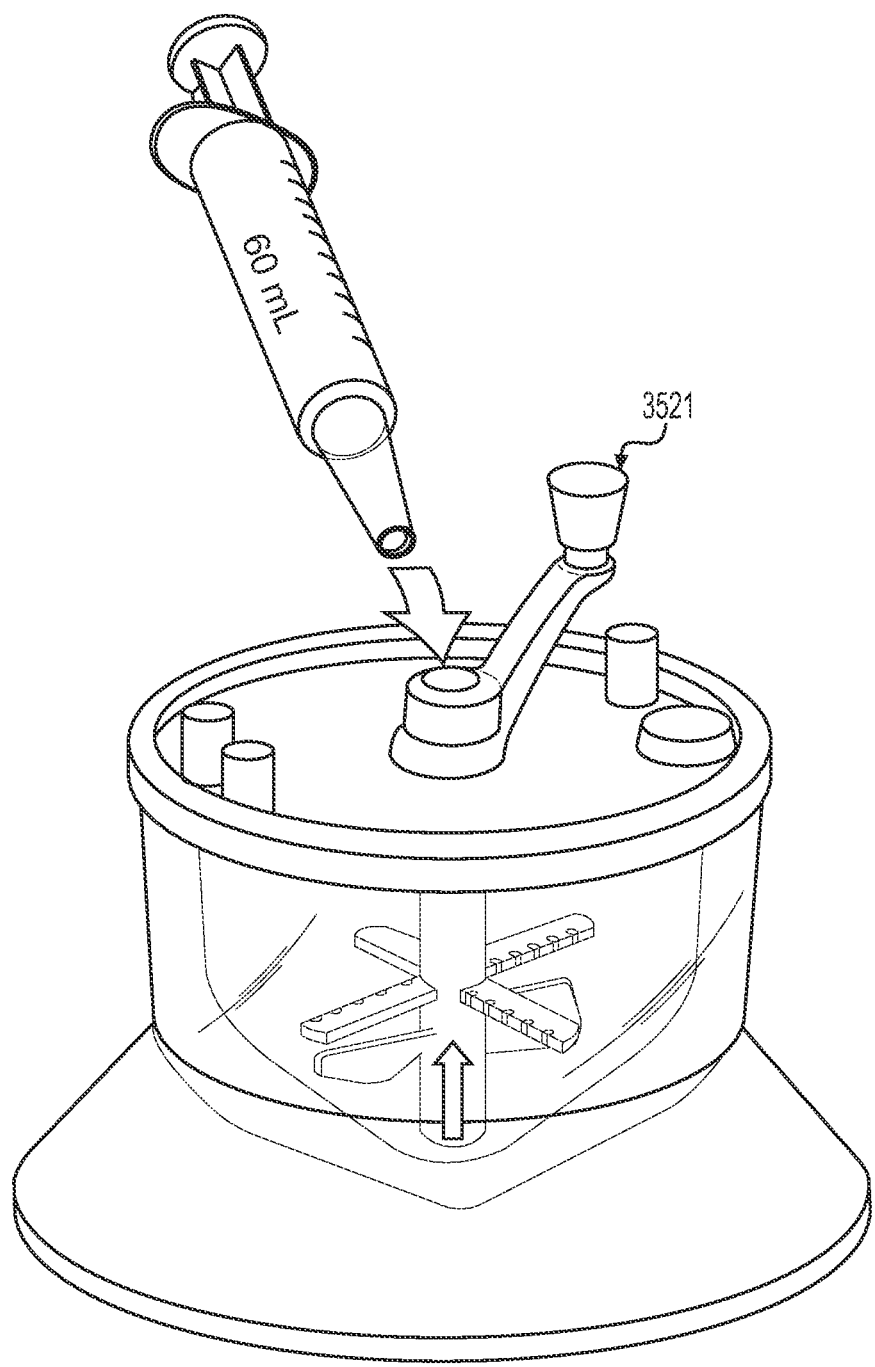
FIG. 36 illustrates an alternative embodiment of a tissue treatment system including a hollow central shaft in accordance with various embodiments of the present disclosure.

FIG. 35 illustrates a tissue treatment system 3600 with an outlet 3610 to extract adipose tissue in accordance with various embodiments of the present disclosure. The outlet 3510 can pass through the center of a shaft 3512 where the mixing blades 3513 are mounted. In some embodiments, placing the outlet 3510 in fluid communication with the bottom of the filtering structure 3515 via the shaft 3512 allows efficient withdrawal of tissue without the need to tip the system 3600 to one side or the other. In some embodiments, the outlet 3610 can pass through a portion of the rotary handle 3521 as shown in FIG. 36. In some embodiments, the outlet 3610 can be shaped and sized to mate with a syringe.

Figure 37A:
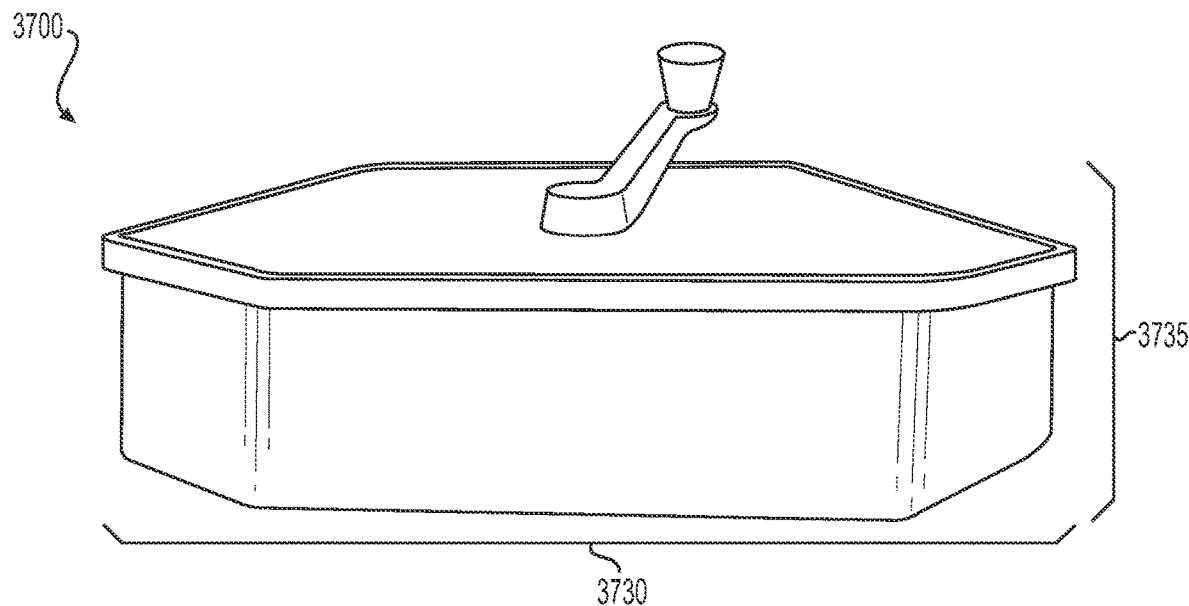
FIG. 37A illustrates a low profile tissue treatment system in accordance with various embodiments of the present disclosure.
Figure 37B:
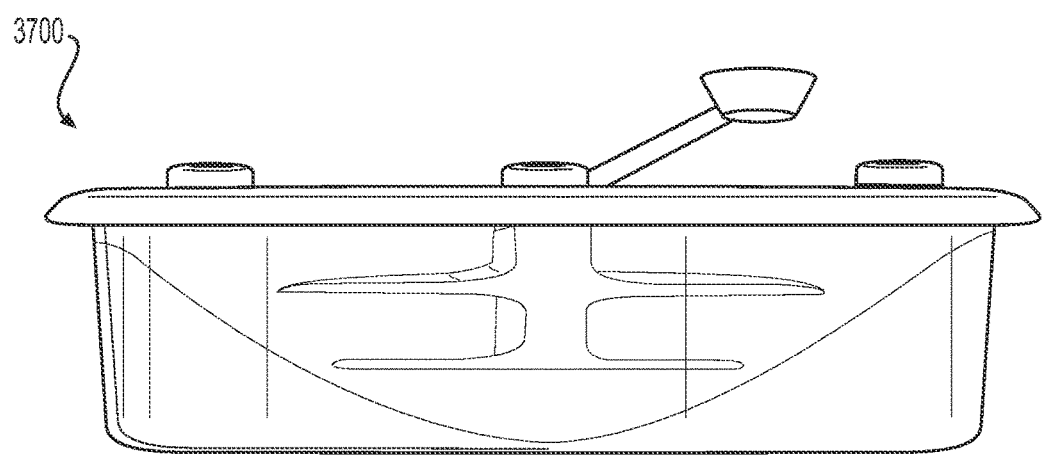
FIG. 37B is a side view of the system of FIG. 37A.

FIGS. 37A and 37B illustrate views of a tissue treatment system 3700 with a low profile in accordance with various embodiments of the present disclosure. In some embodiments, a width 3730 of the system 3700 can be greater than a height 3735 of the system 3700. For example, the width 3730 can be greater than at least two times, three times, four times, or a higher multiple of the height 3735 of the system 3700. The low profile created by having a greater width 3730 than height 3735 can improve stability and prevent translation or tipping of the system during mixing and extraction operations by lowering the center of gravity of the system 3700 in some embodiments.

Figure 38:
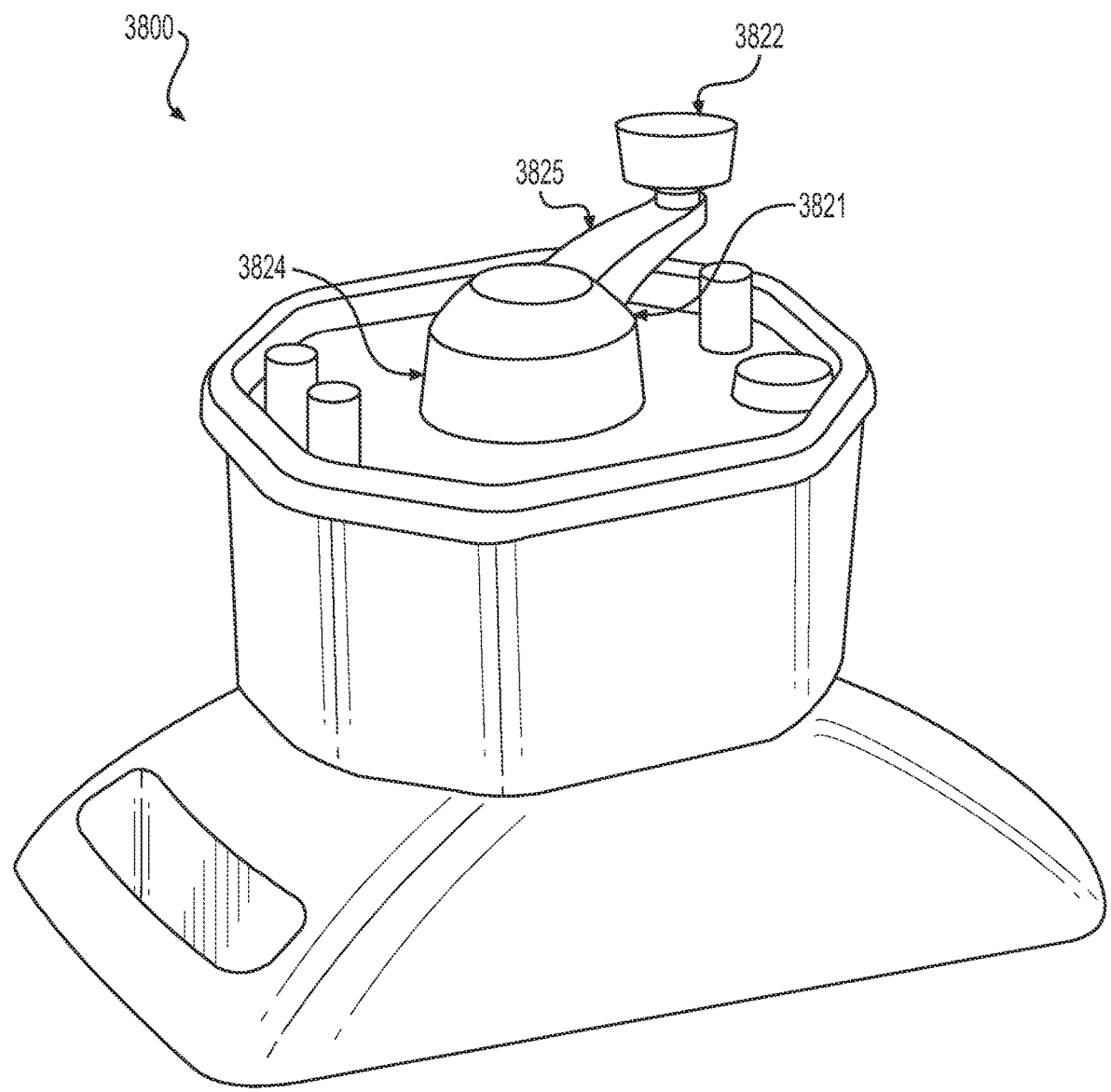
FIG. 38 illustrates a tissue treatment system in accordance with various embodiments of the present disclosure.

FIG. 38 illustrates a tissue treatment system 3800 with an ergonomic rotary handle 3821 in accordance with various embodiments. The grip portion 3822 of the rotary handle 3821 can be formed in a variety of shapes and sizes to fit the hand of a user. For example, the grip portion 3822 can have a flattened geometry (e.g., ellipsoidal rather than circular) to provide a more comfortable grip. In an exemplary embodiment, the grip portion 3822 can freely rotate atop a cross piece 3825. A rotating grip portion 3822 can allow the user to grasp the grip portion 3822 and maintain the same grasping posture without needing to readjust throughout a complete rotation of the rotary handle 3821. In some embodiments, the rotary handle 3821 can include a raised platform 3824 where the base of the rotary handle 3821 meets the system 3800. The raised platform 3824 can provide additional clearance between the rotary handle 3821 and the top of the system 3800 to prevent the user from hitting part of the hand (e.g., knuckles) on the system 3800 while operating the handle 3821.

FIGS. 39A and 39B illustrate a tissue treatment system 3900 including a support handle 3930. In accordance with various embodiments, the user can grip the support handle 3930 to transport the system 3900 or immobilize the system 3900 during a tissue processing operation. In some embodiments, a base end 3930a of the support handle 3930 can be at a same level as the base of the system 3900 as shown in FIG. 39B. In other words, the base end 3930a and the base of the system 3900 can both make contact with a flat surface when the system 3900 is placed on the surface. As a result, the base end 3930a of the support handle 3930 can provide an additional point of contact between the system and the surface upon which it rests. The additional point of contact increases stability of the system and can prevent tipping similar to the function of an outrigger on a sailing vessel. In some embodiments, the support handle 3930 is formed by molding.

Figure 40:
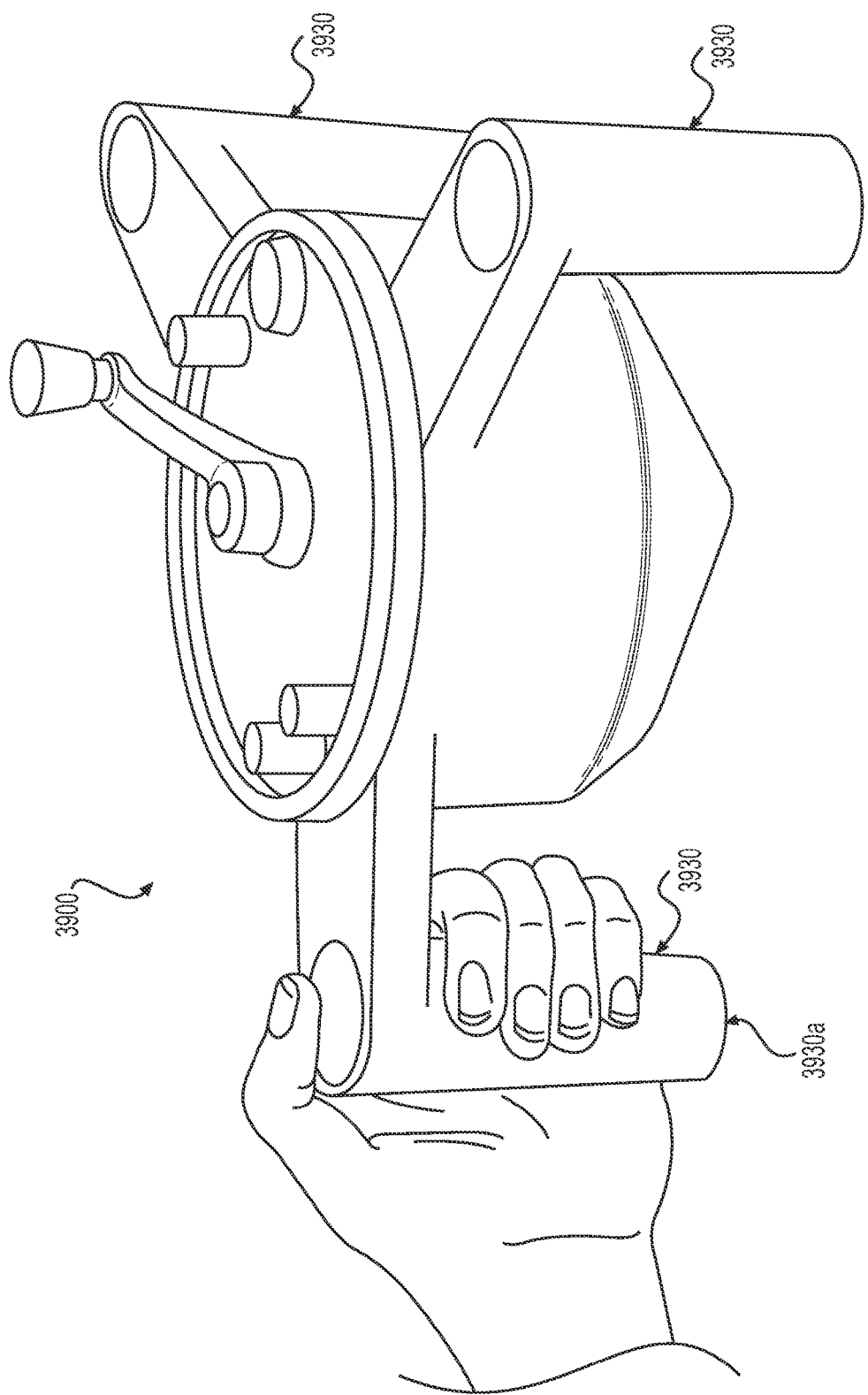
FIG. 40 illustrates a tissue treatment system including multiple molded handles in accordance with various embodiments of the present disclosure.

FIG. 40 illustrates the tissue treatment system 3900 with a plurality of support handles 3930. The plurality of support handles 3930 can act like a tripod to provide increased stability in some embodiments. The use of a plurality of support handles may also provide a variety of hand grip positions and/or allow multiple persons located on opposite sides of the system 3900 to perform steps in the tissue processing procedure without needing to rotate the entire system to face each person in turn.

FIGS. 41A-41C illustrate a tissue treatment system 4100 and associated packaging 4160 in accordance with various embodiments of the present disclosure. In accordance with various embodiments, the tissue treatment system 4100 can be placed into the packaging 4160 to stabilize the system. In some embodiments, the packaging 4160 can be vacuum formed to snugly fit a container of the system 4100 within. The packaging 4160 can provide cushioning and protect the system 4100 during shipping or delivery of the product. Upon receipt by the customer, the packaging 4160 and system 4100 can be removed from the shipping container and assembled together. For example, the system 4100 can be shipped within the packaging 4160. To remove the system 4100 from the packaging 4160 in some embodiments, a seal cover 4161 can be peeled back to reveal the system 4100. In some embodiments, the system 4100 can be removed from the packaging 4160, inverted, and placed back into the packaging 4160. The packaging 4160 can have a wide base to prevent tipping and stabilize the system 4100 during use. In some embodiments, the packaging 4160 can include molded grooves 4134. The molded grooves 4134 can help to manage the tubing by routing the tubing down towards the base of the packaging 4160.

Figure 42B:
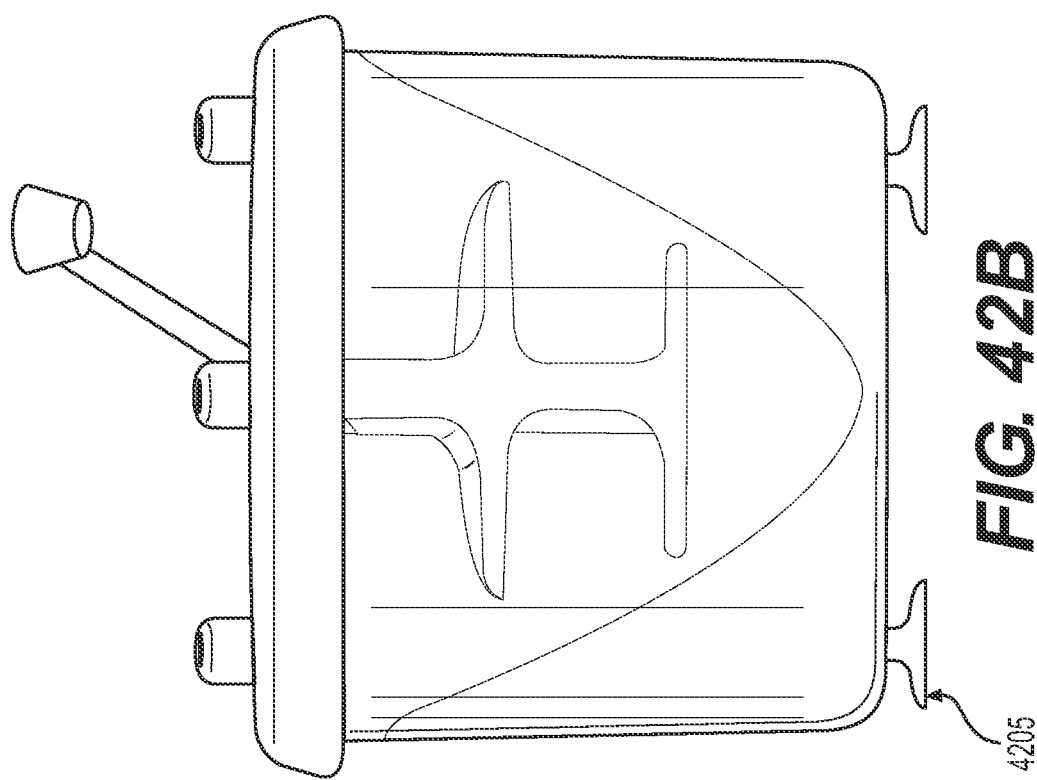
FIGS. 42A and 42B illustrate a mounting system and a tissue treatment system including the mounting system in accordance with various embodiments of the present disclosure.
Figure 42A:
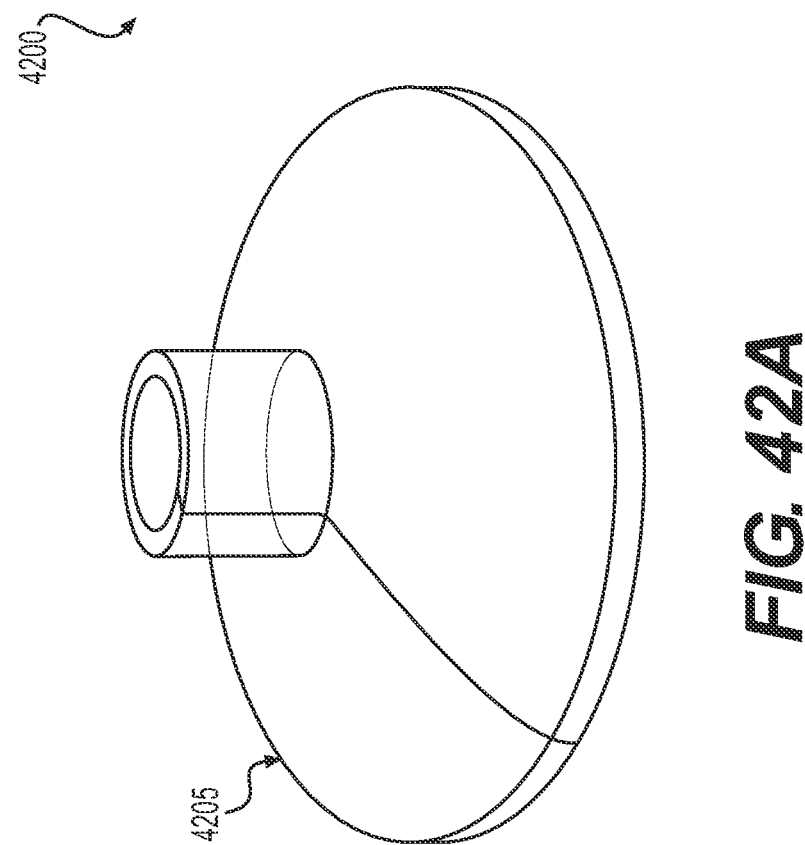

FIGS. 42A and 42B illustrate a mounting system 4205 and a tissue treatment system 4200 including the mounting system 4205, respectively, in accordance with various embodiments of the present disclosure. The mounting system 4205 can include a variety of structures that can secure the treatment system 4200 to a surface to increase stability during vigorous steps of a tissue processing procedure such as operating the mixing blades. In some embodiments, the mounting system 4205 can include hook-and-latch structures or suction cups. The mounting system 4205 can be affixed to the underside of the treatment system 4200 using adhesive, screws, or other appropriate means for attachment. In some embodiments, the mounting system 4205 can prevent the tissue treatment system 4200 from sliding or translating on the surface to which it is attached.

Figure 43:
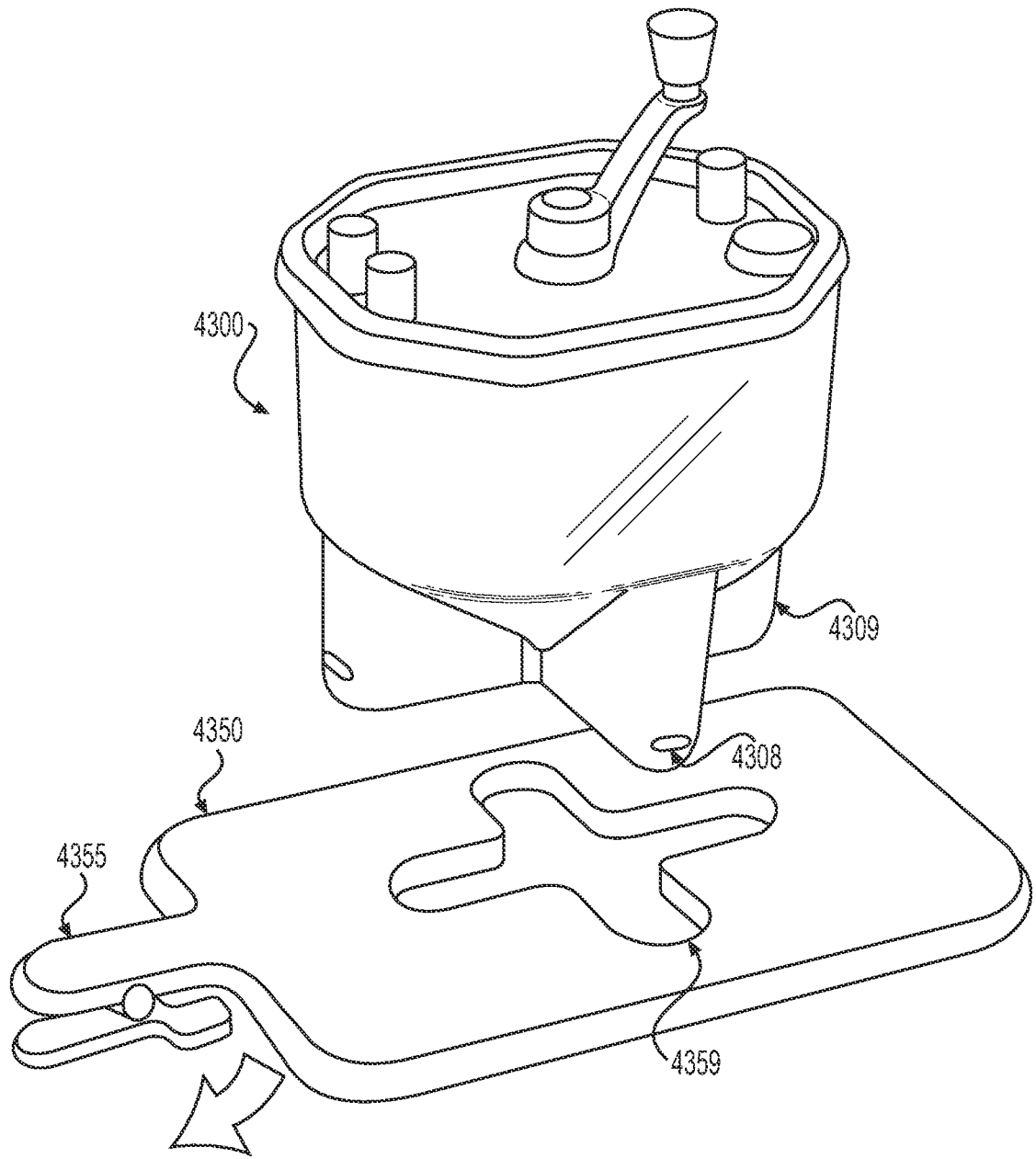
FIG. 43 illustrates a tissue treatment system including a mounting system in accordance with various embodiments of the present disclosure.

FIG. 43 illustrates a tissue treatment system 4300 including a mounting system 4350 in accordance with various embodiments of the present disclosure. In accordance with various embodiments, the mounting system 4350 can be provided separately and can be attached or detached from the tissue treatment system 4300 and a mounting surface in the environment. In some embodiments, the mounting system 4350 can include a clip 4355 to attach the mounting system to a surface in the environment. The clip 4355 can be spring loaded. In some embodiments, the clip 4355 can be adapted to secure the mounting system 4350 to an edge of a Mayo stand. In accordance with various embodiments, the mounting system 4350 can include a depression 4359 that mates with features 4309 having complementary shapes on the tissue treatment system 4300. The features 4309 can include protruding or recessed structures 4308 that interact with corresponding structures within the depression 4359. For example, the protruding structures 4308 can include a ridge or other snap fit feature that interacts with a ridge or recess in the depression to create an interlock that holds the system 4300 in place.

Figure 44B:
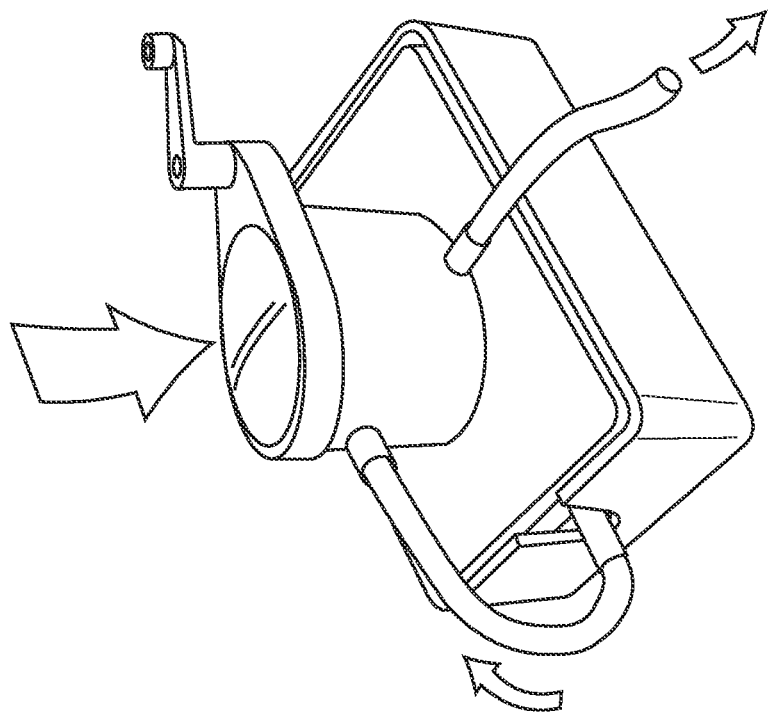
FIGS. 44A and 44B illustrate a tissue treatment system including a storage system for fluid(s) in accordance with various embodiments of the present disclosure.
Figure 44A:
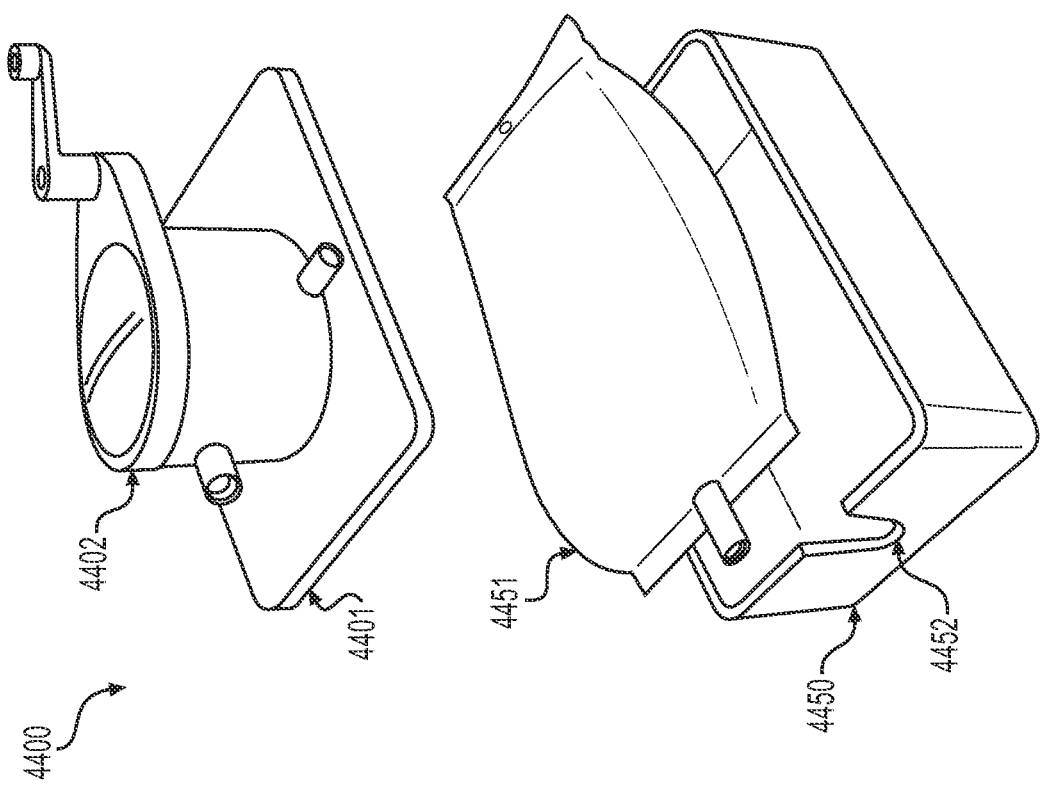

FIGS. 44A and 44B illustrate a tissue treatment system 4400 including a base 4450 to store a fluid bag 4451 in accordance with various embodiments of the present disclosure. The system 4400 can include a tissue treatment device 4402 attached to a flat base 4401 that is lowered onto the fluid bag 4451 in the base 4450. In some embodiments, the flat base 4401 is undersized compared to the dimensions of the base 4450 such that the flat base 4401 can pass into the base 4450 from above. According to various embodiments of the present disclosure, the fluid bag 4451 can include a variety of fluids relevant to tissue processing including water, Ringer's solution, or a rinse solution. In many embodiments, the weight of the liquid in the fluid bag 4451 provides additional stability to the system 4400. When assembled, a hole 4452 in the base 4250 can allow a tube to pass through from the fluid bag 4451 to the treatment device 4402. In some embodiments, the user can apply downward force to the flat base 4401 to "pump" fluid from the fluid bag 4451 into the tissue treatment device 4402.

FIGS. 45A and 45B illustrate a tissue treatment system 4500 including base 4550 for storage of a fluid bag 4551 in accordance with various embodiments of the present disclosure. In some embodiments, the fluid bag 4551 can act as a weight to increase stability of the system 4500 and prevent tipping or sliding of the system 4500. In some embodiments, the system 4500 can include a bag spike 4520 to both pierce the fluid bag 4551 and convey the fluid from the fluid bag 4551 into the mixing unit 4502. The bag spike 4520 can include a stopcock 4521 in some embodiments to open or close the flow of fluid from the fluid bag 4551 in some embodiments. The bag spike 4520 can include an elbow joint or bend in some embodiments. In some embodiments, the system 4500 can include a cover 4504 that can be closed over the fluid bag 4551 to provide protection and prevent accidental puncture of the fluid bag 4551.

FIGS. 46A and 46B illustrate perspective and side views, respectively, of a tissue treatment system 4600 in accordance with various embodiments of the present disclosure. The system 4600 can include a wide base 4630 to provide increased stability for the system 4600 during steps of a tissue treatment procedure. In an exemplary embodiment, tubes 4602a-c can pass into the wide base 4630 and exit from system 4600 through the wide base 4630. By passing the tubes 4602a-c into the wide base 4630, the tubes are well-secured and stay out of the user's way during steps of the surgical procedure. In some embodiments, access to the system 4600 through each tube 4602a-c can be regulated using a valve 4612. Exemplary valves 4612 can include two-way (i.e., on/off) valves or three-way (i.e., tube 1, tube 2, off) valves. For example, a three-way valve can be used to control the patient tube 4602b to switch between liposuction (e.g., patient tissue extraction), Ringer's solution, or all closed. In some embodiments, the patient tube 4602b can connect to a T-connector to split the connection. In some embodiments, the extraction tube 4602c can be connected to the bottom of a filtering structure to enable extraction of the processed tissue. In some embodiments, a vacuum can be applied to the vacuum tube 4602a to remove waste. In some embodiments, the system 4600 can include a rotating dial 4608 to control vent access to the system 4600.

FIG. 47 illustrates a tissue treatment system 4700 with a wash cycle counter 4710 in accordance with various embodiments of the present disclosure. The wash cycle counter 4710 can notify a user of the number of wash cycles that have been performed. In some embodiments, the wash cycle counter 4810 can engage a mechanism after a specified number of wash cycles have been completed. The mechanism, which can include a brake, can prevent the mixing handle from turning after the specified number of wash cycles has been achieved. In various embodiments, the number of washes indicated by the wash cycle counter 4810 can be advanced manually by the user or can be advanced based upon the number of turns made by the mixing handle.

Figures 48A, 48B:
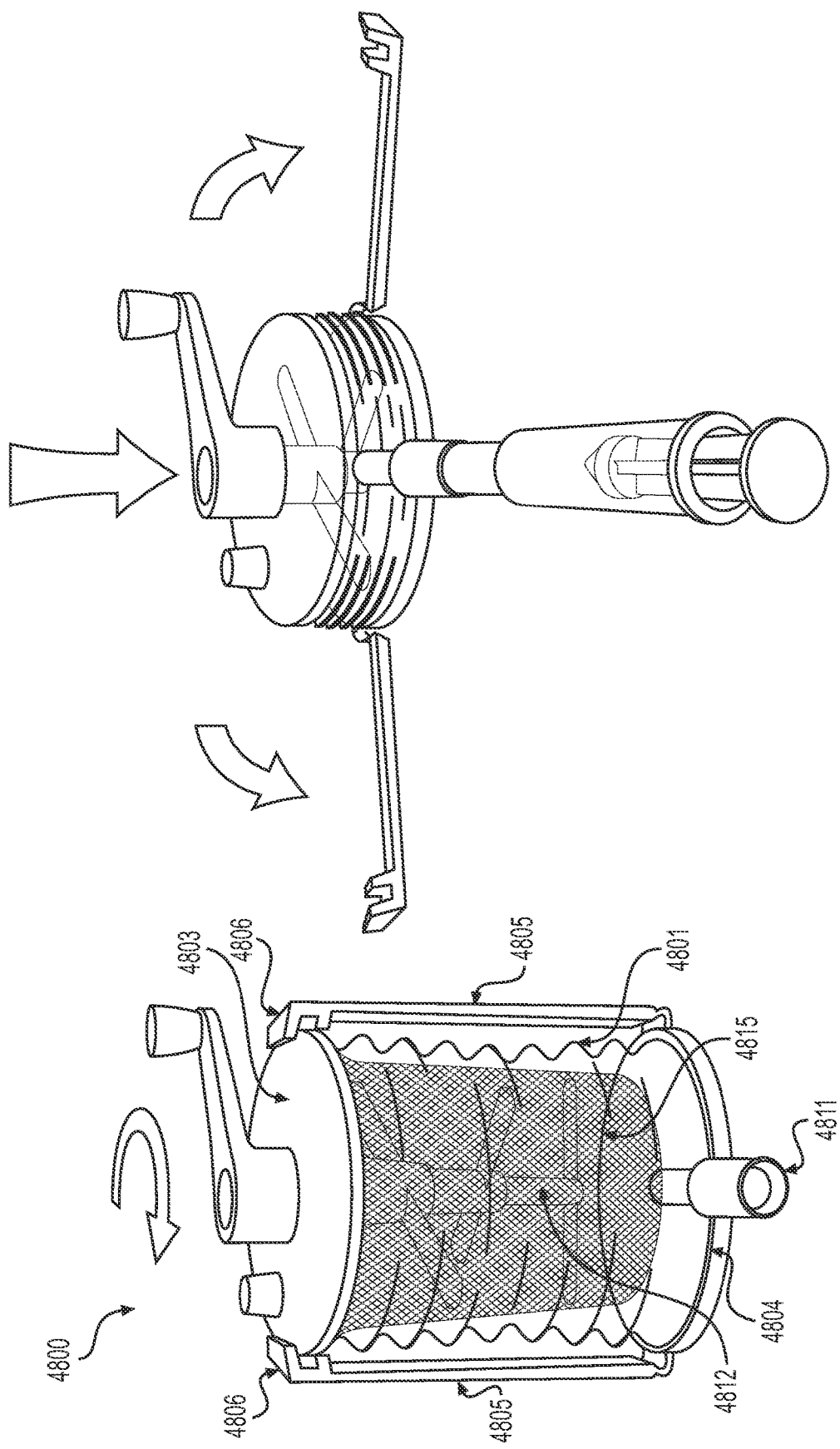
FIGS. 48A and 48B illustrate a collapsible tissue treatment system in uncollapsed and collapsed states, respectively, in accordance with various embodiments of the present disclosure.

FIGS. 48A and 48B illustrate a collapsible tissue treatment system 4800 in uncollapsed and collapsed states, respectively, in accordance with various embodiments of the present disclosure. The collapsible tissue treatment system 4800 can include a top plate 4803 and a bottom plate 4804 with a foldable exterior wall 4801 extending therebetween. Within the foldable exterior wall 4801, the system 4800 can include a collapsible filtering structure 4715 and a collapsible mixing shaft 4812 connected to mixing blades. In an uncollapsed state, arms 4805 extending between the top plate 4803 and the bottom plate 4804 can hold the plates separated. In some embodiments, the arms 4805 can connect to the top plate 4803 or the bottom plate 4804 using clamps 4806 or other suitable fastening systems. The system 4800 in the uncollapsed state can be used to perform processing and washing steps of a tissue processing procedure.

In accordance with various embodiments, when the tissue has been adequately washed, the collapsible tissue treatment system 4800 can be collapsed similar to an accordion to force tissue towards an extraction port 4811. In some embodiments, the clamps 4806 of the arms 4805 can be disengaged from the top plate 4803 or bottom plate 4804 and can swing away. The top plate 4803 can then be urged toward the bottom plate 4804 to reduce a volume within the foldable exterior wall 4801.

The collapsible filtering structure 4815 can include a mesh or other unstructured filtering element lacking reinforcement in some embodiments. The collapsible mixing shaft 4812 can comprise segments in some embodiments wherein the segments slide into one another from bottom to top or top to bottom. The segments can have a flared shape to prevent entry of fluids between segments when the mixing shaft 4812 is in the extended position.

FIGS. 49A-49C illustrate a tissue treatment system 4900 in accordance with various embodiments of the present disclosure. In accordance with various embodiments, the tissue treatment system 4900 can include an outer cover 4901 enclosing a mesh filter 4915. The tissue treatment system 4900 can include an attachment feature 4970 to hang or suspend the system 4900 in the vicinity of the patient. The tissue treatment system 4900 can allow agitation, mixing, and extraction of tissue from the device by hand and without the use of mixing blades as shown in FIG. 49B.

In some embodiments, the outer cover 4901 can be made of a leak resistant but flexible material such as rubber. As illustrated, several ports 4902 (i.e., liposuction port, vacuum port, rinse port, extraction port) can extend through the outer cover 4901. Some ports 4902 (e.g., the rinse port, liposuction port, and extraction port) can further extend to the interior of the mesh filter 4915. The tube connected to each port 4902 can be clamped or unclamped to allow or prevent flow into the port 4902, respectively.

The attachment feature 4970 can enable the system 4900 to be placed at a convenient location within the surgical space. For example, surface space is often limited in the operating room to allow surgeons freedom of movement near the patient. The attachment feature 4970 can allow the system to be attached to any object in the operating room such as a patient gown, surgical drape, Mayo stand, or IV stand. In some embodiments, the attachment feature 4970 can include a loop to allow suspension of the system from the loops of the IV pole as shown in FIG. 49C. In some embodiments, the attachment feature 4970 can include a clip or clamp that can be attached to a drape or clothing.

Figure 50:
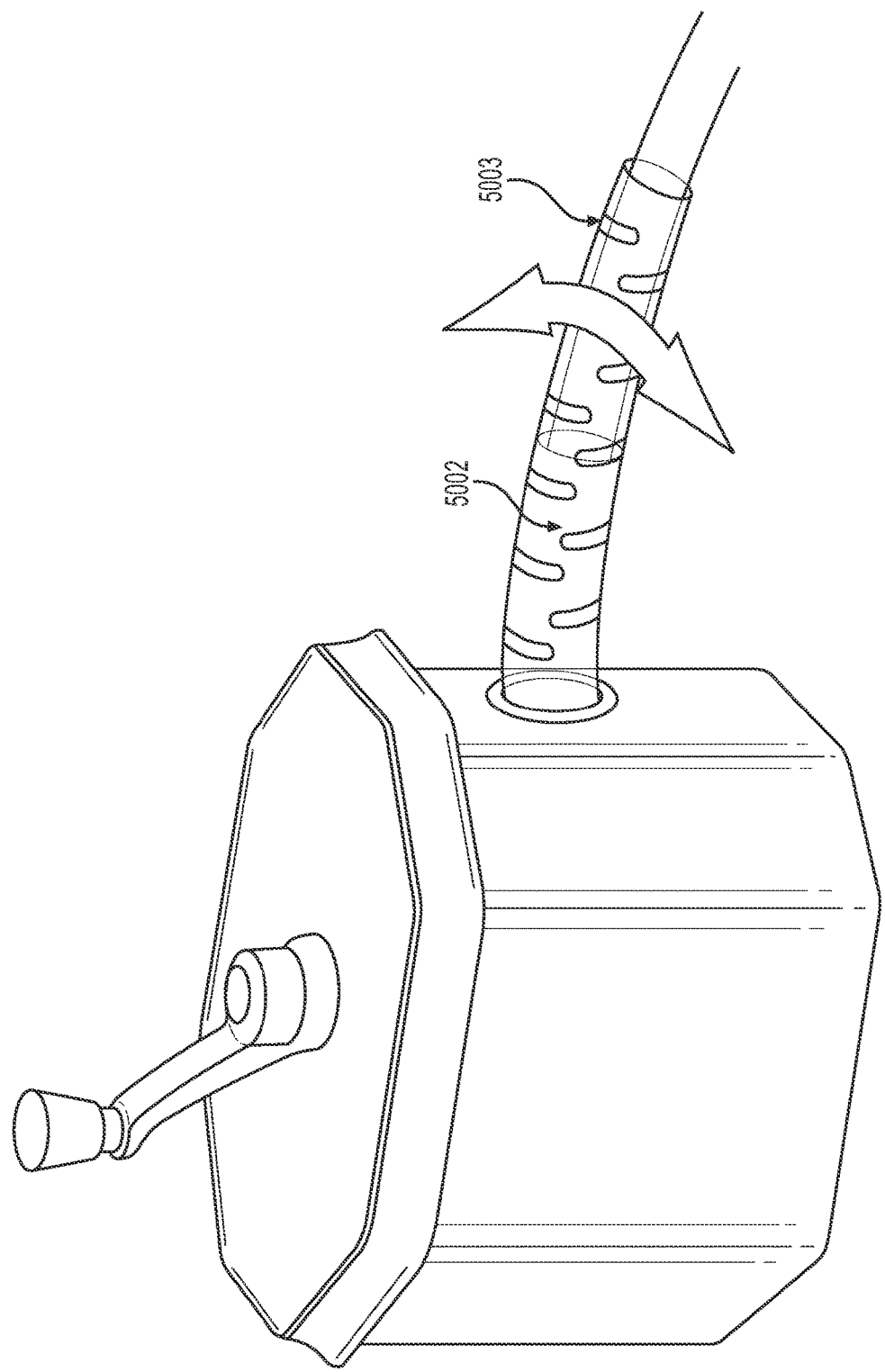
FIG. 50 illustrates a tissue treatment system in accordance with various embodiments of the present disclosure.

FIG. 50 illustrates strain relief for a tube connected to a port in a tissue treatment system in accordance with various embodiments of the present disclosure. In some embodiments, the ports 5002 can be covered by a flexible tubing connector 5003 to ease strain on the connection between the port and the tube. The tubing connector 5003 can be made of a soft material in some embodiments. The tubing connector 5003 can help prevent the system from being jostled too harshly during manipulation and movement of the tubes and/or during the tissue processing procedure.

FIG. 51A-51C illustrate views of a tissue treatment system 5100 in accordance with various embodiments of the present disclosure. The tissue treatment system can include ports 5102, mixing blades 5130, a multi-position switch 5106, and a handle 5104 to operate the mixing blades 5130. In accordance with various embodiments, the handle 5104 can rotate about an axis 5110 that is tilted with respect to the axis of a shaft connected to the mixing blades. In alternative embodiments, the handle 5104 can rotate about an axis that is parallel to the shaft connected to the mixing blades and tilted with respect to the surface normal of the bottom of the device. In some embodiments, the multi-position switch 5106 can step the user through the steps of the tissue processing procedure and open and close the corresponding port connections for each step as described above with reference to earlier figures. A transfer port 5160 can exit from the front of the device.

Figure 52B:
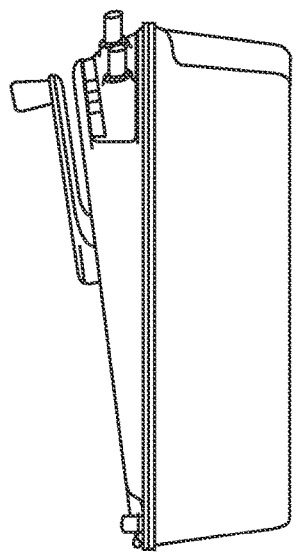
FIGS. 52A-52C illustrate views of a tissue treatment system in accordance with various embodiments of the present disclosure.
Figure 52C:
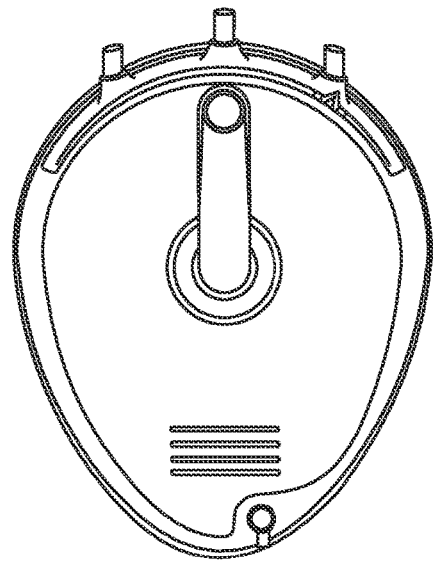
Figure 52A:
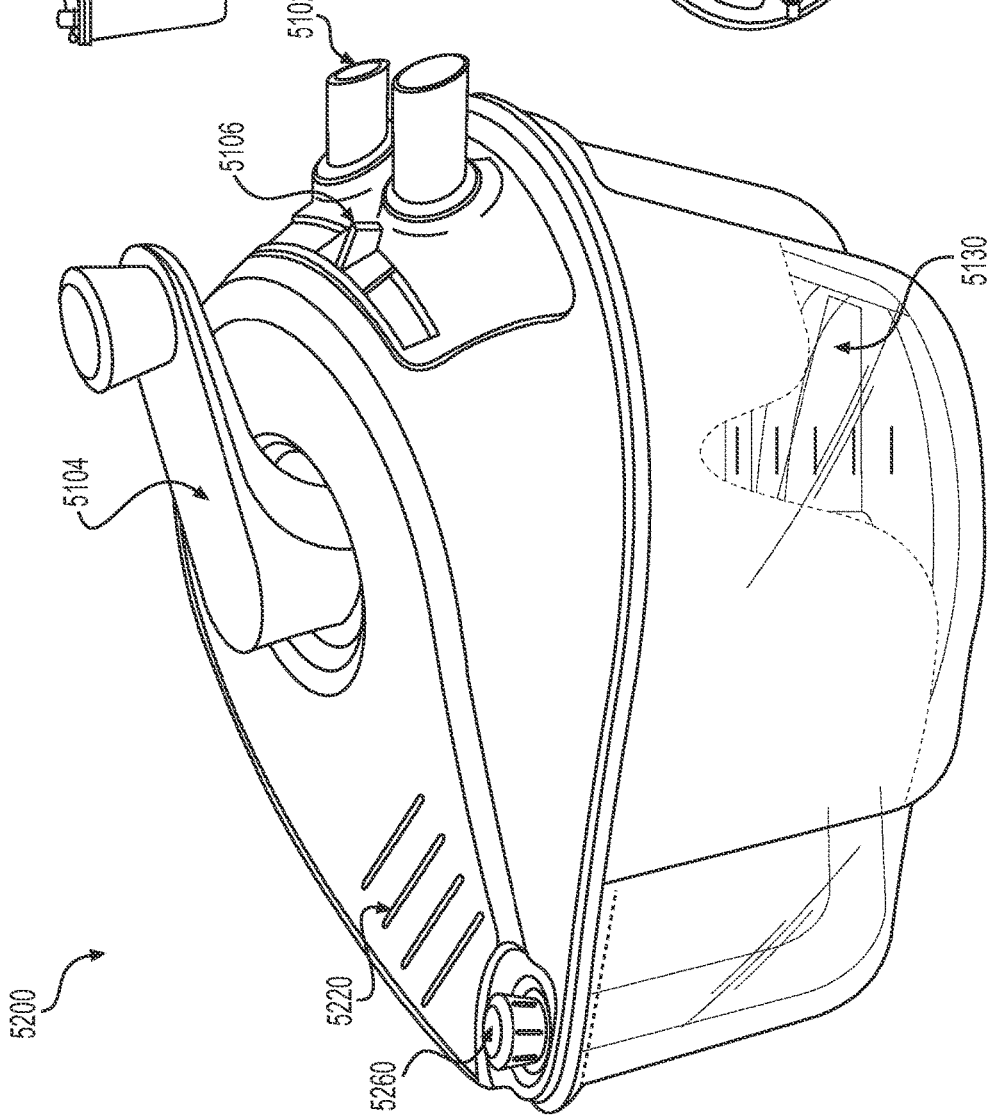

FIG. 52A-52C illustrate views of a tissue treatment system 5200 in accordance with various embodiments of the present disclosure. The system 5200 can include ports 5102, handle 5104, mixing blades 5130, and multi-position switch 5106 as described above with reference to FIG. 51A. In accordance with various embodiments, the transfer port 5260 can extend out of a top surface of the system 5200 and connect internally to a tube that passes to the bottom of the device. The system 5200 can include a gripping surface 5220 in some embodiments that allows the user to better stabilize the system 5200 during tissue processing.

Figure 53B:
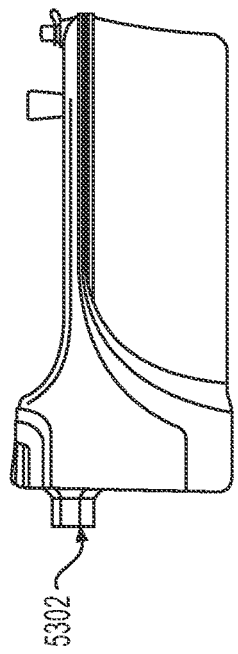
FIGS. 53A-53C illustrate views of a tissue treatment system in accordance with various embodiments of the present disclosure.
Figure 53C:
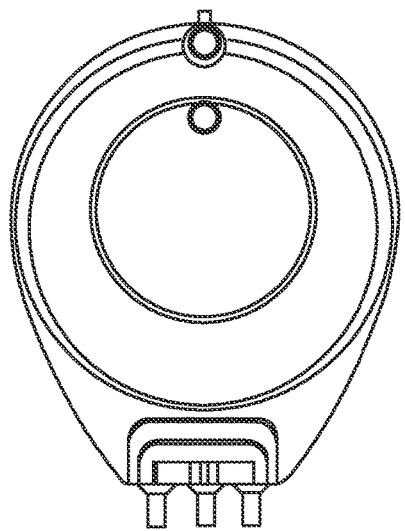
Figure 53A:
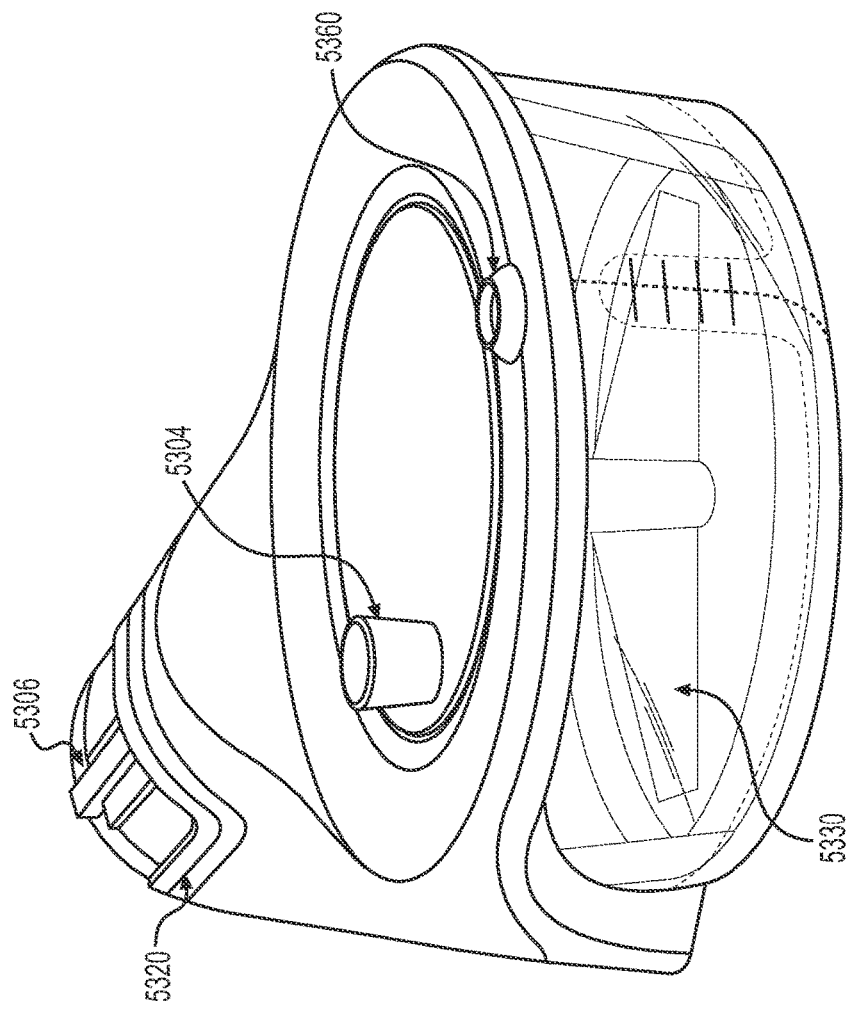
Figure 54B:
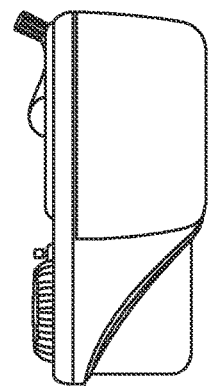
FIG. 54A-54E illustrate views of a tissue treatment system in accordance with various embodiments of the present disclosure.
Figure 54C:
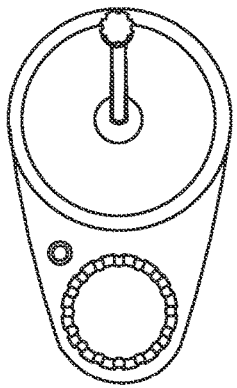
Figure 54D:
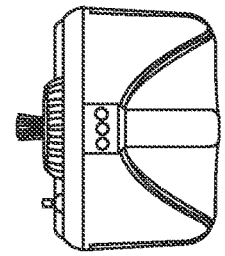
Figure 54E:
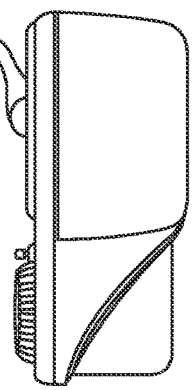
Figure 54A:
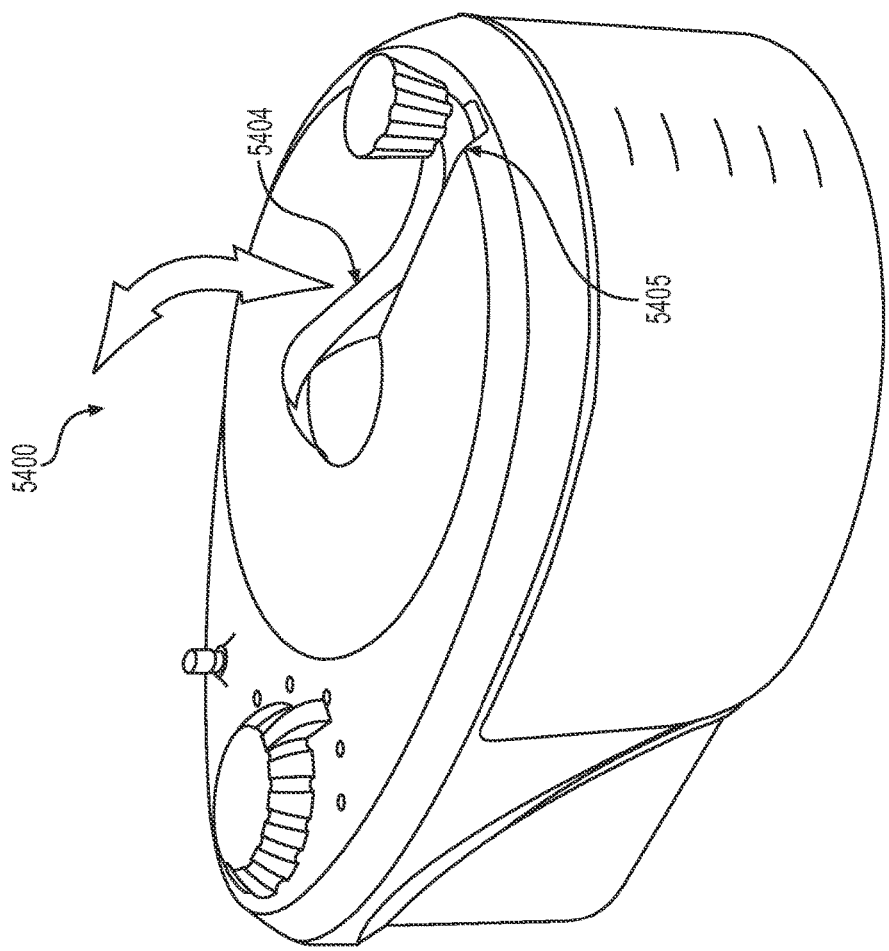

FIG. 53A-53C illustrate views of a tissue treatment system 5300 in accordance with various embodiments of the present disclosure. The tissue treatment system can include ports 5302, mixing blades 5330, a multi-position switch 5306, and a handle 5304 to operate the mixing blades 5330. In some embodiments, the bulk of the handle 5304 can be flush with a top surface of the system 5300 to provide a low profile. In some embodiments, the multi-position switch 5306 can include a rotational dial that is flush with the outer surface of the system 5300. The rotational dial can step the user through the steps of a tissue processing procedure and open and close corresponding connections for each step. In some embodiments, the system 5300 can include a grip area 5320 to allow the user to better stabilize the system 5200 during tissue processing.

FIG. 54A-54E illustrate views of a tissue treatment system 5400 in accordance with various embodiments of the present disclosure. In some embodiments, the tissue treatment system can include a flip-out handle 5404. The flip-out handle 5404 can be flipped out to a first position to provide a rotating handle grippable by a user to move the mixing blades. When the flip-out handle 5404 is not in use, it can be flipped in and rested in a second position in a groove 5405 on a top surface of the system 5400. In the flipped-in position, the flip-out handle 5404 is stowed away where it will not be bumped during further processing steps. In addition, immobilization of the flip-out handle 5404 will prevent accidental manipulation of the mixing blades at points in the procedure where such motion is not desirable.

While the present invention has been described herein in conjunction with preferred embodiments, a person of ordinary skill in the art can effect changes, substitutions or equivalents to the systems and methods described herein, which are intended to fall within the appended claims and any equivalents thereof.

The invention claimed is:

1. A tissue treatment system, comprising:
   a processing container, including an exterior side wall, a top wall, and a bottom wall, wherein the exterior side wall, top wall, and bottom wall surround an interior volume for holding tissue;
   a filtering structure having a rigid frame and a mesh filter, wherein the filtering structure extends from the top wall to the bottom wall to divide the interior volume into a first portion interior to the filtering structure and a second portion exterior to the filtering structure, and wherein the filtering structure is sloped inwardly from the top wall to the bottom wall; and
   an extraction port configured to extract tissue from the first portion of the interior volume through the bottom wall, the extraction port having a first opening positioned within the first portion of the interior volume of the container.

2. The tissue treatment system of claim 1, wherein the rigid frame comprises:
   a first frame member attached to the top wall;
   a second frame member attached to the bottom wall; and
   at least one rib member connecting the first frame member to the second frame member.

3. The tissue treatment system of claim 2, wherein the rigid frame forms at least one window, wherein the mesh filter covers the at least one window and is mated to and supported by the rigid frame.

4. The tissue treatment system of claim 2, wherein the first frame member includes a first diameter and the second frame member includes a second diameter, wherein the first diameter is greater than the second diameter.

5. The tissue treatment system of claim 2, wherein the mesh filter comprises cut-through holes, and wherein the first frame member comprises a boss feature to engage with the cut-through holes to position the mesh filter.

6. The tissue treatment system of claim 1, further comprising a spring and needle gauge to indicate the mass of tissue present within the inner chamber of the system.

7. The tissue treatment system of claim 1, wherein the rigid frame is formed from a single piece of solid material.

8. The tissue treatment system of claim 1, further comprising a telescoping mixing paddle disposed within the first portion of the interior volume, wherein the telescoping mixing paddle comprises at least one blade at a first axial position and at least one blade at a second axial position different than the first axial position.

9. The tissue treatment system of claim 8, wherein the blades at different axial positions can rotate with respect to one another.

10. The tissue treatment system of claim 8, wherein the telescoping mixing paddle is convertible to a piston form.

11. The tissue treatment system of claim 1, further comprising a mixing and auger system including a central shaft having at least one mixing blade and an auger, wherein the central shaft extends from the top wall and into the first portion of the interior volume.

12. The tissue treatment system of claim 1, wherein the mesh filter is formed from a single piece of material.

13. The tissue treatment system of claim 1, wherein the mesh filter has holes configured to fit the rigid frame such that the holes of the mesh filter align with solid portions of the rigid frame.

14. The tissue treatment system of claim 1, further comprising a plurality of tube-restriction devices.

15. The tissue treatment system of claim 14, wherein the plurality of tube-restriction devices comprises press-down buttons.

16. The tissue treatment system of claim 14, wherein the plurality of tube-restriction devices comprises snap-down panels.

17. The tissue treatment system of claim 1, further comprising a base attached to the bottom wall.

18. The tissue treatment system of claim 1, further comprising a flip-out handle that is rotatable in a first position and rests in a groove in a second position.

19. The system of claim 1, further comprising a sterile drape pre-attached to the container.

20. The system of claim 19, wherein the sterile drape includes an adhesive element to adhere to a surface.

* * * * *